US012768833B2

(12) United States Patent
Paterlini-Brechot et al.

(10) Patent No.: US 12,768,833 B2
(45) Date of Patent: Oct. 20, 2026

(54) PROCESS FOR MULTI-ANALYSES OF RARE CELLS EXTRACTED OR ISOLATED FROM BIOLOGICAL SAMPLES THROUGH FILTRATION

(71) Applicants: NARADA SAS, Paris Cedex (FR); UNIVERSITÉ CÔTE D'AZUR, Nice Cedex (FR); CENTRE HOSPITALIER UNIVERSITAIRE DE NICE, Nice Cedex (FR); UNIVERSITÉ PARIS CITÉ, Paris (FR); ASSISTANCE PUBLIQUE-HOPITAUX DE PARIS (AP-HP), Paris (FR); INSTITUT NATIONAL DE LA SANTE ET DE LA RECHERCHE MEDICALE (INSERM), Paris Cedex (FR)

(72) Inventors: Patrizia Paterlini-Brechot, Paris (FR); Paul Hofman, Falicon (FR); Sophie Marie Genevieve Laget, Paris (FR); Thierry Capiod, Paris (FR)

(73) Assignees: NARADA SAS, Paris (FR); UNIVERSITÉ CÔTE D'AZUR, Nice (FR); CENTRE HOSPITALIER UNIVERSITAIRE DE NICE, Nice (FR); UNIVERSITÉ PARIS CITÉ, Paris (FR); ASSISTANCE PUBLIQUE-HOPITAUX DE PARIS (AP-HP), Paris (FR); INSTITUT NATIONAL DE LA SANTE ET DE LA RECHERCHE MEDICALE (INSERM), Paris (FR)

( * ) Notice: Subject to any disclaimer, the term of this patent is extended or adjusted under 35 U.S.C. 154(b) by 0 days.

(21) Appl. No.: 19/010,663

(22) Filed: Jan. 6, 2025

(65) Prior Publication Data

US 2025/0347681 A1 Nov. 13, 2025

Related U.S. Application Data

(60) Division of application No. 16/746,443, filed on Jan. 17, 2020, now abandoned, which is a continuation of application No. 13/901,063, filed on May 23, 2013, now abandoned.

(60) Provisional application No. 61/651,437, filed on May 24, 2012.

(51) Int. Cl.

| | |
|---|---|
| ***C12Q 1/68*** | (2018.01) |
| ***C12Q 1/6876*** | (2018.01) |
| ***C12Q 1/6886*** | (2018.01) |
| ***G01N 33/50*** | (2006.01) |
| ***G01N 33/554*** | (2006.01) |

(52) U.S. Cl.
CPC ....... *G01N 33/5091* (2013.01); *C12Q 1/6876* (2013.01); *C12Q 1/6886* (2013.01); *G01N 33/554* (2013.01)

(58) Field of Classification Search
USPC ................ 435/6.1, 6.11, 91.1, 287.1, 287.2; 436/94, 501; 536/23.1, 24.3, 24.33
See application file for complete search history.

(56) References Cited

U.S. PATENT DOCUMENTS 4,152,184 A * 5/1979 Bacehowski ....... A61M 1/0236 156/303.1
2013/0330721 A1* 12/2013 Tang ................. B01D 39/1692 210/767

FOREIGN PATENT DOCUMENTS

EP 2856153 4/2015

OTHER PUBLICATIONS

"Ammonium Chloride Solution for Red Blood Cell Lysis". Printed on Sep. 27, 2025.*
"Bacteria" from Wikipedia. Printed on Sep. 27, 2025.*
Desitter et al., A New Device for Rapid Isolation by Size and Characterization of Rare Circulating Tumor Cells. Anticancer Research, 31, 427-442, 2011.*
Peck et al., Detection and Quantitation of Circulating Cancer Cells in the Peripheral Blood of Lung Cancer Patients. Cancer Research, 58, 2761-2765, 1998.*
The definition of "Cytomorphology", "Cell Structure and Function", "Molecular Analysis" and "Methods of nucleic acid analysis". Printed on May 14, 2021.
"Immunolabeling" from Wikipedia. Printed on May 14, 2021.
Vona et al., Isolation by size of epithelial tumor cells : a new method for the immunomorphological and molecular characterization of circulatingtumor cells. American Journal of Pathology, 156, 57-63, 2000.
Hofman et al., Cytopathologic Detection of Circulating Tumor Cells Using the Isolation by Size of Epithelial Tumor Cell Method: Promises and Pitfalls, Am. J. Clin. Pathol., 135, 146-156, Jan. 2011.
T. Liu, et al., "Characterization of primary ovarian cancer cells in different culture systems", Oncology Reports, vol. 23, 2010, pp. 1277-1284.
A. Saker, et al., "Genetic characterization of circulating fetal cells allows non-invasive prenatal diagnosis of cystic fibrosis", Prenat Diagn, vol. 26, 2006, pp. 906-916.

(Continued)

*Primary Examiner* — Frank W Lu
(74) *Attorney, Agent, or Firm* — Merchant & Gould P.C.; Daniel J. Pereira

(57) ABSTRACT

A process for isolating or extracting rare cells from a biological sample including filtering a biological sample, which may be treated or diluted, through a filter that has a pore size, pore density or other physical properties that retain rare cells, but which permits other kinds of cells to pass through the filter.

10 Claims, 7 Drawing Sheets

Specification includes a Sequence Listing.

(56) References Cited

OTHER PUBLICATIONS

C. Beroud, et al., "Prenatal diagnosis of spinal muscular atrophy by genetic analysis of circulating fetal cells", The Lancet, vol. 361, Mar. 22, 2003, pp. 1013-1014.
Q. Liu, et al., "The cultivation and identification of tumor stem cells from neuroblastoma derived tumor spheres", Chinese Journal of Cancer, vol. 29, Issue 12, 2010, pp. 1012-1017.
G. Vona, et al., "Impact of cytomorphological detection of circulating tumor cells in patients with liver cancer", Hepatology, vol. 39, No. 3, 2004, pp. 792-797.
J. Lu, et al., "Isolation of circulating epithelial and tumor progenitor cells with an invasive phenotype from breast cancer patients", Int. J. Cancer, vol. 126, No. 3, Feb. 1, 2010, pp. 669-683.
Oxnard et al., "Germline EGFR Mutations and Familial Lung Cancer", Journal of Clinical Oncology, 41, 5274-5284, 2023.
Bourdeaut et al., "ALK germline mutations in patients with neuroblastoma: a rare and weakly penetrant syndrome", European Journal of Human Genetics, 20, 291-297, 2012.
Fergal C. Kelleher, et al., "The emerging pathogenic and therapeutic importance of the anaplastic lymphoma kinase gene", European .Journal of Cancer, 2010, vol. 46, pp. 2357-2368.
D. Ross Camidge, et al., "Activity and safety of crizotinib in patients with ALK-positive non-small-cell lung cancer: updated results from a phase 1 study", Oncology, Oct. 2012, vol. 13, pp. 1011-1019.
Eunice L, Kwak, M.D., Ph.D., et al., "Anaplastic Lymphoma Kinase Inhibition in Non-Small-Cell Lung Cancer", The New England Journal of Medicine, Oct. 28, 2010, vol. 363 (18), pp. 1693-1703.
Yongjun Li, et al., "Evaluation of EML4-ALK Fusion Proteins in Non-Small Cell Lung Cancer Using Small Molecule Inhibitors", Neoplasia, Jan. 2011, vol. 13(1 ), pp. 1-11.
Alice T. Shaw, MD, et al., "Effect of crizotinib on overall survival in patients with advanced non-small-cell lung cancer harbouring ALK gene rearrangement: a retrospective analysis", Lancet Oncol., Oct. 2011, vol. 12(11 ), pp. 1-20.
Benjamin Solomon, MBBS. PhD, et al , "ALK Gene Rearrangements A New Therapeutic Target in a Molecularly Defined Subset of Non-small Cell Lung Cancer", Journal of Thoracic Oncology, Dec. 2009, vol. 4(12), pp. 1450-1454.
Thomas R. Webb, et al., "AnapLastic lymphoma kinase: role in cancer pathogenesis and small-molecule inhibitor development for therapy", Expert Rev Anticancer Ther., Mar. 2009, vol. 9(3), pp. 1-46.
Young Lim Choi et al , "Identification of Novel isoforms of the EML4-ALK Transforming Gene in Non-Small Cell Lung Cancer", Cancer Research, Jul. 1, 2008, vol. 68(13), pp. 4971-4976.
Leora Horn, et al., "EML4-ALK: Honing In on a New Target in Non-Small-Celi Lung Cancer", J. Clin. Oncol., Sep. 10, 2009, vol. 27(26), pp. 4232-4235.
Eva Lin, et al., "Exon Array Profiling Detects EML4-ALK Fusion in Breast, Colorectal, and Non-Small Cell Lung Cancers", Mol. Cancer Res , Sep. 2009, vol. 7(9), pp. 1466-1476.
Erica L. Carpenter, et al., "Targeting ALK in neuroblastoma-preclinical and ciinical advancements", Nat. Rev. Clin, Oncol., 2012, vol. 9(7), pp. 1--17.
Yuyan Chen et al., "Oncogenic mutations of ALK kinase in neuroblastoma", Nature, Oct. 16, 2008, vol. 455, pp. 971-975.
K. Pulford, et al., "Anaplastic Lymphoma Kinase Proteins in Growth Control and Cancer", Journal of Cellular Physiology, 2004, vol. 199, pp. 330-358.
Marta Salido, MSc., et al., "Increased ALK Gene Copy Number and Amplification are Frequent in Non-small Cell Lung Cancer", J Thorac Oncol., Jan. 2011, vol. 6(1), pp. 21-27.
Manabu Soda, et al., "Identification of the transforming EML4-ALK fusion gene in non small Cell lung cancer", Nature, Aug. 2007, vol. 448, pp. 1-7.
Cohen et al, "FDA Drug Approval Summary: Erlotinib (Tarvecva®)Tablets", The Oncologist (2005), vol. 10, pp. 461-466.
Marissa N. Balak, et al., "Novel D761Y and Common Secondary T790M Mutations in Epidermal Growth Factor Receptor—Mutant Lung Adenocarcinomas with Acquired Resistance to Kinase Inhibitors". Clinical Cancer Res , Nov. 1, 2006, vol. 12(2), pp. 6494-6501.
Makoto Maemondo, M.D., Ph.D., et al., "Gefitinib or Chemotherapy for Non-Small-Cell Lung Cancer with Mutated EGFR", The New England Journal of Medicine, 2010, vol. 352, pp. 2380-2388.
William Pao et al., "Rational biologically based treatment of EGFR-mutant non-small-cell lung cancer", Nat. Rev. Cancer, Nov. 2010, vol. 10(11), pp. 760-774.
Calcun Zhou, et al., "Erlotinib versus chemotherapy as first-line treatment for patients witll advanced EGFR mutation-positive non-small-cell lung cancer (Optimal, CTONG-0802): a multicentre, open-label, randomised, phase 3 study", Lancet Oncology, Aug. 2011, vol. 12, pp. 735-742.
Inhee Chung, et al., "Spatial control of EGF receptor activation by reversible dimerization on living cells", Nature, Apr. 2010, vol. 464, pp. 783-788.
Toni M. Brand, et al., "The Nuclear Epidermal Growth Factor Receptor Signaling Network and its Role in Cancer", Discov. Med , Nov. 2011, vol. 12(66), pp. 1-21.
William Pao, et al., "Acquired Resistance of Lung Adenocarcinomas to Gefitinib or Erlotinib is Associated with a Second Mutation in the EGFR Kinase Domain", PLOS Medicine, Mar. 2005, vol. 2(3), pp. 0225-0235.
Wykosky,. et al., "Therapeutic targeting of epidermal growth factor receptor in human cancer: successes and limitiations," Chin. J. Cancer, 2011, 30(1 ), pp. 5-12.
Wu, el al., "Management of acquired resistance to EGFR TKI-targeted therapy in advanced non-small cell lung cancer", Molecular Cancer, 2018, Article No. 38; pp. 1-7.
ALK Inhibitor—Wikipedia entry retrieved from https://en.wikipedia.org/w/index.php?title=ALK_inhibitor&oldid=1198911411 on Mar. 6, 2024, 6 pages.
Cinque et al., "MEN 1 gene mutation with parathyroid carcinoma: first report of a familial case". Oncology Letters, 14, 23-30, 2017.
Chorti et al., "Sporadic parathyroid adenoma: an updated review of molecular genetics". Frontiers in Endocrinology, 14, 1180211, 2023.
Kemp et al., "CDC4 Mutations Occur in a Subset of Colorectal Cancers but Are Not Predicted to Cause Loss of Function and Are Not Associated with Chromosomal Instability". Cancer Res., 65, 11361-11366, 2005.
The definition for "adenomas". Printed on Oct. 18, 2022.
"Gefitinib" and "Erlotinib" from Wikipedia. Printed on Oct. 18, 2022.
Lee et al., "Comparative analyses of overall survival in patients with anaplastic lymphoma kinase-positive and matched wild-type advanced nonsmall cell lung cancer". 118, 3579-3586, 2012.

* cited by examiner

PROCESS FOR MULTI-ANALYSES OF RARE CELLS EXTRACTED OR ISOLATED FROM BIOLOGICAL SAMPLES THROUGH FILTRATION

CROSS-REFERENCE TO RELATED APPLICATIONS

This application is a Divisional of U.S. application Ser. No. 16/746,443, filed Jan. 17, 2020, which is a Continuation of U.S. application Ser. No. 13/901,063, filed May 23, 2013, now abandoned; which claims priority under 35 U.S.C. § 119 (e) to U.S. Provisional Application No. 61/651,437, filed May 24, 2012 which is incorporated by reference in its entirety.

REFERENCE TO SEQUENCE LISTING

In accordance with 37 CFR § 1.52(e)(5) and with 37 CFR § 1.831, the specification makes reference to a Sequence Listing submitted electronically as a .xml file named 19775.0001FD1 sequence listing .xml. Said .XML copy, created and filed herewith is 4,000 bytes in size. The entire contents of the Sequence Listing are hereby incorporated by reference.

BACKGROUND OF THE INVENTION

Field of the Invention

The invention involves the isolation of rare cells from biological samples by filtration and the subsequent analysis of these rare cells and their components. Rare cells have features or appear in biological samples at frequencies that distinguish them from other kinds of cells. Types of rare cells include rare tumor or rare cancer cells, rare kinds of endothelial cells, rare fetal cells and rare infected white blood cells (leukocytes).

Description of the Related Art

Rare cells. Rare cells are present in absolute or relative low numbers in biological samples obtained from humans or animals. The presence of rare cells frequently correlates with a particular disease, disorder or condition. For example, rare tumor cells can be found in the blood of subjects having tumors or cancers.

Kinds of Rare Cells. There are many different kinds of rare cells and rare cells non-exclusively may be:

- epithelial cells and their progenitors, mesenchymal cells and their progenitors, mature and immature endothelial cells and their progenitors, fibroblasts and their progenitors, and melanocytes and their progenitors;
- monocytes and macrophages and their progenitors, activated lymphocytes and their progenitors, plasma cells and their progenitors, eosinophils and their progenitors, basophils and their progenitors and megakaryocytes and their progenitors;
- stem cells of any subtype;
- fetal cells of any origin and type including lymphoid, erythroid, myeloid, stem fetal cells, trophoblastic cells such as cytotrophoblasts and syncytiotrophoblasts, and embryonic cells; and
- tumor cells of any origin and type and of any degree of differentiation including stem tumor cells, tumor microemboli, aggregated tumor cells, collective tumor cells of any type, and atypical cells of any origin and type.

Some kinds of rare cells are pathological cells. Examples of such pathological cells include tumor or cancer cells such as cells derived or originating from lung cancer, prostate cancer, colon cancer, breast cancer, pancreas cancer, kidney cancer, liver cancer, gastric cancer, esophagus cancer, and any type of carcinoma, sarcoma, myelomas, melanomas, osteosarcomas, neuroblastomas, leukemias and lymphomas.

Rare cells are also associated with conditions where the number of rare cells in a biological sample is increased or decreased by the pathology. These include:

- endothelial cells present in pathologically higher numbers in the blood of patients with cancer or patients with cardiovascular disorders like heart stroke;
- cells carrying intracellular viruses, bacteria or other pathogenic agents, like HIV, HBV, HPV, *Shigella, Leishmania, bacillum* of tuberculosis, infected monocytes, infected macrophages, infected lymphocytes, activated lymphocytes; and
- cells carrying mutations which are associated with genetic diseases, like fetal cells from a fetus affected by a genetic disorder, like aneuploidy 21, 13, 18, XXY, XO, thalassemia, cystic fibrosis, spinal muscular atrophy, Duchenne's disease, Huntington's disease, etc., and cells carrying genetic mutations or molecular characteristics associated with susceptibility to defined pathologies like viral infections, inflammations, chronic degenerative diseases, Alzheimer, diabetes, metabolic disorders.

Rare cells may also be associated with non-pathological conditions, such as pregnancy.

Rare cells can typically represent one cell in from about $10^3$ to about $10^{10}$ cells, from about $10^4$ to about $10^{10}$ cells, from about $10^5$ to about $10^{10}$ cells, from about $10^6$ to $10^{10}$ cells, from about $10^7$ to about $10^{10}$ cells, or even from about $10^8$ to about $10^{10}$ cells of a cell population in a biological fluid. Rare cells can typically represent less than 500 cells in 1 mL of biological fluid, less than 200 cells in 1 mL of biological fluid, less than 100 cells in 1 mL of biological fluid, less than 50 cells in 1 mL of biological fluid or even less than 10 cells in 1 mL of biological fluid. For instance, circulating tumor cells (CTC) are known to be present typically 1-10 or 1 to 500 CTC among about $6\times10^6$ leukocytes, about $2\times10^8$ platelets and about $4\times10^9$ erythrocytes per mL of blood [75].

Prior Methods for Isolating Rare Cells.

Rare cells can be extracted or isolated from biological samples. Extracted cells are cells extracted from a liquid sample without isolation from other cells. Isolated cells rare cells are rare cells isolated from other kinds of cells present in a liquid sample. The proportion of rare versus non-rare cells extracted or isolated from biological samples varies, thus the degree of purity of extracted or isolated rare cells can be variable.

Several methods have been proposed to extract or isolate rare cells from biological samples; in particular, several methods have been reported to isolate tumor or fetal cells from blood. However, these methods do not address the triple challenge of extracting or isolating of rare cells with (i) minimal or no loss, (ii) extraction or isolation of rare cells with minimal or no selection bias, and (iii) extraction or isolation of rare cells in a way that permits their facile or simultaneous use in multiple analytic procedures.

Methods that only recover some of the rare cells in a sample quantitatively impair the use of the isolated or extracted rare cells in subsequent analytic procedures. These methods can also introduce selection bias.

Selection bias occurs when an extraction or isolation method leads to loss of one or several types of selected rare cells in a sample. For example, a method that isolates tumor cells from a blood sample by binding the rare tumor cells to anti-epithelial cell antibodies results in the loss of rare tumor cells that do not express epithelial cell antigens that bind to the antibody.

Harsh extraction or isolation procedures or procedures that otherwise change the detectable features of the isolated or extracted rare cells compromise their use in subsequent analytic procedures.

Diagnostic Importance of Rare Cells. The detection and characterization of rare cells and their use in diagnosis and therapy is expected to be increasingly important in human and veterinary clinical practice and for research. Rare cells are particular valuable for use in personalized medicine or theranostics, a process of individualized diagnostic therapy for a patient based on his or her particular genetic characteristics and on the characteristics of his or her rare cells. In this setting, rare cells need to be analyzed by multiple approaches providing their diagnostic identification and extensive characterization. As an example, rare cells isolated from blood of patients affected by cancer can be characterized by molecular analyses aimed to detect gene mutations with prognostic and/or theranostic value. However, if only molecular analyses targeting gene mutations are performed without analyses aiming to diagnose the presence or absence of tumor cells in blood, the test's result can be affected by bias. If fact, if rare cells isolated from blood of a given patient do not comprise tumor cells, the absence of gene mutation in the isolated rare cells will not indicate absence of gene mutation in circulating tumor cells. Hence, multiple analyses performed on rare cells extracted or isolated from biological samples are needed in order to obtain reliable information to be used to select targeted treatments, to follow their efficacy and to detect possible drug resistance.

Furthermore, rare cells extracted or isolated from blood or other biological samples may be used as an alternative to samples obtained through invasive surgical or semi-surgical methods, comprising non-exclusively surgical and semi-surgical interventions, biopsy, laparocentesis, thoracentesis, paracentesis, spinal puncture, amniocentesis, chorionic villus sampling and cordocentesis. In this setting, rare cells represent precious material that needs to be interrogated by multiple analyses for diagnostic and/or theranostic use and for extensive molecular and/or genetic characterization.

Lung Cancer Derived Rare Cells. Lung cancer is the most prevalent neoplasm and the major cause of tumor-related mortality worldwide [1-5]. Despite recent advances in the management of resected lung cancers and more effective treatment of metastatic tumors, the cure rate of patients with lung cancer remains low. However, the recent discovery of driver oncogenic mutations in lung carcinomas and the increasing development of targeted therapies show new encouraging results in advanced stage patients [6-8]. Among these therapies, gefitinib and erlotinib, tyrosine-kinase inhibitors raised against the epidermal growth factor receptor (EGFR), which exhibit an activating tyrosine mutation in 10 to 20% of adenocarcinomas are used [7, 9]. More recently, genomic alteration involving the anaplastic lymphoma kinase (ALK) (2p23) and the Echinoderm Microtubule associated protein Like-4 (EML4) (2p21) genes was identified in a subset of lung cancer patients having an outstanding favorable response to an ALK small molecule inhibitor (crizotinib) [7, 10-13]. The ALK-gene rearrangement was found in 1 to 7% of non-small cell lung cancers (NSCLCs) according to most of the series without KRAS and EGFR associated mutations in most of the tumors [10, 12-14]. Specific histological features characterize this subset of ALK-positive lung adenocarcinomas, presenting with a solid or acinar growth pattern, a cribriform structure, the presence of mucous cells (signet-ring cells or goblet cells), abundant extracellular mucus, a lack of lepidic growth, and a lack of significant nuclear pleomorphism [14]. Moreover, patients with tumors with ALK rearrangement were younger, were more frequently males, in most of series, and were never smokers/former light smokers [12, 14].

Circulating tumor cells (CTCs) can be isolated in more than 40% of lung cancer patients according to the series and methods [15-17]. Moreover, the prognosis of lung cancer patients, both in late and early-stages of the disease correlate to the presence and number of CTCs [15, 16]. CTCs can be isolated by different direct and indirect methods [18, 19]. Genomic alterations, particularly mutations occurring in the EGFR gene, have been demonstrated in CTCs isolated in NSCLC patients [20].

The inventors previously demonstrated that CTCs can be isolated by different methods even in early-stage disease in patients undergoing surgery for lung carcinomas [15, 21]. Moreover, the presence and number of CTCs were associated with worse prognosis [15]. Interestingly, by using a direct method that isolated the CTCs according to their size (ISET, Isolation by Size of Epithelial Tumor cells) the inventors defined malignant cytopathological criteria, which allowed good characterization of CTCs with malignant features [22, 23]. In addition, by applying an immunocytochemistry (ICC) approach to CTCs isolated by ISET from NSCLC patients our group and another group showed that a variable number of CTCs display an epithelio-mesenchymal transition (EMT) phenotype [17, 21, 24, 25].

The assessment of ALK-gene rearrangement in CTCs isolated from lung cancer patients has not been reported. This is a relevant clinical goal for non-invasive pre-screening of lung cancer patients in avoiding potential morbidity related to lung biopsy and tumor tissue removal.

Trophoblastic Rare Cells. Non-invasive methods to isolate trophoblastic cells from maternal blood have been reported, for example, as described in the U.S. Pat. No. 7,651,838 issued on Jan. 26, 2010. However, there is a need for methods of obtaining trophoblastic cells from cervical samples through a completely non-invasive and safe (e.g., without risk of inducing miscarriage) approach. Such methods should consistently recover trophoblastic cells from pregnant women in order for this approach to be useful for non invasive prenatal diagnosis of genetic defects, diseases or disorders (Imudia A N, Kumar S, Diamond M P, DeCherney A H, Armant D R. Transcervical retrieval of fetal cells in the practice of modern medicine: a review of the current literature and future direction. *Fertil Steril.* 2010: 93:1725-30). For instance, the diagnosis of fetal trisomy 21 in pregnant women can be achieved by extracting free DNA and analyzing free fetal DNA by next Generation Sequencing. If the amount of free fetal DNA is too low reliable results about the presence or absence of fetal aneuploidy cannot be obtained, thus, circulating fetal cells can be analyzed to perform the non-invasive prenatal diagnosis. U.S. Pat. No. 7,651,838 describes isolation of trophoblastic cells from blood through a noninvasive method. Trophoblastic cells could be isolated or extracted from cervical samples but it was not known how to consistently and non-invasively (without the risk of inducing miscarriage) obtain trophoblastic cells from cervical samples, from cervical mucous, or from samples obtained from mucous membrane (Imudia A N, et al *Fertil Steril.* 2010: 93:1725-30).

The inventors sought to solve the problems described above by extracting rare cells from biological samples, such as blood and mucosal secretions using filtration and the other isolation and analytic procedures disclosed herein.

BRIEF SUMMARY OF THE INVENTION

The methods disclosed herein solve these problems and challenges by using filtration as the most suitable way to extract or isolate rare cells from biological samples. After their extraction or isolation by filtration, the rare cells are present in a condition suitable for multiple or even simultaneous analytic procedures. This method effectively isolates or extracts the rare cells from a biological sample, identifies the rare cells, and then molecularly characterizes the rare cells for diagnostic purposes and to select, guide, monitor treatments and in particular to select targeted treatments and to monitor the response and/or resistance to them.

The invention comprises various modes of analyzing or characterizing rare cells. These include (i) the use of quantitative and qualitative analysis of rare cells isolated by filtration for diagnostic or theranostic purposes and to subsequently select a therapy; (ii) "qualitative analysis" includes multiple analyses performed on the same rare cells isolated by filtration. Multiple analyses on the same sample avoids problems associated with conditions in which rare cells are non-abundant or with biological samples that contain low numbers of rare cells; (iii) "qualitative analysis" including isolation of non fixed (fresh) rare cells by filtration allowing their culture and RNA analysis; (iv) use of circulating tumor cells isolated by filtration for early diagnosis of invasive cancers; and (v) use of trophoblastic cells isolated from cervical mucosal samples for non invasive prenatal diagnosis of genetic disorders In one of its aspects, the invention is a process for identifying, diagnosing, or providing a prognosis for, a condition, disorder or disease associated with rare cells comprising (a) isolating or extracting rare cells by passing a biological sample through a filter and recovering the isolated rare cells on the filter; wherein the filter has a pore size, pore density or other physical characteristics that retain rare cells but which permit passage of other kinds of cells; (b) determining the cytomorphology of the isolated or extracted rare cells, and/or immunolabeling the isolated rare cells, and/or performing molecular analysis on the isolated rare cells; (c) identifying a condition, disorder or disease and/or a stage of a condition, disorder or disease associated with the rare cells presence and/or number and/or characteristics based on the cytomorphology, and/or immunolabeling, and/or molecular analysis of the isolated or extracted rare cells. This process may be used to isolate, extract, concentrate or otherwise purify rare cells in a biological sample of interest. The biological sample may be any that contains or that is suspected of containing rare cells. These include blood or other extracellular fluids, biological fluids other than blood, such as amniotic fluid, aqueous humour and vitreous humour, bile, blood serum, blood plasma, breast milk, cerebrospinal fluid, cerumen (earwax), endolymph, perilymph, female ejaculate, gastric juice, mucous including nasal drainage, phlegm and other material collected from a mucous membrane, peritoneal fluid, pleural fluid, saliva, sebum (skin oil), semen, sweat, tears, vaginal secretion, vomit and urine. Such biological samples are preferably obtained noninvasively, however samples may also be obtained from biopsied tissues or from cellular suspensions made from solid or semisolid tissue samples.

A biological sample may be obtained from a subject of interest, such as one known to have cancer or a tumor, suspected of having cancer or a tumor, or at risk of developing a cancer or tumor. Samples may also be obtained from subjects known to have, suspected of having or at risk of developing any other condition, disorder or disease associated with or caused by rare cells, such as non-cancerous proliferative conditions, disorders or diseases. For example, a biological sample may be obtained from a subject who has an inflammatory and/or degenerative condition, disorder or disease, or who is suspected of having or at risk of having an inflammatory and/or degenerative condition, disorder or disease; from a subject who has a cardiovascular condition, disorder or disease, or who is suspected of having or at risk of having a cardiovascular condition, disorder or disease; or from a subject who has an infectious condition, disorder or disease, or who is suspected of having or at risk of having an infectious condition, disorder or disease.

In the process disclosed above in step (a) the rare cells may be isolated, extracted, concentrated or otherwise purified by passing the biological sample through a polycarbonate filter, a PET (polyethylene terephthalate, or other suitable porous filter or material and recovering the rare cells on the polycarbonate filter.

A biological sample may be fresh, such as one recently taken from a subject, a stored sample, such as preserved, refrigerated or frozen sample, or a sample subjected to another treatment such as fixation. Depending on the type of biological sample, it may be treated with a mucolytic agent, anticoagulant, protease, or by treatment with a lytic agent that selectively removes particular types of cells in the biological sample under conditions that preserve rare cells in the sample.

Prior to passage through the filter, the biological sample may be diluted or otherwise processed to facilitate the isolation, extraction, concentration or purification of the rare cells.

Rare cells that are isolated, extracted, concentrated or otherwise purified by the filtration process described herein may be transferred to a support before further analyses as in (b) or for culture.

Rare cells may be collected individually for molecular analysis after their isolation or extraction by filtration or multiple or all rare cells isolated or extracted from the biological sample by filtration may be collected for analysis in (b). Moreover, the isolated or extracted rare cells may be cultured or expanded prior to analysis in (b). For example, the rare cells may be cultured in the presence and absence of a specific drug or agent, such as a biological, chemical or radiological agent, in order to determine their response to the drug or agent compared to rare cells that were not so treated. This process may be used to select treatments targeted to rare cells isolated from a specific patient and to monitor the patient's response to a treatment or monitor development of resistance to treatment with a particular drug or agent.

Prior to analysis in (b) the isolated or extracted rare cells may be fixed or stained either in situ on the filters used to isolate them or after removal from the filters. For example, the isolated or extract rare cells may be analyzed in (b) by in situ molecular analysis after or before staining or immunostaining either on the filter or on another substrate; or (b) may comprise cytomorphological analysis of the isolated or extracted rare cells in situ on the filter or on another support to which the isolated rare cells (or subsequently cultured or multiplied rare cells) are transferred. The isolated or extracted rare cells may also be analyzed or evaluated by other methods that do not require them to be anchored to a support.

In the methods disclosed herein, (b) may comprise molecular analysis of the proteins, nucleic acids, or other components of the isolated or extracted rare cells in situ on the filter or on another substrate to which the rare cells, or cultured rare cells are applied. For example, the molecular analysis in (b) can comprise molecular analysis of the proteins, peptides or polypeptides of the isolated or extracted rare cells; the DNA, RNA, or microRNA of the isolated or extracted rare cells; or other components of the rare cells besides polypeptides or nucleic acids The processes disclosed herein may also further comprise (b1) visualizing the images of the isolated or extracted rare cells after cytomorphological analysis, immunolabeling, or in situ molecular analysis and/or (b2) recording the images of the isolated or extracted rare cells after cytomorphological analysis, immunolabeling, or in situ molecular analysis.

In another embodiment, the invention is directed to a process of detection of the presence or absence of rare cells, comprising (a) isolating, extracting, concentrating or otherwise purifying rare cells by passing a biological sample through a filter and recovering the isolated rare cells on the filter; wherein the filter has a pore size, pore density or other physical characteristics that retain rare cells but which permit passage of other kinds of cells; (b) optionally, culturing the isolated or extracted rare cells; (c) optionally, fixing or staining of the isolated or extracted rare cells or optionally cultured rare cells; (d) analyzing the isolated or extracted rare cells from (a), (b) or (c) by immunolabeling, and/or in situ molecular analysis, and/or molecular analysis of rare cells DNA, RNA, and/or microRNA, and/or molecular analysis of rare cells protein molecules. This process may use the same kinds of biological samples described above and may isolated or extract the rare cells after dilution of the biological sample or pretreatment of the biological sample as described above. The rare cells after filtration may also be fixed or used fresh or subjected to the other treatments or steps described above. In step (d), the isolated, concentrated, extracted or otherwise purified rare cells may be lysed or used intact.

When the isolated or extracted rare cells are lysed (d) can comprise detecting mutated protein(s) and/or mutated RNA and/or DNA mutation(s) associated with a condition, disorder or disease in the lysed rare cells. For example, the rare cells may be lysed to isolate polypeptides or other immunological components contained inside the rare cells, lysed in order to isolate, concentrate or otherwise purify the components to be detected, or lysed in order to isolate nucleic acids for molecular analysis.

This process may further involve selecting a targeted treatment for personalized medicine, to evaluate treatment efficacy or to detect possible resistance to treatment based on the detection of mutated DNA, and/or mutated RNA and/or mutated protein(s) in the lysed rare cells. For example, after lysis of the rare cells (d) may involve detecting the presence or absence of ALK mutations in the lysed rare cells; detecting the presence or absence of ALK mutations in the lysed rare cells, wherein said process further comprises selecting a treatment for a subject, following the efficacy of a treatment, or detecting resistance to treatment based on the presence or absence of the ALK mutation; detecting the presence or absence of a K-RAS and/or EGFR mutation in the lysed rare cells, wherein said process further comprises selecting a treatment for a subject, following the efficacy of a treatment, or detecting resistance to treatment based on the presence or absence of the K-RAS and/or EGFR mutation; or detecting the presence or absence of a B-RAF and/or HER2 mutation in the lysed rare cells, wherein said process further comprises selecting a treatment for a subject, following the efficacy of a treatment, or detecting resistance to treatment based on the presence or absence of the B-RAF and/or HER2 mutations.

The invention also contemplates a personalized medicine treatment comprising repeating the processes disclosed above using biological samples obtained from the same subject at different times. For example, rare cells samples may be isolated from a subject prior to treatment with a drug or other agent, again or several times during the course of the treatment, and again after treatment has terminated. This permits a longitudinal evaluation of the efficacy of the treatment.

Thus the biological samples are obtained from the same patient before and after treatment, at different points during treatment for a condition, or during different treatment regimens for a condition, disorder or disease associated with the rare cells. This personalized medicine treatment can also involve (e) and/or (f) that comprise further comparing the number of rare cells between samples obtained a different times to determine efficacy of a treatment regimen or to detect resistance to a treatment regimen, wherein a decrease in the relative number of rare cells detected indicates relative efficacy of a treatment regimen, and wherein an increase in the relative number of rare cells detected indicates resistance to or inefficacy of the treatment regimen; and optionally, (f) selecting an effective personalized targeted treatment for the subject based on (e).

The kind or identity or origin of the rare cells may be determined, for example, immunologically, by staining, by physical appearance, or by molecular analysis of their proteins, nucleic acids, or other components. For example, (d) may comprise analyzing the isolated or extracted rare cells comprises determining the status of epithelial to mesenchymal transition of the rare cells; may comprise analyzing the isolated or extracted rare cells comprises determining the status of stem rare cells; or may comprise analyzing the isolated or extracted rare cells by determining whether the rare cells have a gene-expression signature associated with metastatic or invasive cells or whether the rare cells express determinants associated with metastasis or invasion.

The process described herein may also further comprise making an early diagnosis of a condition, disorder or disease associated with the rare cells based on (d) or prognosing the condition. For example, the processes described above may involve making an early diagnosis of cancer and/or invasive cancer associated with the rare cells based on (d); may involve making an early diagnosis of the organ where the cancer and/or the invasive cancer originated; or may involve making an early diagnosis of an infectious condition, disorder or disease associated with the rare cells based on (d).

The processes disclosed herein may further comprise evaluating an effect of a candidate drug or candidate treatment on molecular characteristics of rare cells, and selecting a drug or treatment that reduces the number of rare cells in a subject compared to a control not given the drug or treatment, and selecting a drug or treatment that reduces the relative number of rare cells or modifies the molecular or immunological characteristics of the rare cells compared to the control.

The processes disclosed herein may also further comprise evaluating the predisposition and/or risk of a subject developing a condition, disorder or disease associated with rare cells, wherein an increase in the relative number of rare cells compared to a baseline or control value indicates a predisposition or increased risk of developing said condition, disorder or disease or wherein a molecular or immunological change in the rare cells compared to a baseline or control value indicates a predisposition or increased risk of developing said condition, disorder or disease. For example, they may comprise evaluating the predisposition and/or risk of a subject developing a genetic condition, disorder or disease; cancer, tumor or a neoplastic condition, disorder or disease; or an infectious condition, disorder or disease.

In addition to the processes and methods disclosed herein, the invention is also directed to a kit comprising at least one of one or more filters for extracting or isolating rare cells from a biological fluid, one or more buffers, diluents, or other agents for treating the biological fluid before filtration, one or more buffers for suspending, washing or otherwise treating rare cells after they are extracted or isolated from a biological fluid, one or more transfer buffers for transferring the isolated or extracted rare cells from a filter to a different support, one or more cytomorphological and/or cytochemical staining reagents or other cellular stains, or buffers therefore, one or more antibodies or other reagents for immunolabeling rare cells or buffers therefore, one or more reagents for in situ analysis of rare cells on a filter or other support, one or more lytic agents or lysis buffers for lysing rare cells, one or more antibodies or other reagents for molecular analysis of rare cell proteins, or buffers therefore, one or more probes, primers, nucleotides, enzymes or other reagents for molecular analysis of rare cell nucleic acids including PCR.

The invention also is directed to composition comprising one or more rare cells isolated, concentrated, extracted or otherwise purified by passing a biological sample through a filter and recovering the isolated rare cells on the filter; wherein the filter has a pore size, pore density or other physical characteristics that retain rare cells but which permit passage of other kinds of cells, as well as a filter or other support comprising the rare cells.

A kit comprising tools, equipment and/or reagents to accomplish both the filtration step and various kinds of multiple analyses to be performed after filtration may be assembled to facilitate the methods described above.

DETAILED DESCRIPTION OF THE INVENTION

Figure 1A:
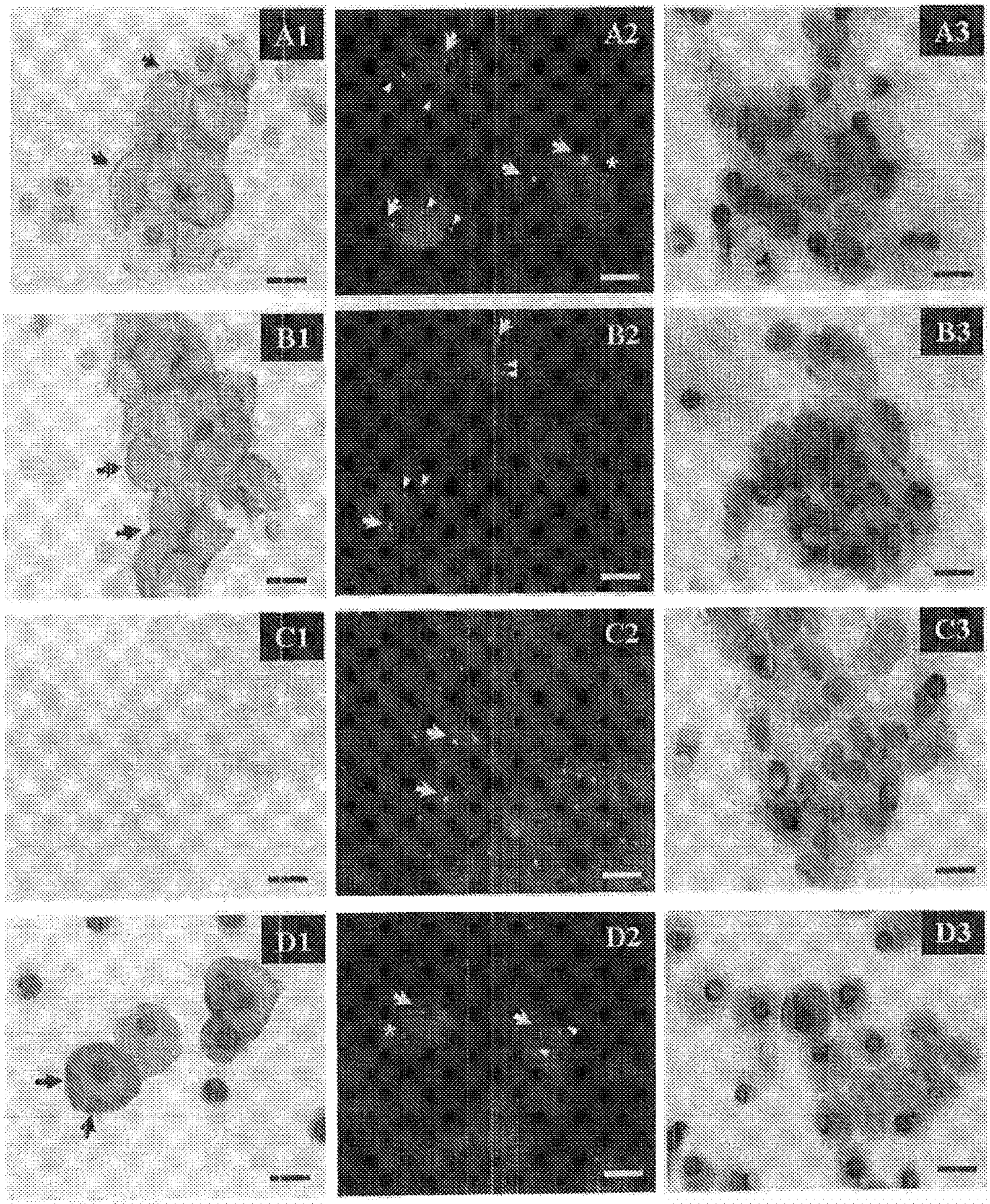
FIG. 1A. A (Case 1) and B (Case 2). A1 and B1. Circulating tumor cells showing an intense and cytoplasmic staining (score 3+) with some membrane reinforcements (arrows) (ALK immunostaining using 5A4mAb, immunoperoxidase, original magnification×1000; bar: 16 μm). A2 and B2. Circulating cell nuclei hybridized with a dual-color 2p23 LSI ALK locus-specific split probe. The two probes (3', red; 5', green) show distinct separation of the red and green signals (arrowheads) indicating a rearrangement in the 2p23 ALK gene locus. The probes give overlapping signals in nuclei without the rearrangement (arrows). Isolated 3' signals (red) are also observed (asterisks) (original magnification×1000; bar: 16 μm). A3 and B3. Circulating cells showing malignant cytomorphological criteria isolated by the ISET method (original magnification×1000; MGG staining; bar: 16 μm). C. One patient with negative FISH ALK and negative IHC ALK in tissue tumor. C1. Circulating tumor cells showing no staining (score 0) (ALK immunostaining using 5A4 mAb, immunoperoxidase, original magnification×1000; bar: 16 μm). C2. Circulating cells nuclei hybridized with a dual-color 2p23 LSI ALK locus-specific split probe. The two probes (3', red; 5', green) gave overlapping signals in nuclei without the rearrangement (arrows). No split signal was detected in these tumor cells (original magnification×1000; bar: 16 μm). C3. Circulating cells showing malignant cytomorphological criteria isolated by the ISET method (original magnification×1000; MGG staining; bar: 16 μm). D. H22213 cells isolated by the ISET method. D1 ALK immunostaining using 5A4 mAb (immunoperoxidase, original magnification×1000) showing an intense and cytoplasmic staining (score 3+) with some membrane reinforcements (arrows). D2. FISH using the dual-color 2p23 LSI ALK locus-specific split probe on the H2228 tumor cell line spiked into peripheral blood and further isolated by the ISET method. The two probes (3', red; 5', green) show distinct separation of the red and green signals (arrowheads) indicating a rearrangement in the 2p23 ALK gene locus. The probes gave overlapping signals in nuclei without the rearrangement (arrows). Isolated 3' signals (red) are also observed (asterisks)—original magnification×1000; bar: –16 μm). D3. H2228 cells stained with MGG after blood filtration (original magnification×1000; MGG staining; bar: 16 μm).

Samples. Biological samples comprise non-exclusively biological fluids comprising non-exclusively venous and arterial blood, lymph, urine, sperm, ascites, cerebrospinal fluid, pleural liquid, sputum, expectoration, nasal liquid, articular fluid, lacrymal liquid, liquid from urethra and ureter, biliary fluid, pancreatic fluid, gastric fluid, intestinal fluids, rectal fluid, vaginal fluid, samples collected non-exclusively from mucosa and organs like mouth, larynx, pharynx, uterus, cervix, vagina, esophagus, stomach, small and large intestine mucosa, samples collected non-exclusively by biopsy or other surgical intervention comprising non-exclusively samples from breast, prostate, liver, lung, bone marrow and any other organ.

Filters and Filtration. Filters that may be used to isolate or extract rare cells comprises nonexclusively a membrane of polycarbonate, PET (polyethylene terephthalate) or other material, having the thickness, and the pores size and density adapted to the extraction or isolation of defined rare cells. The filters, filtration apparatus, filtration methods, buffers and other equipment and supplies disclosed by Paterlini-Brechot in Published U.S. Patent Application US 2009/0226957 are hereby incorporated by reference.

These include (i) a method involving the use of a filter comprising at least one basic filtration zone, whereby each basic filtration zone has a limited surface area; and (ii) the surface area of each basic filtration zone and the number of basic filtration zones are selected as a function of the type of liquid to be filtered, the type of biological particles to be separated and the volume of liquid to be filtered.

Accordingly, the invention relates to a process for separating biological particles and the fluid that contains them for the purposes of purification or analysis and possibly for diagnosis, comprising at least one vertical filtration stage through a filter the porosity of which is suited to the nature of the biological particles to be separated so that said biological particles are retained by the filter, characterised in that a filter is used comprising at least one elementary filtration area, each elementary filtration area having a limited surface, and in that the surface of each elementary filtration area and the number of elementary filtration areas is chosen according to the nature of the fluid to be filtered, the nature of the biological particles to be separated and the volume of fluid to be filtered.

Each elementary filtration area of said process has a surface equal to that of a disk with a diameter of between 0.6 cm and 3 cm, and the number of elementary filtration area is chosen so that the ratio of the volume of fluid filtered to the filtration surface is less than 40 ml/cm$^2$, and preferably greater than 0.14 ml/cm$^2$.

Preferably, each elementary filtration area has a surface equal to that of a disk with a diameter greater than or equal to 0.8 cm.

Preferably, the filter has pores calibrated to a size of between 3 μm and 100 μm and a pore density of between $3\times10^3$ and $9\times10^6$ pores/cm$^2$ Preferably, filtration is carried out by a reduction in pressure of between 0.05 bar and 1 bar with, possibly, an increase in pressure of less than 1 bar.

To carry out filtration, it is preferable to use a filter forming a badge suitable to be associated with a means of analysing filtration residues by locating the elementary filtration areas.

Preferably, the badge forming the filter is incorporated in a single-use filtration module comprising at least one chamber for containing the fluid to be filtered, and that can be treated before use to sterilise it or to free it from enzymes that digest DNA, RNA or proteins.

The biological particles to be separated are, for example, cells. In this case, prior to filtering the fluid containing the cells, a sample of fluid for filtering may be prepared from a sample of fluid containing cells such as a biological fluid or cell culture by pre-enriching it with the cells to be separated and/or by diluting it.

The fluid containing the cells may be blood and, preferably, the filter in this case has calibrated pores of between 5 μm and 25 μm.

The fluid containing the biological particles is urine and the calibrated pores of the filter are between 8 μm and 100 μm.

The process can be used for the detection of cells for diagnostic purposes such as tumour, foetal, endothelial, fibroblastic, muscle, nerve or monocytal cells, cell strains, organ cells, precursors or haematopoietic cells, in a biological fluid such as blood, urine, ascites, cephalorachidian fluid, milk, pleural extravasation, fluid for washing the neck of the uterus, cell suspension fluid obtained by biopsy, by a surgical method or by mouth washing, or for the detection of animal or vegetable cells.

The invention also relates to a filtration module for implementing the process, said module comprising: a chamber block comprising at least one compartment closed at its lower portion by a base comprising at least one opening; a filter support drawer comprising at least one hole, each hole being arranged facing an opening in the chamber block; a filter gripped between the lower face of the chamber block and the support drawer.

In this module, the dimensions of each opening in the base of the chamber block and the dimensions of each hole in the filter support drawer are such that each pair made up of an opening in the base of the chamber block and the associated hole in the filter support draw, define an elementary filtration area of limited surface and in that the useful volume of each compartment is proportional to the number of elementary filtration areas situated in the base of the compartment.

Preferably, the surface of an elementary filtration area is equal to that of a disk with an equivalent diameter of between 0.6 cm and 3 cm, and the ratio of the useful volume of each compartment to the sum of the surfaces of the openings comprised in the base of the compartment is less than 40 ml/cm$^2$, and preferably greater than 0.14 ml/cm$^2$ as well as all intermediate values and subrange of the above mentioned ranges.

Preferably, the dimensions of at least one opening in the base of the chamber block and of a corresponding hole in the filter support drawer are such that the surface of the corresponding elementary filtration area is greater than or equal to that of a disk 0.8 cm in diameter.

Preferably, at least one compartment may be divided into part compartments by at least one removable separation wall, such that at least one part compartment comprises in its base at least one opening and that the ratio of the volume of said part compartment to the sum of the surfaces of the openings in the base of the part compartment is less than 40 ml/cm$^2$, and preferably greater than 0.14 ml/cm$^2$ as well as all intermediate values and subrange of the above mentioned ranges.

Preferably, the filtration module comprises a grooved sealing joint arranged between the base of the chamber block and the filter, comprising at least one hole corresponding to a hole in the base of the chamber block, the hole being surrounded by at least one projecting lip.

In addition, the filtration module preferably also comprises a plate joint between the filter and the filter support, comprising at least one opening opposite a hole in the filter support.

The filter may form a badge the central portion of which comprises at least one porous area and the periphery of which forms a frame comprising means for indexing its position on the filter support.

The indexation means are, for example, at least two holes of different diameter designed to cooperate with studs of corresponding diameter provided on the filter support.

Preferably, at least a central porous portion of the filter comprises between $3\times10^3$ and $9\times10^6$ pores per $cm^2$ of between 3 μm and 100 μm. All intermediate pore size values and subranges are contemplated within this range including 3, 4, 5, 6, 7, 8, 9, 10, 11, 12, 13, 14, 15, 16, 17, 18, 19, 20, 25, 27.5, 30, 35, 40, 45, 50, 55, 60, 70, 75, 80, 85, 87.5, 90, 92.5, 95, 97.5 and 100 μm. All intermediate pore density ranges and subranges are also contemplated 1, 2, 3, 4, 5, 6, 7, 8, or $9\times10^3$, $10^4$, 1, 2, 3, 4, 5, 6, 7, 8, or $9\times10^4$, $10^5$, 1, 2, 3, 4, 5, 6, 7, 8, or $9\times10^5$, $10^6$ and 1, 2, 3, 4, 5, 6, 7, 8, or $9\times10^6$ pores/$cm^2$.

Preferably, the filtration module also comprises at least one stopper for closing the upper opening of a compartment.

Preferably, the chamber block comprises, at its lower portion, a rim extending outwards and cooperating with at least one assembly pin allowing the filter to be gripped between the filter support and the chamber block, the assembly pin comprising a breakable end extending above the rim of the chamber block.

Preferably, all its parts are made of materials suited to a sterilisation operation or designed to render them free from RNases, DNases or proteinases.

Finally, the invention relates to a filtration module support for retaining a filtration module on a filtration machine, comprising at least one cam that can move between an open position and a gripping position, designed to put pressure on the filter between the filter support and the chamber block.

Preferably, at least one cam is designed so that, if the filtration module comprises at least one fixing pin one end of which is breakable, the end of at least one fixing pin is cut when pressure is applied to the filter by at least one cam.

The support block forms part of a filtration machine.

Preferably, the filtration module also comprises a means designed to cooperate with a complementary means on a support block, so as to impose the orientation of the filtration module in relation to the support block, and the support block comprises a means designed to cooperate with a means on a filtration module, so as to index the orientation of the filtration module in relation to the support block.

The method for isolating biological particles contained in a fluid, according to the invention, consists of filtering the fluid on a filter with characteristics suited to the nature of the particles to be isolated. The biological particles may be cells, red blood cells, platelet aggregates, fibrins or tissue waste. The filtered fluid is in particular a fluid obtained from a sample of biological fluid that may have undergone prior treatment to facilitate the isolation by filtering operation. This prior operation, which will be described in more detail later, comprises in general, particularly when the particles to be isolated are cells, one or a plurality of the following operations: chemical treatment designed to pre-enrich the cell to be isolated, dilution, chemical treatment designed to facilitate separation by filtration of the cells to be isolated.

As well as these conditions for preparing samples of fluid for filtering, the inventors noted that to achieve good reliability in the process of isolating cells to be detected, it was necessary to adapt certain characteristics of the filter to the volume of fluid filtered. In particular, the filter must be divided into elementary filtration area each having a surface equal to that of a disk of diameter of between 0.6 cm and 3 cm, and preferably greater than 0.8 cm and even better between 0.8 cm and 1.5 cm as well as all intermediate values and subrange of the above mentioned ranges. The elementary filtration areas may be in the shape of a disk, for example.

In addition, the quantity of fluid to be filtered, which must pass through each of the elementary filtration areas, must be between 1 ml and 100 ml, and preferably this volume should be between 8 ml and 15 ml. These ranges include all intermediate values and subranges of the above mentioned ranges.

Thus, to filter a particular sample a device must be used to define a number of elementary filtration areas on the filter in proportion to the volume of the sample to be filtered.

In general, the volume of the sample to be filtered depends on the one hand on the volume of biological fluid that could be taken initially, and on the other hand on a possible dilution which depends in particular on the nature of the biological particles to be separated. The volume taken depends in particular on the nature of the fluid taken and the age of the patient from whom the fluid is taken. A person skilled in the art knows how to determine the volumes to be taken depending on the nature of the fluid taken and on the patient from whom it is taken.

Dilution depends in particular on the number of particles per unit of volume that can be found in the fluid taken. Indeed, if filtration is to be carried out under satisfactory conditions, the number of particles to be isolated per unit of volume of fluid to be filtered should not be too great to avoid clogging the filter. Moreover, if the process is intended to detect particular rare cells mixed with a far greater number of cells, the number of cells per unit of volume should not be too small, so as to achieve a reasonable probability of finding the cells sought on the filter. A person skilled in the art also knows how to determine these dilution rates depending on the nature of the fluid in question and the type of cell sought.

The biological sample taken from a patient may, for example, be blood, urine, ascites, cephalorachidian fluid, milk or pleural extravasation; it may also be fluid from washing the neck of the uterus or any other fluid that may result from taking a biological sample from a patient.

The analysis method may also be used to search for cells in samples that have not been taken directly from patients, and for example, in samples taken in cell culture mediums made from smears or biopsies or from human or animal tissue samples or, further, in human or animal cell line culture mediums.

If the biological fluid taken is blood, the amount taken is generally between 1 ml and 20 ml, and the blood is diluted by a ratio that varies from 1 in 5 to 1 in 20 to obtain a sample of fluid for filtering which, in these conditions, is filtered over one to 20 elementary filtration areas. These values include all intermediate values and subrange of the above mentioned ranges.

For all other fluids, the samples are approximately 5 ml to 10 ml and are diluted in a ratio of between 1 in 2 and 1 in 10, or they may not be diluted. These samples are filtered over a number of elementary filtration areas which may be as many as 5 or even more, particularly if it is a 10 ml sample that has been diluted in a ratio of 1 in 10. These values include all intermediate values and subrange of the above mentioned ranges.

The cells that may be sought are in particular rare cells such as tumour cells, foetal cells, endothelial cells, fibroblastic cells, muscle cells, nerve cells, monocrystal cells, cell strains, organ cells (hepatic, renal, etc. . . . ), precursors and haematopoietic cells. This list, which is given as an example, is not limitative.

Before filtration, the cells may be pre-enriched by treatment of the density gradient type or by lysis of cells that are of no interest, or by immunomediated methods, by positive or negative screening, by stimulating the cells sought to proliferate, etc.

This list is not limitative, and a person skilled in the art knows how to choose a pre-enrichment process suited to the nature of the cells that he or she seeks to isolate.

As well as the pre-enrichment treatment, the fluid sample containing cells may be treated by a reagent according to the nature of the cells sought, to facilitate the separation by filtration operation.

The aim of the treatment may be to lyse red blood cells and anticoagulate the blood if the biological sample contains blood, and consists, for example, of adding saponin and EDTA.

The aim of the treatment may also be to fix nucleated cells, for example by the addition of formaldehyde, if the filtration is intended to isolate fixed cells. In this case, the object of the treatment is to make enrichment possible.

If the filtration is intended to isolate non-fixed cells, the biological sample may be treated with a reagent and under conditions suitable for temporarily rendering biological membranes rigid (for example, by the addition of polysaccharide, DMSO, by cold, etc.).

A person skilled in the art knows how to choose the most suitable method, according to the nature of the cells sought.

The biological sample which may have been diluted, pre-enriched or treated with a reagent to allow filtration suited to the end sought, is then filtered through a filter made of polycarbonate or an equivalent material that has calibrated pores of a size between 1 μm and 100 μm and suited to the nature of the particles to be separated. All intermediate values and subranges are contemplated within this range including 1, 2, 3, 4, 5, 6, 7, 8, 9, 10, 11, 12, 13, 14, 15, 16, 17, 18, 19, 20, 25, 27.5, 30, 35, 40, 45, 50, 55, 60, 70, 75, 80, 85, 87.5, 90, 92.5, 95, 97.5 and 100 μm. This size is preferably between 3 μm and 25 μm, and is about 8 μm, for example, particularly if tumour cells or epithelial cells are to be isolated.

Pore density is suited to the nature of the particles to be separated. Preferably, the pore density of the filter is between $5\times10^3$ and $5\times10^6$ pores/cm$^2$ and even better between $5\times10^4$ and $5\times10^5$ pores/cm$^2$. All intermediate values and subranges within these ranges are contemplated as well as the following specific values: 1, 2, 3, 4, 5, 6, 7, 8, or $9\times10^3$, $10^4$, 1, 2, 3, 4, 5, 6, 7, 8, or $9\times10^4$, $10^5$, 1, 2, 3, 4, 5, 6, 7, 8, or $9\times10^5$, $10^6$ and 1, 2, 3, 4, 5, 6, 7, 8, or $9\times10^6$ pores/cm$^2$.

Filtration is performed preferably be a reduction in pressure of between 0.05 bar and 1 bar, and preferably of approximately 0.1 bar. All intermediate values and subranges of this range are contemplated including 0.05, 0.06, 0.07, 0.08, 0.09, 0.10, 0.20, 0.30, 0.40, 0.50, 0.60, 0.70, 0.80, 0.90 and 1.0 bar. Filtration may be assisted by a slight increase in pressure on the fluid situated above the filter. This increase in pressure must however be less than 1 bar. These conditions are particularly suited to cell separation.

The process may be used for different objectives, for example to search for rare cells in suspension in a biological fluid, so as to allow diagnosis or to purify a fluid to allow analysis in good conditions of the elements in solution.

If the process is used to search for cells and analyse them, after filtration, the filter that has been used to filter the fluid is recovered ensuring that the filtration areas are clearly identified and that a link can be made between these filtration areas and the sample that was filtered. The filter is then used to analyse the cells that it may have been possible to recover in the filtration areas.

These analysis methods, which are known per se, are for example of the following types: cytological staining (haematoxylin, eosin, etc.), immunomarking (immunohistochemistry, immunofluorescence) PNA, FISH, PRINS, PCR in situ or other molecular technique, spectrophotometry, laser microdissection followed by targeted molecular analyses on the DNA (DNA extraction, genotyping, quantitative PCR, mutation analysis, CGH (comparative genomic hybridisation)) RNA (extraction and analysis by PCR of transcripts, quantitative PCR) and proteins (protein extraction, microsequencing, etc.).

The molecular analyses may be performed on enriched cells held on the filter and transposed onto a slide by a technique similar to the Southern technique, individually microdissected from the filter or from the slide according to defined criteria (morphological characteristics of the cells with or without marking of different natures) and subjected to individual or pooled molecular analysis.

The cells may also be detached from the filter by washing with an appropriate buffer to extract and analyse their DNA, RNA and proteins.

The elements isolated by filtration are then examined with a microscope and analysis of the images obtained on the filter may be carried out manually or by automated means, in particular by using image analysis equipment.

The process may also be used to purify a biological fluid such as urine containing in solution the DNA, RNA or proteins that are to be analysed. The purpose of purifying the fluid is to eliminate all the biological particles present in the fluid, which could interfere with the analysis. In this case, the filters are not kept and it is the filtered fluid that is analysed.

This filtration method and the sample preparation and analysis methods may be used as stated previously in particular for the purpose of diagnosis to detect pathologies associated with the presence of particular cells possibly in extremely small quantities. In particular, the process can be used to detect cancerous cells that may have been released into a patient's blood during a surgical operation. A person skilled in the art knows what cells can be searched for to detect a particular pathology.

Support. A support may represent a solid non porous support such as a slide or a petri dish or a culture well or any other support made of glass or plastic or any solid material which can be used as a support of cells for culture, treatment or analyses of any type: cytomorphological, immunolabelling, in situ molecular analyses, comprising protein, RNA or DNA analyses, and collection of cells for molecular analyses, comprising protein, RNA or DNA analyses.

Filtration. Filtration of a biological sample to extract, isolate, purify or concentrate rare cells, is carried out by using non-exclusively a membrane of polycarbonate, PET (polyethylene terephthalate) or other material, having the size and density of pores adapted to the extraction or isolation of defined rare cells and by using depression applied under the filter to isolate or extract rare cells.

Extraction of cells by vertical filtration of a biological sample allows one to layer them and make them available for further analyses, such as for detection and characterization and diagnosis of rare cells. Isolation of cells by vertical filtration of a biological sample allows one to isolate rare cells away from smaller cells in order to enrich them and make them available for further analyses, such as for detection, characterization, and/or diagnosis of rare cells. Typically isolation of rare cells by filtration of blood allows to separate the majority of neutrophils and mature lymphocytes and erythrocytes (erythrocytes do not contain nucleus, thus they are not considered true cells and are generally lysed before filtration) which are the smallest cells in the body as their size is 6 to 9 microns, and to retain on the filter cells larger than neutrophils and mature lymphocytes including activated lymphocytes, monocytes, macrophages, stem cells, tumor cells, cancer cells, tumor microemboli, mature and immature endothelial cells, epithelial cells, mesenchymal cells other than neutrophils and mature lymphocytes, melanocytes myeloblasts, promyelocytes, megakaryoblasts, megakaryocytes and in general all the cells of the body which are not neutrophils and mature lymphocytes. Furthermore, isolation of rare cells by filtration of blood also allows one to collect, on the other side of the filter, plasma and leukocytes or other components of a biological sample distinct from the rare cells isolated by filtration. Plasma contains free DNA and RNA, and proteins including free tumor DNA and tumor RNA, and tumor microRNA and proteins in patients with cancer, and including free fetal DNA, fetal RNA and fetal micro RNA and proteins in pregnant women. The term "free" indicates "outside cells", thus free nucleic acids in plasma. Free tumor DNA is used for diagnosis of tumor mutations in patients with cancer and free fetal DNA is used for prenatal diagnosis of aneuploidies and other genetic disorders, fetal gender, RhD status, paternity tests. Collecting leukocytes at the same time as rare cells and plasma can be useful to analyze and obtain information about the genetic background of the individual. Free tumor DNA and/or RNA and/or protein is expected to derive from lysed, probably apoptotic, tumor cells from the tumor mass and/or tumor metastases and/or circulating tumor cells compartment. Analysis of free tumor DNA and/or RNA and/or proteins is performed by extracting DNA and/or RNA and/or proteins from plasma and looking for mutations by molecular analyses. For instance, a quick analysis of the presence of K-Ras mutations in patients with lung cancer can be performed by extracting free DNA from plasma and looking for mutated K-Ras molecules by PCR, CastPCR, Cold PCR, digital PCR and other targeted molecular tests. Thus, analysis of K-Ras mutations in circulating tumor cells can be associated to the analysis of KRas mutation in plasma DNA. In addition, the study may start with the search of KRas mutation in plasma, which is less expensive, and if the mutation is not found, it may go on with the search of KRas mutation in circulating tumor cells, which is more expensive.

The diagnosis of fetal gender is done easily and at low cost by analysis of plasma DNA. However, if the amount of free fetal DNA in plasma is low, a negative signal with Y specific molecular analyses does not allow obtaining reliable results. In this case, the possibility to add the analysis, more expensive, of circulating fetal cells, will allow obtaining a reliable diagnosis of fetal gender.

The detection of infectious diseases, like those caused by HBV, HCV, or HIV or by bacteria or other pathogens, can be performed by extracting molecules such as DNA, and/or RNA, and/or micro RNA and/or proteins from plasma and looking for the presence of viral or bacterial or other pathogens DNA, and/or RNA, and/or micro RNA and/or proteins by molecular analyses. As a complementary test, DNA, and/or RNA, and/or micro RNA and/or proteins specific to pathogens can be looked for in circulating rare cells.

In specific cases, it can also be useful to obtain at the same time information on mutated or infectious molecules in rare cells, mutated or infectious molecules in plasma, and on the genomic characteristic of the individual. In this case, the collection of plasma and leukocytes after filtration to isolate circulating rare cells is extremely useful. For instance, in infected patients, it can be useful to look for infectious molecules, such as DNA from TBC *bacillum*, in circulating rare cells, in plasma and to look for genetic susceptibility traits in the leukocytes. For instance, in patients with cancer of genetic origin, it will be useful to look for a mutation, such as BRCA1 or BRCA2, in the circulating tumor cells, in plasma and in the leukocytes. For instance, in pregnant women, it can be useful to analyze rare circulating fetal cells for the presence of Duchenne's disease, a genetic disease that affects only male fetuses, to look for Y sequences in the free fetal DNA to know if the fetus is male and to look for the carrier status in the maternal leukocytes. For instance, in pregnant women, it can be useful to analyze rare circulating fetal cells for the presence of Huntington's disease, a dominant genetic disease that may have a late onset, to look for Huntington's mutated sequences in the free fetal DNA, and to look for the presence of Huntington's mutation in the maternal leukocytes. In fact, since the mutation is dominant, the presence of the mutation in one of the two parents gives the fetus 50% risk to be affected. If the genetic analysis discovers that the fetus is affected, it will be useful to check if the mutation was carried by the mother through analysis of maternal leukocytes.

These examples are not exclusive. In general, the possibility to isolate circulating rare cells and at the same time to collect plasma and leukocytes for immediate analysis or for storage and future analysis has a high potential and value in non-invasive personalized medicine.

Adaptation of the size of the pores of the filter to the biological samples to be filtered allows one to selectively isolate cells of discriminate size, for instance, tumor microemboli and syncytiotrophoblasts, groups of cells and multinucleated cells, and cellular material having a larger size than individual cells, thus efficiently isolating such material from blood or other fluids with high purity (low or absent contamination by leukocytes and other smaller cells) by filtration using pores larger than 20-25 microns in diameter, thus eliminating by filtration all leukocytes and erythrocytes.

By analogy, by studying the particular size of tumor cells of a given tumor type and/or in a given patient, and/or by studying the particular size of certain rare cells to be isolated, it is possible to adapt the pore size, pore density and other chemical or physical features of the filter to maximize recovery and purity of the isolated tumor and/or rare cells. For instance, fetal cells size may vary from 10 to 30 microns. Syncytiotrophoblasts size is generally larger than 100 microns. The size of mature endothelial cells, which are not round but elongated cells, is around 40 or 50 microns per 10 to 20 microns. Thus, the pores size range of interest is between 5 microns and 30 microns and the larger pores size allows eliminating all the leukocytes. In fact, the larger leukocytes, which are macrophages and monocytes, have a size that generally is not larger than 20 microns. The size of the pores has to be adapted very closely to the pores density, and be in a range from 0.5 to 2.0 E5 pores per cm2 as enough filter material has to be between pores to allow collection of rare cells.

Tumor cell size. Tumor cells by definition are not "resting cells" as they produce proteins and may proliferate, thus their chromatin is open and never compacted like the chromatin of mature leukocytes as mature lymphocytes and mature neutrophils which are the majority leukocytes (as number) and are thus smaller than tumor cells. Individual tumor cells size may vary from 10 micron to 50 microns or more depending on the type of tumor cells. Ex size of Tumor cells from Small Cell Lung Carcinoma (SCLC): 1.5 to 3 times the size of lymphocytes (12 to 24 microns), size of Tumor cells from Non-Small Cell Lung Carcinoma (NSCLC): over 3 times the size of lymphocyte (24 microns). Tumor microemboli size is generally larger than 100 microns.

Advantages of filtration. Extraction or isolation of rare cells by filtration has several advantages, over other methods of extraction/isolation:

It permits isolation of rare cells with very high sensitivity, including collection of one individual rare cell that can be spiked before filtration in one ml of blood, thus mixed with several millions of leukocytes and several billions of erythrocytes.

It allows extraction or isolation of rare cells independently from the antigens expressed by rare cells, thus avoiding bias of isolation leading to the loss of rare cells.

It facilitates the multi-analyses of rare cells, including morphological, immunolabelling, in situ molecular analyses and molecular analyses without interference of other non rare cells.

It allows one to modulate the purity of the isolated rare cells, which make easier their multi-analyses, including morphological, immunolabelling, in situ molecular analyses and molecular analyses without interference of other non rare cells.

It allows one to collect rare cells individually, as single cells or groups of single cells, or as cells mixed with residual non rare cells for further molecular analyses.

It speeds up the detection and counting the rare cells by getting rid of the millions of small leukocytes and billions of erythrocytes It allows one to extract or isolate fixed or fresh cells for further analyses.

Other modes of filtration. Various modes filtration may be employed so long as they permit rare cells to be isolated from other kinds of cells and/or layered on the filter for further analysis. For example, the force for separating rare cells from other kinds of cells that pass through a filter may be gravity, positive or negative pressure, or centrifugal force.

Pretreatment of Samples. Biological samples can be diluted and/or treated before and/or after filtration by agents used to lyse erythrocytes like saponin, ammonium chloride, lytic antibodies, hypotonic solutions, anticoagulants like EDTA, heparin, coumadin and other Vitamin K antagonists, factor Xa antagonists, thrombin inhibitors; aspirin (salicylic acid) and other agents preventing platelet aggregation, mucolytic drugs, and fixative agents (see below).

Rare cells extracted or isolated from biological samples by filtration can be fixed cells or fresh cells. Fixed or fresh rare cells extracted or isolated from biological samples by filtration can be transferred to a support comprising non-exclusively slide, petri dish, well or microwell or test tube or other support for analysis, molecular analyses or culture. Transfer of cells from the filter to a support can be obtained by using collecting and/or detaching means and/or buffers. For instance, in order to transfer all cells from the filter to a slide or to a solid support and avoid loosing rare cells, it is possible to use commercially available adhesive slides such as SuperFrost Ultra Plus® slides or Clearcell™ and Adcell™ BioAdhesion Slides and/or to treat the filter before filtration with agents which prevent sticking of cells to the filter with siliconizing agents like Sigmacote™ or similar. In order to transfer all the cells collected on the filter to a slide or to any other support and to avoid loosing rare cells it is also possible to help the transfer with solutions to be applied to the back of the filter, thus the side which does not stick to cells, and creating a flux of buffer through the pores toward the solid surface which will detach cells from the filter so that they can adhere to the slide or other solid support. This process of transfer of cells and rare cells collected on a filter to a slide or other solid support can also be improved by using positive air and/or liquid pressure applied to the back of the filter: air and/or liquid will pass through the pores and help cells to be transferred to the slide or other solid support. All these protocols to detach cells and rare cells from the filter and transfer them to a slide or solid support will work better if cells on the filter are not dried, thus if the transfer is performed soon after filtration.

Extraction or isolation of fixed cells by filtration is performed by fixing them before filtration using fixative agents comprising non-exclusively formaldehyde, paraformaldehyde, glutaraldehyde, RCL2, mercurials like B5 and Zenker's fixative, methyl alcohol and ethyl alcohol, picrates like Bouin's solution, Rigaud fixative etc.

Fresh rare cells extracted or isolated from biological samples by filtration can be fixed after filtration using fixative agents comprising non-exclusively formaldehyde, paraformaldehyde, glutaraldehyde, RCL2, mercurials like B5 and Zenker's fixative, methyl alcohol and ethyl alcohol, picrates like Bouin's solution, Rigaud fixative etc.

Culture of Rare Cells. Rare cells extracted or isolated from biological samples can be cultured in order to increase their number and facilitate their detection and/or diagnosis and/or characterization. The culture protocol may include means to stimulate preferentially the growth or rare cells versus the growth of non rare cells in order to increase the purity of rare cells. Means to stimulate preferentially the growth or rare cells versus the growth of non rare cells comprise non-exclusively specific growth factors and/or agents stimulating the growth of rare cells, co-culture of rare cells with other cell types and/or use of feeder layers helping the growth of rare cells, and means to block the growth and/or survival of non rare cells such as inhibiting antibodies, blockers of cell cycle, proapoptotic factors, siRNA, and drugs of any type specifically targeting non rare cells in order to obtain the block of their growth and/or their elimination.

Characterization of Rare Cells. Rare cells detection and/or diagnosis and/or characterization can be obtained through cytomorphological and/or immunolabelling and/or molecular analyses. Cytomorphological and/or immunolabelling analyses are performed in situ on intact cells, i.e., on cells which plasma membrane and/or cytoplasmic limit and/or nuclear limit is recognizable.

Cytomorphological analyses non-exclusively comprise staining by Hematoxylin and/or Eosin, May Grunwald and/or Giemsa staining, Papanicolau staining, Feulgen staining and all type of staining and stochiometric staining aiming to analyze cellular morphological details and analyze and/or quantify cellular components. Cytomorphological analyses non-exclusively comprise cytochemical analyses which non-exclusively comprise PAS, Sudan, Alcian blue staining, enzymatic and non-enzymatic methods able to reveal cellular components which non-exclusively comprise calcium, lipids, polysaccharides, enzymes and others molecules.

Immunolabeling non-exclusively comprises labeling cellular components with antibodies which non-exclusively comprise antibodies directed to epithelial antigens, to mesenchymal antigens, to organ-specific antigens, to tumor-specific antigens, to fetal-specific antigens, to stem cells-specific antigens, to transcription factors, to mutated proteins and to any protein and/or peptide and/or cellular component which detection may help cellular identification and/or diagnosis and/or characterization. Immunolabeling also non-exclusively comprises immunocytochemistry, immunofluorescence, immune-PCR, and all types of labeling of cellular structure through antibodies bound to a mean used to reveal the immunological link and the cellular target.

Molecular analyses comprising non-exclusively FISH (Fluorescence In Situ Hybridization), PRINS (Primed In Situ labeling)), TUNEL (Terminal deoxynucleotidyl transferase dUTP nick end labeling), immunoPCR, PNA (peptide nucleic acid), in situ PCR and other methods using non-exclusively molecular probes can be performed in situ on intact cells.

Image analyses of rare cells after in situ staining and/or immunolabelling and/or in situ molecular analyses can be performed and images can be stored and/or transferred informatically before further rare cells molecular analyses implying cellular lysis.

Molecular analyses comprising non-exclusively PCR, Reverse Transcriptase-PCR, real time PCR, digital PCR, Whole Genomic Amplification, sequencing, High Throughput sequencing, Cast-PCR, Cold PCR, Comparative Genomic Hybridization (CGH), CGH array, microarray analyses, methylation analyses, polymorphism analyses, etc. can be performed on cells which structure has been disrupted and/or lysed in order to analyze molecular components comprising non-exclusively DNA, RNA, microRNA and protein molecules.

Molecular analyses comprising non-exclusively PCR, Reverse Transcriptase-PCR, real time PCR, digital PCR, Whole Genomic Amplification, sequencing, High Throughput sequencing, Cast-PCR, Cold PCR, Comparative Genomic Hybridization (CGH), CGH array, microarray analyses, methylation analyses, polymorphism analyses, etc. can be targeted to individual cells, or to groups of individual cells or to all cells extracted or isolated through filtration from a biological sample.

Targeted analyses to individual cells or groups of cells identified according to morphological criteria and/or immunolabelling can be performed by using laser microdissection of the filter part containing the cells of interest, or of cells after transfer to a support, followed by lysis of cellular proteins and molecular analysis of cellular DNA (genomic and/or mitochondrial DNA), RNA, microRNA and protein molecules. Alternatively, rare cells extracted or isolated by filtration can be detached from the filter and individual cells or groups of cells identified according to morphological criteria and/or immunolabelling can be isolated by magnetic field (Silicon biosystem or other methods based on magnetic field), or by manual or automated capillary micropipetting. Alternatively, all cells extracted or isolated by filtration can be lysed on the filter, or after transfer to a support, by using an appropriated buffer in order to perform their DNA (genomic and/or mitochondrial DNA), RNA, microRNA or protein molecular analysis by using non-exclusively PCR, Reverse Transcriptase-PCR, real time PCR, digital PCR, Whole Genomic Amplification, sequencing, High Throughput sequencing, Cast-PCR, Cold PCR, Comparative Genomic Hybridization (CGH), CGH array, microarray, methylation analyses, polymorphism analyses, etc.

Non-invasive Theranostics. Among its other aspects, the invention makes it possible to isolate circulating tumor cells from blood and use them for non-invasive theranostics. Theranostics is the use of a diagnostic result to guide prescription of a specific "targeted" treatment. These procedures take advantage of a particular molecular biomarker that may be present in tumor cells to predict their susceptibility to respond or not a given therapy. As cancer therapies are costly and often toxic, theranostic is thus important to minimize health care cost and burden due to adverse effects to patients. Theranostics biomarkers are now looked for in the primary tumor and metastases tissues. However, it has been demonstrated that tumor cells in the primary tumor are genetically heterogeneous and biopsies can miss tumor cell clusters carrying genetic information useful to set up optimal targeted treatments. Metastases are considered to be a better reference, but their biopsy is difficult to obtain. Indeed, the physical conditions of cancer patients often prevent to obtain samples from the primary tumor or metastases through an invasive approach (surgery or biopsy) due to the high rate of morbidity linked to these invasive procedures. Moreover, tumor cells genetic characteristics may change under pressure of targeted treatment making important to follow them during treatment in order to detect new "tumor cells mutants" escaping targeted treatments. However, an invasive follow up of cancer cells genetics characteristics is unfeasible in clinical settings due to the related morbidity. Finally, it would be useful to study non-invasively the genetic characteristics of tumor cells in certain patients in order to apply targeted therapies preoperatively on the purpose to decrease the tumor burden before the intervention and better remove the tumor.

Targeted therapies are now available for a number of common cancers (breast cancer, lung cancers, colorectal cancer etc. . . . ) and have shown their efficacy in a proportion of cases. However, in the absence of demonstrated predictive factors of tumor response, these targeted expensive therapies will either be prescribed to the great majority of patients, with a huge increase of related costs without proportional benefit, or will not be prescribed, preventing patients from taking benefit from them.

The implementation of theranostic biomarkers is thus expected to lead to impressive therapeutic improvements. However, theranostic analyses addressed to tumor tissues (primary tumor, metastases) imply invasive (surgical or semi-surgical) procedures that cannot be performed in debilitated patients, are very costly, and often provide incomplete data. Consequently, the analysis of tumor cells and tumor microemboli obtained non-invasively is of utmost importance in clinical oncology.

Genetic Characterization of Rare Cells. Information on the genetic characteristics of tumor cells can be obtained non-invasively from circulating tumor cells (CTC), circulating tumor microemboli (CTM), and tumor cells collected from biological fluids (urines, ascites, sperm, cerebrospinal fluid (CSF), sputum, expectoration etc).

Methods to study genetic characteristics of tumor cells vary according to the genetic abnormalities to be detected. They can rely on cytological, cytochemical, immunocytochemical analysis, FISH, PRINS, immunoPCR, DNA and RNA extraction and analyses targeted to genes or sequences of interest and/or to the whole exome or the whole genome/transcriptome sequence.

Several theranostic biomarkers have been validated in particular for Non-Small Cell Lung Carcinoma (NSCLC) and colon cancer. Epidermal growth factor receptor (EGFR) is a membrane receptor tyrosine kinase. Overexpression or overactivity of EGFR is found in many cancers. EGFR mutations are detected in 10% to 15% of all patients with NSCLC and in 80% of patients who clinically respond to EGFR tyrosine kinase inhibitors such as gefitinib (AstraZeneca) or erlotinib (Roche). Known EGFR mutations include mutations located in exons 18 to 21 of the EGFR tyrosine kinase domain. These mutations are well described in particular in lung cancer. Patients having a primary tumor with the L858R mutation or the deletion of exon 19 mutation have a better response to EGFR inhibitors than patients with wild-type KRAS tumors[13]. The L858R mutation and the deletion of exon 19 mutation are among the most frequent EGFR mutation in lung tumors with a frequency of approximately 43% and 48% of all EGFR mutations, respectively (hypertext_transfer_protocol://world_wide_web.mycancergenome.org, accessed May 21, 2013).

KRAS (also known as V-Ki-ras2 Kirsten rat sarcoma viral oncogene homolog) encodes a 21 kDa GTPase localized to the inner membrane. This protein is a core component of the signal transduction pathway upstream of EGFR. KRAS mutations occur in 15-25% of lung adenocarcinoma (hypertext_transfer_protocol://world_wide_web.mycancergenome.org, accessed May 21, 2013). KRAS more frequent mutations results in a constitutive activation of KRAS kinase activity. Point mutations occur in codon 12 (82% of all KRAS mutations) and 13 (17% of all KRAS mutations) in exon 2 of the KRAS gene. Standard sequencing detects in one test of all codon 12 and 13 mutations (G12C: c34G>T, G12R: c34G>C, G12A: c35G>C, G12D: c35G>A, G12V: c35G>A, G12S: c34G>A, G13C: c37G>T, G13D: c38G>A).

Wild-type KRAS is required for EGFR inhibitor efficacy in NSCLC patients [13]. Wild-type KRAS is also required for efficacy of anti-EGFR therapeutic antibodies (Eli Lilly, Bristol-Myers Squibb, Merck Serono) in patients with metastatic colorectal cancer [14,15]. Mutations in codons 61 and 146 have also been reported but they represent a minor proportion of KRAS mutations (1-4%) and their clinical relevance remains obscure [15].

Currently, NSCLC patients with KRAS mutations have no effective treatment strategy. Ganetespib (Synta Pharmaceuticals) is a small molecule inhibitor of the chaperone Hsp90 that is currently ongoing a Phase III clinical trial. A phase 2 trial showed tumor shrinkage in more than 60 percent of patients with KRAS-mutant NSCLC at eight weeks after treatment with ganetespib administered once weekly as a monotherapy (International Association for the Study of Lung Cancer, 14th World Conference on Lung Cancer).

More recently, a genomic alteration involving the anaplastic lymphoma kinase (ALK) (2p23) and the Echinoderm Microtubule associated protein Like-4 (EML4) (2p21) genes was identified in a subset of lung cancer patients. These patients have an outstanding favorable response to an ALK small molecule inhibitor, Crizotinib (Pfizer) [16,17, 18,19]. In fact, Crizotinib is currently tested in a phase III clinical trial and the preliminary results of the phase II trial evidenced an impressive 90% disease control rate in ALK rearranged lung tumors [20]. This rearrangement has been found in 1 to 7% of NSCLC according to most of series, particularly in late stage adenocarcinomas, without EGFR and KRAS associated mutations [21].

Two other outstanding theranostic biomarkers have been validated in other types of cancer. Human Epidermal Growth Factor Receptor-2 (HER2) is a cell membrane surface-bound receptor tyrosine kinase and is normally involved in the signal transduction pathways leading to cell growth and differentiation. The HER2 locus is amplified in 20-30% of breast tumors and the presence of this amplification is an indication of tumor response to the targeted therapy trastuzumab (anti-HER2, Roche) [22].

Zelboraf (Roche) is a very effective drug that has been recently approved by the Food and Drug Administration (FDA) for the treatment of patients with melanoma whose tumors harbor the V-raf murine sarcoma viral oncogene homolog B1 (BRAF) gene V600E mutation. As this mutation is also present in 1% of lung cancer patients, lung cancer patients may become eligible for this drug in the future. Other theranostic biomarkers validated or ongoing clinical trials include:

Breast and ovarian cancer: ER, PR, BRCA1, BRCA2

Gastrointestinal cancer: c-Kit, CDC4, p53

Non-small cell lung cancer: ROS1, HER2, FGFR, PDGFRA, VEGFR, PI3K

MTOR, MEK, STAT3, AKT, RET fusions

Prostate Cancer: recombination TMPRSS2/ERG.

Concerning non-invasive theranostic analyses of tumor cells, current unsolved issues addressed by the present invention are the following:

Tumor cells have to be extracted or isolated from biologic samples in a very sensitive manner, to avoid their loss, and with maximum purity, i.e. with the minimum of contaminating non tumor cells (to avoid false negative results obtained by molecular analyses).

Furthermore, tumor cells obtained noninvasively are a rare, low-represented material; still, they need to be the target of several analyses and molecular analyses in order to be used as a non-invasive theranostic test. These unsolved issues prevent the development and widespread application of non-invasive theranostic tests in clinical oncology. The present invention describes a solution to the problems mentioned above through the process involving the following steps:

(i) Filtration of the biologic sample by using a membrane which characteristics of material (polycarbonate, PET, etc), thickness, pores size and pores density are specifically tailored to the type and number of tumor cells to be isolated and to the biological liquid to be treated to isolate non-invasively tumor cells and tumor microemboli.

(ii) Staining/Labeling the isolated cells by cytological staining, immunostaining, FISH, Tunel, PRINS, immunoPCR, and any type of analyses performed without cell lysis as a theranostic test (iii) Image analysis of the stained/labeled cells including scanning and High Density record of cell images. Images can be analyzed for diagnostic purposes, stored and/or transferred informatically to specialists helping in the diagnostic process.

(iv) Tumor cells-targeted lysis of fresh or fixed cells collected noninvasively. The targeted approach includes a Laser Capture Microdissection (LCM) step. LCM allows isolation of single tumor cells (or cluster of tumor cells) after isolation by filtration. This method allows addressing genetic analysis to pure tumor DNA. As tumor cells are heterogeneous and are mixed with normal cells (in tissues, as well as on filters), LCM is currently an available method to evaluate the percentage of mutant CTCs among the population of CTCs. Alternative to LCM are micromanipulation systems, DEP Array (Silicon Biosystem) or CellCelector (ALS). After lysis, cells undergo DNA and/or RNA and/or protein analyses.

(v) Non-targeted lysis of all fixed or fresh cells extracted or isolated by filtration for their molecular (RNA, DNA and/or proteins) analyses comprising molecular analyses targeting mutated sequences mixed with non mutated sequences (cold PCR, Cast PCR etc.)

(vi) Theranostic molecular analyses addressed to RNA, DNA and/or proteins targeted to one or several biomarkers or applied to the whole exomic or genomic sequence.

The advantages of this strategy are the following:

(a) Optimized approach to isolate rare cells from biological samples with maximum sensitivity and purity and absence of bias of selection of rare cells that could derive from immunolabelling-based and/or marker-based capture systems.

(b) Possibility to perform several diagnostic and/or prognostic and/or theranostic analyses on the same rare cells collected noninvasively. For instance, in patients with Lung cancer, it will be possible to obtain from the same tumor cells collected noninvasively the results of ALK analysis (FISH) and of KRAS and EGFR molecular analysis (DNA analyses after cell lysis). For instance, in patients with infectious diseases, it will be possible to obtain, from cells of the immune system such as activated lymphocytes or monocytes and macrophages, results of FISH analyses specific to intracellular viruses (HIV, etc) or microbiological agents (*Shigella*, TBC *bacillum, Leishmania*, etc.) and results of DNA and/or RNA and/or protein analysis specific to the infectious agent.

For instance, in pregnant women, it will be possible to obtain non invasively, from the isolated rare fetal cells, results of cytopathological and/or immunolabelling and/or in situ molecular analyses (FISH or PRINS with Y specific probes) in order to diagnose the presence of male fetal cells and to obtain the DNA and/or RNA and/or protein mutation analysis performed on lysed cells which demonstrate the presence or absence of mutated molecules, thus the presence or absence of fetal genetic disorders.

(c) Possibility to obtain diagnostic and/or prognostic and/or theranostic information of the presence, or absence, and number of tumor cells or other rare cells extracted or isolated by filtration and to store images of cytopathological and/or immunolabelling and/or in situ molecular analyses before proceeding to the cells lysis which allows to obtain diagnostic and/or prognostic and/or theranostic information about the presence, or absence of DNA and/or RNA and/or protein mutations and about the presence, or absence of pathological DNA and/or RNA and/or protein molecules in the rare cells of the analyzed biological sample.

For instance, in patients with cancer, it will be possible to obtain from the same tumor cells collected non invasively the stored images of the results of cytopathological and/or immunolabelling and/or in situ molecular analyses in order to diagnose the presence of tumor cells and characterize them by in situ immunological and in situ molecular analyses and to obtain the DNA and/or RNA and/or protein mutation analysis performed on lysed cells.

For instance, in patients with infectious diseases, it will be possible to obtain non invasively, from the isolated rare cells, the stored images of the results of cytopathological and/or immunolabelling and/or in situ molecular analyses in order to diagnose the presence of infected cells and characterize them by in situ immunological and in situ molecular analyses, and to obtain the DNA and/or RNA and/or protein analysis from lysed cells which will demonstrate the presence or absence of molecules of the infectious agents, thus the presence or absence and number of infectious agents.

For instance, in pregnant women, it will be possible to obtain non invasively, from the isolated rare fetal cells, the stored images of the results of cytopathological and/or immunolabelling and/or in situ molecular analyses in order to diagnose the presence of fetal cells and characterize them by in situ immunological and in situ molecular analyses, and to obtain the DNA and/or RNA and/or protein mutation analysis performed on lysed cells which demonstrate the presence or absence of mutated molecules, thus the presence or absence of fetal genetic disorders.

These advantages are not provided at present by any process targeting rare cells and comprising processes for non-invasive theranostic analyses.

EXAMPLES

Example 1: Multianalysis of Fresh, Non-Fixed, Tumor Cells Enriched from Blood by Filtration Filtration. Fresh tumor cells were extracted and enriched from blood by filtration as described in published patent application US-2009-0226957.

The extracted, non-fixed cells were stained to determine their morphology and their nucleic acids are extracted and analyzed by RT-PCR or PCR after whole genomic amplification.

To extract and enrich rare tumor cells from blood, a blood sample is diluted 20-fold using a buffer for red blood cell lysis. Lysis is allowed to proceed for 5 minutes at room temperature with a gentle agitation.

The treated blood sample is then immediately filtered at a depression of −6 mBar. Filtration is stopped before it is totally complete in a way that about 200 μL of solution remains in the well.

The enriched fresh tumor cell material is collected by gently pipetting 3 times 1 mL of cell culture media (DMEM HEPES 1% Fetal Calf Serum).

The collected material is then centrifuged at 1000 rpm for 5 minutes and the supernatant carefully removed. The pellet is resuspended in cell culture media.

The extracted cells can then be cultured using DMEM 10% Fetal Calf Serum. The extracted or cultured cells can then be used to perform functional assays, such as to test for secreted proteins, in proliferation assays or in adhesion assays.

Individual tumor cells can be isolated (i) using a (micro) pipette under a microscope based on a simple cell size criteria or immunolabeling; or (ii) using the cell sorter such as the DEParray (Silicon Biosystems).

After isolating a single cell, the molecular analysis of the nucleic acids at the DNA and/or the RNA level can proceed.

DNA Analysis. For DNA analysis of fresh single cells, the cell is lysed for 15 minutes using 3-10 μL of lysis buffer (100 mmol/L Tris-HCl, pH 8; 400 μg/mL proteinase K). Proteinase K is inactivated at 94° C. for 15 min.

Alternatively, the cell can be lysed using a thermostable proteinase such as prepGem (ZyGem) and its associated buffer (Gold buffer) for 5 min at 75° C. followed by inactivation for 5 min at 95° C. Downstream processing of the DNA from a fresh single cell is identical the one of fixed microdissected cells described in the example X.

RNA Analysis. For RNA analysis, fresh or fixed cells or a fresh or fixed single cell is lysed in a buffer containing 400 mM Tris-HCl pH 8, 1000 μg/mL proteinase K and 2.5 U of RNAase Inhibitor. For reverse transcription, the RNA from the lysed cell is denatured for 10 min at 70° C. Reverse transcription is performed in a total volume of 40 μL using 10 units of MMLV, 10 units of inhibitor, Random primers, dNTPs and 1× concentration of the reverse transcription buffer supplied with the enzyme. The reaction is typically incubated for 15 minutes at room temperature and 30 minutes at 42° C. Enzyme are then inactivated for 10 minutes at 70° C. and chilled on ice before transcript-specific amplification by PCR or whole cDNA amplification using a commercial kit (Life Technologies, Illumina).

In a specific example, ALK gene recombination can be detected using Taqman assays (hs03654556, Hs03654557, Hs03654558, Hs03654560, Hs03654559, Life technologies) or by standard PCR. the detection of the EML4-ALK recombination transcript variants 3a and b, the following primers can be used:

```
Forward primer:
                                       (SEQ ID NO: 1)
5'-GCATAAAGATGTCATCATCAACCAAG-3'

Reverse primer:
                                       (SEQ ID NO: 2)
5'-TCTTGCCAGCAAAGCAGTAGTTGG-3'
```

Tumor cells are identified by multiplex immunolabeling using antibodies against epithelial marker and/or antibodies against proteins important for theranostic (HER2, ALK etc.). Molecular analysis targeted to circulating tumor cells are allowed after single-cell laser capture microdissection (LCM) using a Nikon TE 2000 U (Nikon Paris, France) equipped with a cell cut module (MMI, Zurich, Switzerland).

Each microdissected cell can be lysed in 2 to 15 μL of lysis buffer (100 mmol/L Tris-HCl, pH 8; 400 μg/mL proteinase K). Proteinase K is inactivated at 94° C. for 15 min. Alternatively, the cell can be lysed using a thermostable proteinase such as prepGem (ZyGem) and its associated buffer (Gold buffer) for 15 min at 75° C. followed by inactivation for 5 min at 95° C.

WGA can be performed using Primer Extension Preamplification (PEP) or commercial kits (Rubicon Genomics, Sigma, Qiagen, Silicon Biosystems).

For primer extension preamplification (PEP) 5 μL of a 400 μM solution of random primers (genPEP), 10 μL of 10×PCR buffer containing 15 mM $MgCl_2$ (Life technologies), 0.6 μL of a mixture of four dNTPs (each at 2 mM) and 1 μL (5 U) of Taq polymerase (Life technologies) in a final volume of 60 μL, are added to the lysed cell.

For WGA using PicoPlex from Rubicon Genomics, 5 μL of preamplification cocktail is first added to the lysed cell (total volume 15 μL) and preamplification is performed according to the manufacturer's instructions.

Then, 60 μL of amplification cocktail is added and amplification performed according to the manufacturer instructions. WGA products may be purified using the Zymo Research D4014 kit according to the manufacturer instruction.

Gene-specific amplifications are performed in 60 μL containing 6 μL 10 mM Tris-HCl, 50 mM KCl, 1.5 to 2.5 mM $MgCl_2$, 200 μM of each deoxynucleotide, 0.5 μL of primer and 2 U of Taq Gold (Life technologies). Two microliters of PCRouter product were re-amplified in 20 μL using 'inner' gene-specific primers and the same PCR protocol.

Using WGA products from PicoPlex, nested PCR may not be necessary for all genes. Furthermore, these WGA products are compatible with high-throughput sequencing and CGH microarrays analysis Primer sequences and cycling conditions are indicated in the following Table 1:

TABLE 1

Primer sequences and cycling conditions

| Primer | Sequence | Specific conditions |
|---|---|---|
| KRAS OUT Forward | AAAAGGTACTGGTGGAGTATTTGA (SEQ ID NO: 3) | Annealing at 58° C. for 30 seconds 2 mM $MgCl_2$ |
| KRAS OUT Reverse | TCATGAAAATGGTCAGAGAAACC (SEQ ID NO: 4) | |
| KRAS IN Forward | GTATTAACCTTATGTGTGACA (SEQ ID NO: 5) | Annealing at 58° C. for 30 seconds 2 mM $MgCl_2$ |
| KRAS IN Reverse | GTCCTGCACCAGTAATATGC (SEQ ID NO: 6) | |
| BRAF-OUT Forward | TTAGATCTCTTACCTAAACTCTTCA (SEQ ID NO: 7) | Annealing at 55° C. for 30 seconds 2.5 mM $MgCl_2$ |
| BRAF-OUT Reverse | TCAGGGCCAAAAATTTAATCA (SEQ ID NO: 8) | |
| BRAF-IN Forward | TGCTTGCTCTGATAGGAAAATG (SEQ ID NO: 9) | Annealing at 60° C. for 30 seconds 2.2 mM $MgCl_2$ |
| BRAF-IN Reverse | CCACAAAATGGATCCAGACA (SEQ ID NO: 10) | |
| EGFR-exon 19- forward | TGC CAG TTA ACG TCT TCC TT (SEQ ID NO: 11) | Annealing at 61° C. for 30 seconds 2.2 mM $MgCl_2$ |
| EGFR-exon 19- reverse | CAG GGT CTA GAG CAG AGC AG (SEQ ID NO: 12) | |
| EGFR-exon 20- forward | CAT TCA TGC GTC TTC ACC TG (SEQ ID NO: 13) | Annealing at 55° C. for 30 seconds 2.2 mM $MgCl_2$ |
| EGFR-exon 20- reverse | TTA TCT CCC CTC CCC GTA TC (SEQ ID NO: 14) | |
| EGFR-exon 21- forward | CTT CCC ATG ATG ATC TGT CC (SEQ ID NO: 15) | Annealing at 60° C. for 30 seconds 2.2 mM $MgCl_2$ |

TABLE 1-continued

| Primer | Sequence | Specific conditions |
|---|---|---|
| Primer sequences and cycling conditions | | |
| EGFR-exon 21- reverse | GCTGCGAGCTGACCCAGAATGTC TGG (SEQ ID NO: 16) | |
| VHL-exon 1- part 1-forward | GCGCGTTCCATCCTCTAC (SEQ ID NO: 17) | Annealing at 55° C. for 30 seconds 2.5 mM $MgCl_2$ |
| VHL-exon 1- part 1-reverse | GGCCTCCATCTCCTCCTC (SEQ ID NO: 18) | |
| VHL-exon 1- part 2-forward | GAGTACGGCCCTGAAGAAGA (SEQ ID NO: 19) | Annealing by touch down (65-60° C.) for 30 seconds 2.5 mM $MgCl_2$ |
| VHL-exon 1- part 2-reverse | CCGTCGAAGTTGAGCCATAC (SEQ ID NO: 20) | |
| VHL-exon 1- part 3-forward | GCCGAGGAGGAGATGGAG (SEQ ID NO: 21) | Annealing at 54°C. for 30 seconds 2.5 mM $MgCl_2$ |
| VHL-exon 1- part 3-reverse | GCTTCAGACCGTGCTATCGT (SEQ ID NO: 22) | |
| VHL-exon 2- forward | ACCGGTGTGGCTCTTTAACA (SEQ ID NO: 23) | Annealing at 56° C. for 30 seconds 2.5 mM $MgCl_2$ |
| VHL-exon 2- reverse | TCCTGTACTTACCACAACAACCTT (SEQ ID NO: 24) | |
| VHL-exon 3- forward | GCCACTGAGGATTTGGTTTT (SEQ ID NO: 25) | Annealing at 58° C. for 30 seconds 2.5 mM $MgCl_2$ |
| VHL-exon 3- reverse | CAAAAGCTGAGATGAAACAGTG (SEQ ID NO: 26) | |

After gene-specific PCR, the mutational status of the gene is determined using traditional sequencing, fragment analysis, SNP assays (Taqman assays), COLD-PCR, cast-PCR, or HRM analysis.

Molecular analysis can also be performed without laser-capture microdissection after lysis of all the cells present on a filtration spot. Rare cell enrichment and purity can be improved using filters with pores size and pore density adapted to increase purity of defined rare cells.

Tumor cell DNA mixed with wild-type DNA from leucocytes is collected after protein lysis in a volume of at least 45 μL. The extracted DNA can be split into several WGA reactions or purified and used for one WGA reaction.

As for single cells, WGA can be performed using Primer Extension Preamplication (PEP) or commercial kits (Rubicon Genomics, Sigma, Qiagen, Silicon Biosystems).

After WGA, sensitive gene mutation-specific assays can be used to assess the presence of mutated DNA among non-mutated DNA. This can be achieved using different methods such as digital PCR, COLD-PCR or cast-PCR.

In the case of Cast-PCR, 2 μL of purified WGA DNA (about 20 ng of DNA) can be used in a typical 20 μL cast reaction.

Example 2: Genetic Characterization of Circulating Tumor Cells and Detection of a Theranostic Mutation in the Circulating Tumor Cells Lung Cancer. According to a preferred mode of implementation, rare cells can be isolated from blood of patients with lung cancer by filtration, tumor cells can be identified among the isolated rare cells by cytomorphological analyses and characterized by ALK specific antibodies and molecular probes.

ALK-gene rearrangement, a comparative analysis on circulating tumor cells and tumor tissue from lung adenocarcinoma patients The aim of this work described below as 1) to assess the ALK status in CTCs having malignant cytopathological criteria isolated by ISET in 87 patients with lung adenocarcinomas and, 2) to compare the ALK status found in CTCs and in the corresponding tumor tissue. For this purpose, an assay based on a dual immunochemical and FISH approach for ALK-gene rearrangement was used and applied to both CTCs and corresponding tumor tissue samples.

Patients and Samples

In a previous study using the ISET method for patients undergoing surgery for NSCLC, CTCs having cytomorphological malignant features were detected in 76/208 (37%) of cases [15].

For the present work the inventors selected from this latter population 40 cases with a primary adenocarcinoma. In addition, 47 lung adenocarcinoma patients included in the study between May and December 2011 had CTCs with malignant features. Among these 87 patients, 34 had blood samples (10 ml) collected and treated by ISET by using a fixating buffer (containing a cell fixative agent) and as described in published patent application US 2009-0226957 at different times: before surgery, and at 7 and 15 days after surgery. All patients gave their informed consent to participate in this study. The main clinicopathological features of the selected 87 patients are summarized in Table 2.

TABLE 2

| Clinical and pathological parameters | Nb of patients (%) |
|---|---|
| Main clinicopathological data of the 87 cases included in this study | |
| Overall | 65 (100) |
| Age (years) | |
| Mean | 66 |
| Range | 37-85 |

TABLE 2-continued

Main clinicopathological data of the 87 cases included in this study

| Clinical and pathological parameters | Nb of patients (%) |
|---|---|
| Gender | |
| Male | 41 (63) |
| Female | 24 (37) |
| Tobacco exposure (PY) | |
| Number | 53 (81) |
| Average | 38.2 |
| Range | 0-152 |
| Tumor size (cm) | |
| Mean | 3.9 |
| Range | 0.4-18 |
| Histology | |
| Invasive adenocarcinoma (ADC) | 65 (100) |
| Acinar predominant ADC | 33 (51) |
| Papillary predominant ADC | 21 (32) |
| Micropapillary predominant ADC | 4 (6) |
| Lepidic predominant ADC | 4 (6) |
| Solid predominant ADC with mucin production | 3 (5) |
| Number of CTCs | |
| >50 CNHC-MF (range 51-500) | 28 (43) |
| <50 CNHC-MF (range 14-49) | 37 (57) |
| pTNM Staging | |
| I | 30 (46) |
| IA | 12 |
| IB | 18 |
| II | 16 (25) |
| IIA | 9 |
| IIB | 7 |
| III | 14 (21) |
| IIIA | 12 |
| IIIB | 2 |
| IV | 5 (8) |
| TTF1 antigen expression | 44 (67) |
| Neoadjuvant therapy | 14 (21) |

TNM: tumor node metastasis
PY: packs year
CNHC-MF: circulating non hematological cells with malignant features.

Tumors were classified according to the $7^{th}$ pTNM classification and to the last histological classification of lung adenocarcinomas [26, 27]. FISH analysis was performed on the tumor samples using a break-apart probe for the ALK gene (Vysis LSI ALK Dual Color, Abbott Molecular, Abbott Park, IL) (Supplementary Data). To be adequately interpreted, tumor cell nuclei should have at least one colocalisation signal. To be considered as ALK-rearranged, at least 15% of interpretable tumor cell nuclei should harbor an abnormal probe hybridization pattern [28]. Immunohistochemistry (IHC) was performed on deparaffinised sections using a primary antibody against the ALK protein (1:50, 5A4; Abcam, Cambridge, UK) incubated for 45 minutes at room temperature (Supplementary Data). Targeted mutation analysis for, i) EGFR mutation hot spots, ii) KRAS mutation hot spots, and iii) BRAF mutations, was performed from DNA extracted from frozen tumor tissue sections by pyrosequencing, as previously described [29, 30] (Supplementary Data).

Immunocytochemistry (ICC) and Fluorescence In Situ Hybridization (FISH) on ISET Filters.

ICC and FISH were performed on CTCs isolated by the ISET method on unstained spots of the corresponding filters containing CTCs with malignant features detected by MGG staining on 6 spots [15]. Two spots were used for ICC and two spots were used for FISH per filter. For ICC, the spots were incubated with a primary antibody against the ALK protein (1:50, 5A4; Abcam, Cambridge, UK) for 30 minutes at room temperature. The reactions were visualized with 3,3'-diaminobenzidine, followed by counterstaining with hematoxylin. Cytoplasmic staining was considered positive for ALK (Supplementary Data). FISH performed on two or more spots used a break-apart probe for the ALK gene (Vysis LSI ALK Dual Color, Abbott Molecular, Abbott Park, IL) in accordance with the manufacturer's instructions. Cells showing split signals or alone 3' signals were considered positive for ALK rearrangement [31]. Filters were examined independently and blinded to clinical, IHC, ICC data and tissue genotype. We tested the reproducibility of the ICC and FISH results for ALK detection on CTCs of 102 filters of 34 patients who underwent blood sampling before surgery, and 7 and 15 days after surgery.

14 to 500 interpretable tumor cell nuclei were analyzed for each patient. To be correctly interpreted, tumor cell nuclei should have at least one colocalisation signal. To be considered as ALK-rearranged, at least 15% of interpretable tumor cell nuclei should harbor an abnormal probes hybridization pattern.

Human NSCLC cell line H2228 obtained from ATCC (Manassas, VA) were used as an ALK rearrangement positive control [32]. Cells were cultured and maintained in RPMI 1640 medium supplemented with 10% fetal bovine serum, as previously described [32]. Around 50 cells were mixed into 10 ml of a blood sample taken from healthy volunteers. Samples were then filtered using the ISET method, as described previously [23]. FISH using a break-apart probe and ICC with anti-ALK antibodies were then performed as described above.

Positive ALK immunostaining was found in five tumors corresponding to adenocarcinomas with a solid predominant structure with mucin production. These five cases showed strong positive cytoplasmic staining (score 3+) for all tumor cells as defined previously, with membrane reinforcement in a couple of cells [31]. FISH analysis performed on the same paraffin block on serial sections, demonstrated ALK-rearranged adenocarcinomas. The other 82 tumors were negative for ALK immunostaining and for ALK-rearrangement using FISH analysis. Ten tumors (12%) were EGFR mutated (1 exon 18, 6 exon 19, and 3 exon 21 mutations) and 20 cases (24%) were KRAS mutated (18 codon 12 of exon 2 and 2 codon 13 of exon 2). The BRAF mutation was not detected. The five ALK-rearranged tumors were EGFR, KRAS and BRAF wild-type.

Figure 1B:
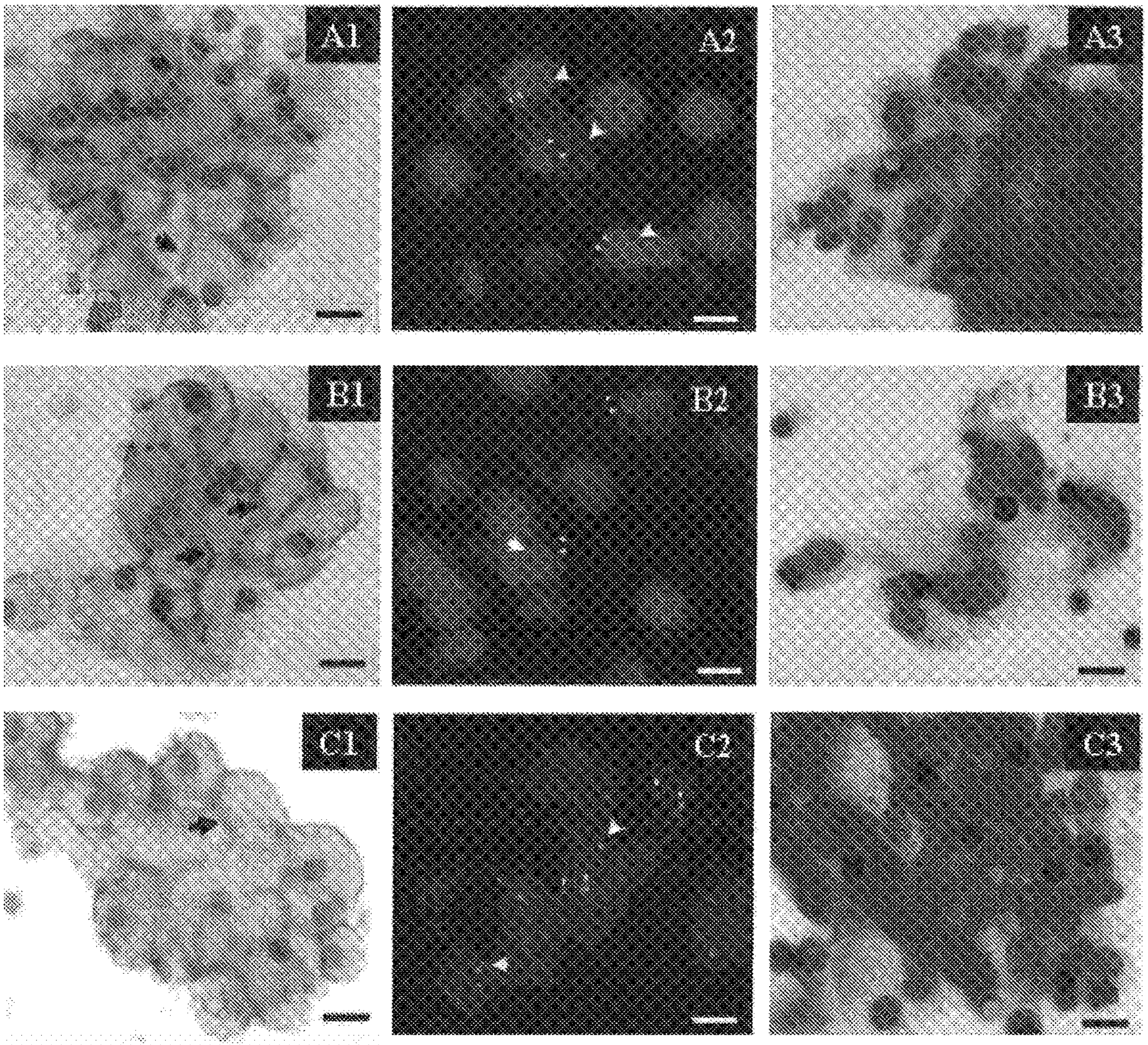
FIG. 1B. A (Case 3), B (Case 4) and C (Case 5). A1-C1. Circulating tumor cells showing an intense and cytoplasmic staining (score 3+) with some membrane reinforcements (arrows) (ALK immunostaining using 5A4mAb, immunoperoxidase, original magnification×1000; bar: 16 μm). A2-C2. Circulating cell nuclei hybridized with a dual-color 2p23 LSI ALK locus-specific split probe. The two probes (3', red; 5', green) show distinct separation of the red and green signals (arrowheads) indicating a rearrangement in the 2p23 ALK gene locus. The probes give overlapping signals in nuclei without the rearrangement (arrows). Isolated 3' signals (red) are also observed (asterisks) (original magnification×1000; bar: 16 μm). A3-C3. Circulating cells showing malignant cytomorphological criteria isolated by the ISET method (original magnification×1000; MGG staining; bar: 16 μm).

Positive ALK immunostaining was found in CTCs isolated in five patients, corresponding to the patients having ALK-rearrangement in tumors (FIG. 1A, A1 and B1, and FIG. 1B). The clinicopathological data of these five patients are detailed in Table 3.

TABLE 3

Clinicopathological data of the cases with FISH ALK-gene rearrangement and positive immunocytochemistry using an anti-ALK antibody in CTCs isolated by Isolation by Size of Epithelial Tumor cells (ISET) method.

| CASE NUMBER | 1 | 2 | 3 | 4 | 5 |
|---|---|---|---|---|---|
| Sex | Male | Male | Female | Male | Female |
| Age | 45 years | 48 years | 47 years | 52 years | 43 years |
| Smoking status | Never smoked | Never smoked | Never smoked | Never smoked | Never smoked |
| Ethnicity | Caucasian | Caucasian | Caucasian | Caucasian | Caucasian |
| pTNM stage | IIA | IIA | IIIB | IV | IV |
| Histology | Adenocarcinoma with solid architecture | Adenocarcinoma with solid architecture | Adenocarcinoma with solid architecture | Adenocarcinoma with solid architecture | Adenocarcinoma with solid architecture |
| Status for EGFR, KRAS, BRAF mutations | Wild-type | Wild-type | Wild-type | Wild-type | Wild-type |
| ALK FISH (tumor) | Positive (40% of cells) | Positive (50% of cells) | Positive (60% of cells) | Positive (40% of cells) | Positive (50% of cells) |
| ALK IHC (tumor) | Positive (100% of cells) | Positive (100% of cells) | Positive (100% of cells) | Positive (100% of cells) | Positive (100% of cells) |
| Number of CNHC-MF | ≥50 cells (70-90 cells) | ≥50 cells (60-150 cells) | ≥50 cells (70-100 cells) | ≥50 cells (60-100 cells) | ≥50 cells (80-120 cells) |
| ALK FISH (CTCs) | Positive (100% of cells) | Positive (100% of cells) | Positive (100% of cells) | Positive (100% of cells) | Positive (100% of cells) |
| ALK ICC (CTCs) | Positive (100% of cells) | Positive (100% of cells) | Positive (100% of cells) | Positive (100% of cells) | Positive (100% of cells) |
| Follow-up (5 years) | Alive (no relapse) | Alive (no relapse) | Deceased | Deceased | Deceased |

Abbreviations:
FNM = tumour node metastasis;
CNHC-MF: circulating non hematological cells with malignant The anti-ALK ICC using the 5A4 clone showed strong cytoplasmic staining (score 3+) of 100% of the CTCs with membrane reinforcements in most of the cells (FIG. 1, A1 and B1, and FIG. 1B). ALK FISH was informative in these five cases (FIG. 1, A2 and B2, and FIG. 1B). All CTCs had abnormal signal patterns with at least 3 signals observed per cell in each case, consistent with either gene amplification or aneusomy (FIG. 1, A2 and B2, and FIG. 1B). Moreover, FISH confirmed the presence of an ALK translocation, all cases having break apart of 5' and 3' probes and multiple signals per cells (FIG. 1, A2 and B2, and FIG. 1B). None of the five cases had loss of either part of the FISH probe. Finally, for these five patients, CTCs stained with MGG showed CTCs with malignant features, as described previously (FIG. 1, A3 and B3, and FIG. 1B) [22]. The positivity of ALK-ICC and ALK-FISH were controlled for each patient with CNHC-MF isolated using ISET at 7 and 15 days after the first detection.

No positive immunostaining with the anti-ALK antibody and no ALK-rearrangement using FISH analysis were demonstrated in the 82 others selected lung cancer patients showing CTCs with malignant features on MGG staining (FIG. 1, C1-C3). ALK-rearranged H2228 cells diluted in blood samples, than filtered by the ISET method demonstrated strong positive ALK immunostaining and ALK translocation (FIG. 1, D1-D3).

The reproducibility of the results for detection of ALK by ICC and FISH was tested on CTCs of 102 filters of blood samples from 34 patients who underwent blood sampling before surgery, and 7 and 15 days after surgery. Of the 34 patients included, 5 patients had ALK positive tumor tissue and 29 patients had ALK negative tumor tissue. Positive results were consistently obtained by ICC and FISH for CTC from the three different blood samples obtained from each of the 5 patients with ALK positive tumors. Negative results for ALK were consistently obtained by ICC and FISH on CTC from the three different blood samples obtained from each of the 29 patients with ALK negative tumors.

Supplementary Data: Patients and Samples

FISH analysis was performed on the tumor samples using a break-apart probe for the ALK gene (Vysis LSI ALK Dual Color, Abbott Molecular, Abbott Park, IL) (Supplementary Data). Slides were read (MI, EL, CB) on an epifluorescence microscope (BX51, Olympus, Tokyo, Japan) using a 63× objective and the images were analyzed using Soft Imaging system (Cell, Olympus) software. Results were independently assessed blinded to clinical and immunohistochemical data and genotype. When a discrepancy between the three pathologists was noted, the slides were reviewed in order to obtain a consensus. At least 50 interpretable tumor cell nuclei were analyzed for each tumor. To be adequately interpreted, tumor cell nuclei should have at least one colocalisation signal.

Immunohistochemistry (IHC) was performed on deparaffinised sections using a primary antibody against the ALK protein (1:50, 5A4; Abcam, Cambridge, UK) incubated for 45 minutes at room temperature. The intensity of staining as well as percentages of positive cells were assessed semi-quantitatively as follows: 0=no or faint staining in <10% of tumor cells; 1+=faint staining in >10% of tumor cells; 2+=moderate staining; 3+=strong staining. Positive ALK expression was considered as between 1+ and 3+. Immunohistochemical staining in specimens was independently assessed by three pathologists (MI, VH and PH) blinded to the clinical data and genotype. When a discrepancy between the three pathologists was noted, the slides were reviewed in order to obtain a consensus.

Targeted mutation analysis for, i) EGFR mutation hot spots in codons 719, 768, 790, and 858-861, as well as deletions and complex mutations in exon 19, ii) KRAS mutation hot spots in codons 12, 13 and 61, and iii) BRAF mutations in codons 600 and 464-469, was performed from DNA extracted from frozen tumor tissue sections by pyrosequencing, as previously described [29, 30]. PCR amplification was performed using the corresponding Therascreen® Pyro kits (Therascreen® EGFR Pyro® kit, CE-IVD, Ref. 971480; Therascreen® KRAS Pyro® kit, CE-IVD, Ref. 971460; Therascreen® BRAF Pyro® kit, CE-IVD, Ref. 971470; Qiagen, Hilden, Germany) following the manufacturer's protocols. PCR products (10 μl) were processed in a 24-well format for pyrosequencing analysis using the PyroMark Q24 MDx Vacuum Workstation (Qiagen), following the standard manufacturer's protocol. The plate was transferred directly to the PyroMark Q24 System (Qiagen) for sequence determination. Data were automatically analyzed with PyroMark Q24 Software (Qiagen).

Supplementary Data: Immunocytochemistry (ICC) and Fluorescence In Situ Hybridization (FISH) on ISET Filters For ICC, heat-induced epitope retrieval was performed with a targeted retrieval solution (pH 9) (Dako, Carpinteria, CA) for ALK. The spots were treated with 3% hydrogen peroxide for 20 minutes to block endogenous peroxidase activity, followed by washing in deionised water for 2-4 minutes. The spots were then incubated with a primary antibody against the ALK protein (1:50, 5A4; Abcam, Cambridge, UK) for 30 minutes at room temperature. The reactions were visualized with 3,3'-diaminobenzidine, followed by counterstaining with hematoxylin. Cytoplasmic staining was considered positive for ALK [30]. The intensity of staining as well as percentages of positive cells was evaluated by three pathologists (MI, VH and PH) semi-quantitatively as described above. Filters were examined independently and blinded to clinical, IHC data, and the tissue and cell genotype. When a discrepancy between the three pathologists was noted, the slides were reviewed in order to obtain a consensus.

The inventors have shown, using a dual ICC-FISH assay, that the ALK status can be detected non-invasively in CTCs characterized by a cytomorphological approach in a subset of lung cancer patients. Moreover, these results demonstrated a strict correlation between the ALK status determined in CTCs and in the corresponding tumor tissue samples in a series of 87 lung adenocarcinoma patients. Five of these patients had clinicopathological characteristics previously reported to be associated with ALK-gene rearrangement in the Western population and showed ALK-gene rearrangement both in CTCs and in corresponding resected tumor samples [28]. Conversely, CTCs with an ALK-gene rearrangement were never found in patients with a tumor without ALK-gene rearrangement, as demonstrated by FISH Recent studies focused their interest on the relevance for prognosis of ALK-positive lung cancer patients, independently of ALK targeted therapy [33-35]. Some of these studies demonstrated that in patients not treated with pre-ALK inhibitors, ALK-positive patients had a shortest survival, and were associated with a higher risk of metastasis [33, 35]. Moreover, ALK-positive patients were more resistant to EGFR tyrosine kinase inhibitor treatment than ALK-negative patients [33]. Conversely a recent study demonstrated that wild-type EGFR ALK-positive lung adenocarcinoma patients had a better outcome [34]. In the present work, the 5-years follow-up of the five EGFR wild-type ALK positive patients showed no recurrence for the two stage II patients who underwent surgery, whereas the three stage IIIb/IV patients died within 6 months after the diagnosis. No adjuvant therapy, in particular no targeted therapy against ALK rearrangement was administered in these patients.

A non-invasive assay to detect ALK-gene rearrangement through CTCs isolation and characterization is based on clinical considerations. Treatment with crizotinib has to be restricted to tumors with a proven ALK-gene rearrangement, which implies a systematic pre-screening of tumor samples with reliable technical approaches. However, tumor tissue from patients with lung cancer is not always available or in a sufficient amount to perform both the pathological examination and an increasing list of immuno/molecular analyses aimed at stratifying patients for the use of targeted therapies. At variance with free tumor DNA/RNA in plasma, which may be derived from apoptotic cells and lacks the tumor cell invasive properties, CTCs may represent a "liquid biopsy" and constitute the ideal target for non-invasive theranostic tests.

The inventors used the ISET approach to isolate CTCs, as they and others have shown that this method displays high sensitivity for CTC isolation in NSCLC patients [15-17]. As previously pointed out, CTC isolation by ISET is dependent on cellular size and independent of any cellular marker. Thus, tumor cells expressing epithelial markers as well as those having lost epithelial antigens, due to EMT, are efficiently isolated by ISET [17, 21, 24, 25]. Moreover, ICC and molecular analyses, including FISH, can be developed in CTCs isolated and characterized using ISET [17, 18, 21, 23-25]. Interestingly, it was demonstrated the reproducibility of the results for detection of ALK by ICC and FISH on a subgroup of 34 patients tested before surgery and, 7 days and 15 days after surgery, and including 5 ALK-positive patients for tumor tissue. Consistent results were obtained blindly in the three samples obtained from each patient. These results confirm the technical reproducibility of ICC and FISH analysis for ALK on filters and show the feasibility of a kinetic real-time follow-up of patients by CTC analysis.

Reliable assessment of ALK-gene rearrangement in lung tumor tissues is recognized as a diagnostic and technical challenge [31, 36]. The ALK status on tumor samples can be evaluated using FISH, immunohistochemistry and/or the reverse transcriptase-polymerase chain reaction (RT-PCR) [31, 35-39]. FISH is the diagnostic method used as an eligibility criterion in current clinical trials with crizotinib [38]. HC with antibodies specific for the human ALK protein (antibody clone ALK1) is diagnostic for an ALK rearrangement in a subset of anaplastic large cell lymphomas, having such sensitivity and specificity that genetic tests are considered unnecessary [38]. In NSCLCs, the expression of the ALK protein from the rearranged ALK gene is lower. However, the development and use of new ALK-specific antibodies has provided very interesting results.

The inventors have used the anti-ALK antibody, clone 5A4, which has been recently shown to accurately type 20/20 NSCLC tumor tissues [36]. In the five ALK-rearranged cases, it was noted that no more than 50% of tumor cells were ALK-FISH positive in the tumor, whereas 100% of these cells were ALK positive by IHC. However, IHC for ALK was heterogeneous in certain areas of the tumors, and some cells were only faintly stained (1+) whereas others were strongly stained (3+). Thus, as described in a recent study, a correlation between IHC and FISH for the ALK gene rearrangement can be observed in only some areas of tumors [40], raising the issue of a better and more appropriate comparison between FISH positive and "IHC 3+ only" positive cells. As preliminary data, the present study shows that ICC performed on CTCs may be a promising tool to detect ALK-rearrangement as well as other genomic alterations, such as EGFR mutations. In this regard, some EGFR mutations can be demonstrated by IHC in a subset of lung adenocarcinomas using specific antibodies [31, 41]. We can speculate that such EGFR mutations could also be demonstrated using the ICC approach on CTCs in this subset of lung cancers. It is noteworthy that all CTCs detected in the present study were ALK-FISH positive and strongly positive by ICC using a specific antibody against ALK. CTCs harboring this specific genomic alteration may have facilitated migration and represent an aggressive set of tumor cells. ALK-gene rearrangement can also be detected by RT-PCR [30, 36]. RT-PCR is a challenging approach requiring high quality RNA to afford amplification of multiple transcripts with variable sizes [36]. Finally, a quantitative real-time PCR approach has been recently developed to quantify ALK transcripts and obtained encouraging results [36]. The inventors did not try to look for ALK rearrangement using an RT-PCR approach, since it was thought that the quantity and quality of the RNA that could be potentially extract from CTCs isolated by ISET would not be sufficient for the test since the commercial buffer used for blood dilution before filtration contains formaldehyde. However, this strategy can be tested using a new ISET buffer developed to isolate fresh CTCs with unchanged sensitivity as compared to fixed CTCs.

The use of non-invasive CTC-based tests may allow implementation of real-time molecular theranostic follow-up of patients to identify potential new genomic alterations involved in resistance to targeted therapies [42]. In this regard, emergence of acquired resistance to crizotinib is a new challenge in the clinical care of ALK positive lung cancer patients [11, 43, 44]. In fact, new genomic alteration (s) may occur during crizotinib therapy and can make the initial targeted treatment inefficient. Thus, real-time monitoring could be developed in aiming to detect potential additional genomic alterations through molecular tests for CTCs isolated by ISET and diagnostically characterized by a morphological approach.

The inventors have shown the feasibility of detection of ALK-gene rearrangement in CTCs isolated by ISET and characterized as CTCs with malignant features. Consistent results using the ICC and FISH molecular approaches were found and, importantly, it was also found consistent results in CTCs as compared to tumor tissues in the 87 tested patients. These results provide a CTC-based theranostic approach for evaluation of non-invasive ALK status pre-screening of lung cancer patients.

Example 3: Application of the Present Invention to Early Diagnosis of Invasive Cancers "Sentinel" Circulating Tumor Cells allow early diagnosis of lung carcinoma in patients with chronic obstructive pulmonary disease.

Circulating tumor cells (CTC) are thought to circulate at a very early stage in invasive cancers; however, they have never been reported as invasive cancers first hallmark. We report about three out of 168 patients with Chronic Obstructive Pulmonary Disease (COPD), a pre-tumor condition of Non-Small Cell Lung Cancer (NSCLC), who were found to have CTC detected by ISET (Isolation by Size of Tumor Cells), a highly sensitive "cytopathology-based" CTC-platform. CT scan, performed yearly, detected a lung nodule only 1 to 4 years after CTC appeared in blood leading to its surgical resection and pathological diagnosis of early stage NSCLC. ISET was then repeated 9 or 12 months after surgery and showed disappearance of CTC. These 3 cases show, as a proof of concept, the potential of CTC to be used as an early indicator of invasive lung cancer in "at risk" patients.

Circulating Tumor Cells (CTC) belong to the group of "circulating rare cells" (CRC) in blood, which detection may open new paths in non-invasive predictive medicine. CRC are not detectable by current blood analyses as their level may be as low as one per ml of blood (or lower), thus one cell mixed with an average 10 million leukocytes and 5 billion erythrocytes. Furthermore CRC are of different types, including both epithelial and mesenchymal CTC, epithelial non-tumor cells, spread by inflammatory diseases and iatrogenic interventions, endothelial cells, stem cells and fetal cells (in pregnant women). Thus, specific detection of CTC implies their differential diagnosis from other CRC and a double technical challenge of sensitivity and diagnostic specificity [45].

Because of these technical difficulties, methods detecting circulating epithelial cells, but not diagnostic for CTC, have been used to develop prognostic/predictive markers mostly in patients with metastatic cancers [46]. However, a combination of data from clinical, molecular and animal studies have recently shown that invasive cancers spread tumor cells at a very early step of their development, suggesting that a sensitive and diagnostic approach for CTC detection could be of help for their early diagnosis [47, 48].

Lung cancer is an aggressive and highly invasive disease. Its early diagnosis is a critical issue since 94 million smokers are at elevated risk for the disease that remains the leading cause of death in US [49]. The National Lung Screening Trial, which studied 53,454 persons at high risk for lung cancer, has recently shown that low dose CT screening is associated with a decrease of mortality for lung cancer of 20% [49]. However, this result was associated with an impressive 96.4% of false positive results, as out of 26,309 patients screened, 7191 were found positive but only 649 were further revealed to have lung cancer. Furthermore, the total number of patients with lung cancer was 1060, including 411 false negative which were missed by the CT screening In this setting, the inventors reasoned that the highly invasive character of lung cancer could be used as its Achilles' heel and permit its early diagnosis through the sensitive and diagnostic detection of CTC. Thus, ISET (Isolation by Size of Tumor Cells) was used which is a straightforward approach for very sensitive isolation of intact CTCs allowing their cytopathological diagnosis [46, 50, 51].

Three patients are described with Chronic obstructive pulmonary disease (COPD), a pathology which is considered a risk factor for lung cancer, who were found having CTC in blood years before lung tumor detection by imaging.

This report shows for the very first time in humans that the sensitive and diagnostic identification of CTC provides a promising test for early diagnosis of invasive cancers Case Reports Case 1

In 1995, Patient XB, male, aged 49, was given a diagnosis of moderate (GOLD2) Chronic obstructive pulmonary disease (COPD) in 1995 based on lung function tests, FEV1 (forced expiratory volume in one second) between 50 and 79%, and Chest x-ray. He had been smoking 45 PY (pack-year: 1 daily pack of cigarettes per 45 years). Fourteen years later (October 2009), he was tested by ISET and found to have 67 CTC and 3 CTM (Circulating Tumor Microemboli) in 10 ml of blood identified by cytopathological analysis. A low-dose spiral CT-scan performed at the same date confirmed the diagnosis of COPD but failed to show lung nodules. CT-scan was then planned every year and, one year later (October 2010), showed for the first time the presence of a lung nodule of 1.5 cm diameter in the right lower pulmonary lobe. Surgery was performed one month later. The pathological analysis and cancer staging revealed a tubulopapillary adenocarcinoma stage IA with no spread to lymph-nodes or distant metastasis (pT1aN0M0). Tumor genotyping showed a K-Ras mutation in codon 12. The patient did not receive any further treatment. He was tested by ISET 9 months after surgery and no CTC were found in his blood.

Case 2

Patient AC, male, was given a diagnosis of severe (GOLD 3) COPD in 1998, at age of 54, based on lung function tests, FEV1 between 30 and 49%, and Chest x-ray. He had been smoking 60 PY. Eleven years later (May 2009), he was tested by ISET and found to have 43 CTC and 1 CTM in 10 ml of blood, identified by cytopathological analysis. A low-dose spiral CT-scan performed at the same date showed the signs of COPD but was unable to detect any lung nodule. CT-scan was then repeated every year and 3 years later, in September 2012, showed for the first time the presence of a lung nodule of 2.4 cm diameter in size in the left superior pulmonary lobe. The patient underwent surgery one month later. Pathological analysis and cancer staging revealed a tubulopapillary adenocarcinoma stage IA with no spread to lymph-nodes or distant metastasis (pT1bN0M0). Tumor DNA analysis showed a K-Ras mutation in codon 12. The patient did not receive any further treatment. He was tested by ISET 12 months after surgery and no CTC were found in his blood.

Case 3

Patient BM, male, was given a diagnosis of moderate (GOLD2) COPD in 1999, at age 47, based lung function tests, FEV1 between 50 and 79%, and chest x-ray. He had been smoking 35 PY. Nine year later (February 2008), he was tested by ISET and found to have 32 CTC and 1 CTM in 10 ml of blood. A CT-scan performed at the same date confirmed the diagnosis of COPD but failed to show any lung nodule. A CT-scan was then performed every year and revealed 4 years later, in August 2012, a nodule of 1.4 cm diameter in the right superior pulmonary lobe. Surgery was performed one month later. The pathological analysis and cancer staging revealed an acinar adenocarcinoma stage IA with no spread to lymph-nodes or distant metastasis (pT1aN0M0). Tumor genotyping showed a K-Ras mutation in codon 12. The patient did not receive any further treatment. He was tested by ISET 12 months after surgery and no CTC were found in his blood.

Methods

The ISET method is an engine-powered blood filtration-based approach, which enriches circulating CTC and CTM on a polycarbonate membrane with pores of 8 microns [50, 51]. Peripheral blood (10 mL) was collected in buffered EDTA, maintained at 4° C. and processed within 1 hour of collection. Seven spots on the membrane were processed for immunocytochemistry and 3 spots for May Grünwald Giemsa (MGG) staining for cytological analysis. Immunocytochemistry was performed as described previously, using double immunolabeling with a pan-cytokeratin antibody (mouse, clone KL-1, Immunotech, Marseille), and an anti-vimentin (mouse, clone V9, Dako, Paris) antibody applied to filters for 45 min at room temperature.

Figure 2:
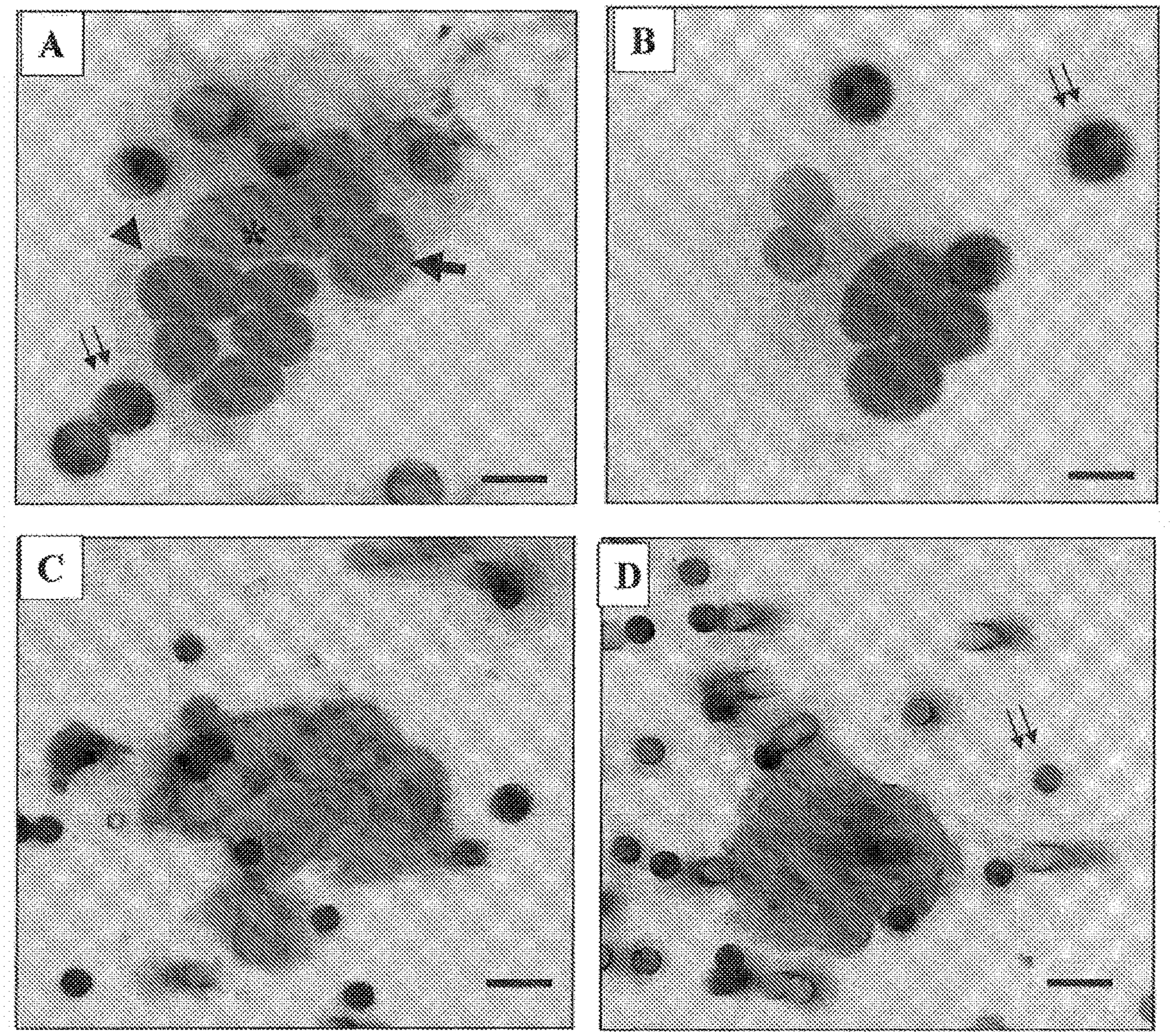
FIG. 2. Cytomorphological analysis of circulating non haematological cells with malignant features—Circulating Tumor Cells (CTCs) detected using the ISET method in patients with COPD. (A) and (B) CTCs isolated by the ISET method and identified by MGG staining protocol in patients with COPD having developed lung cancer. (C) and (D) Immunostained CTCs observed on filtered blood using the ISET method for patients with COPD.
Figure 2A:
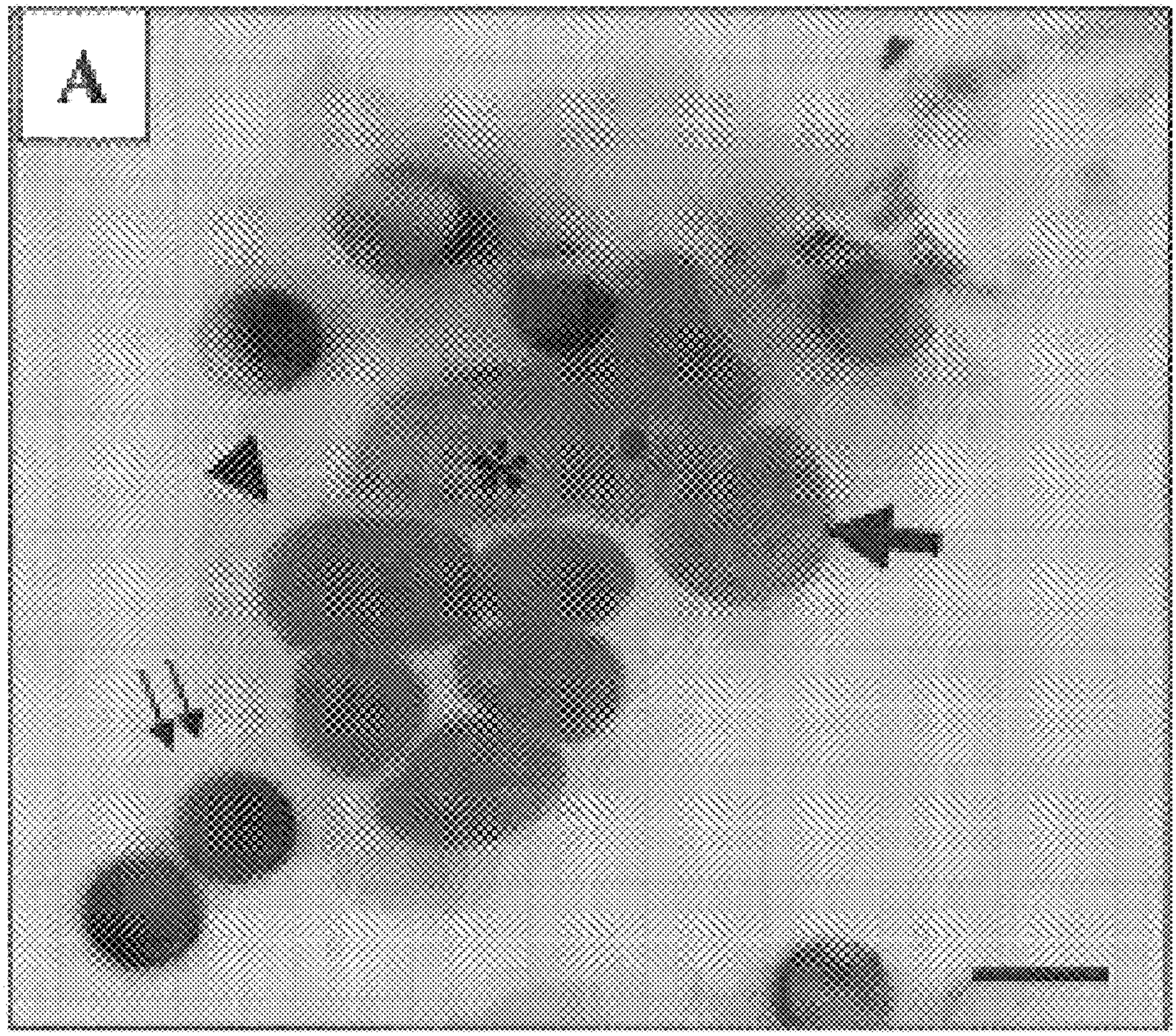
FIG. 2(A) Isolated CTC with malignant cytomorphological features (double arrows: pores of the filter).
Figure 2B:
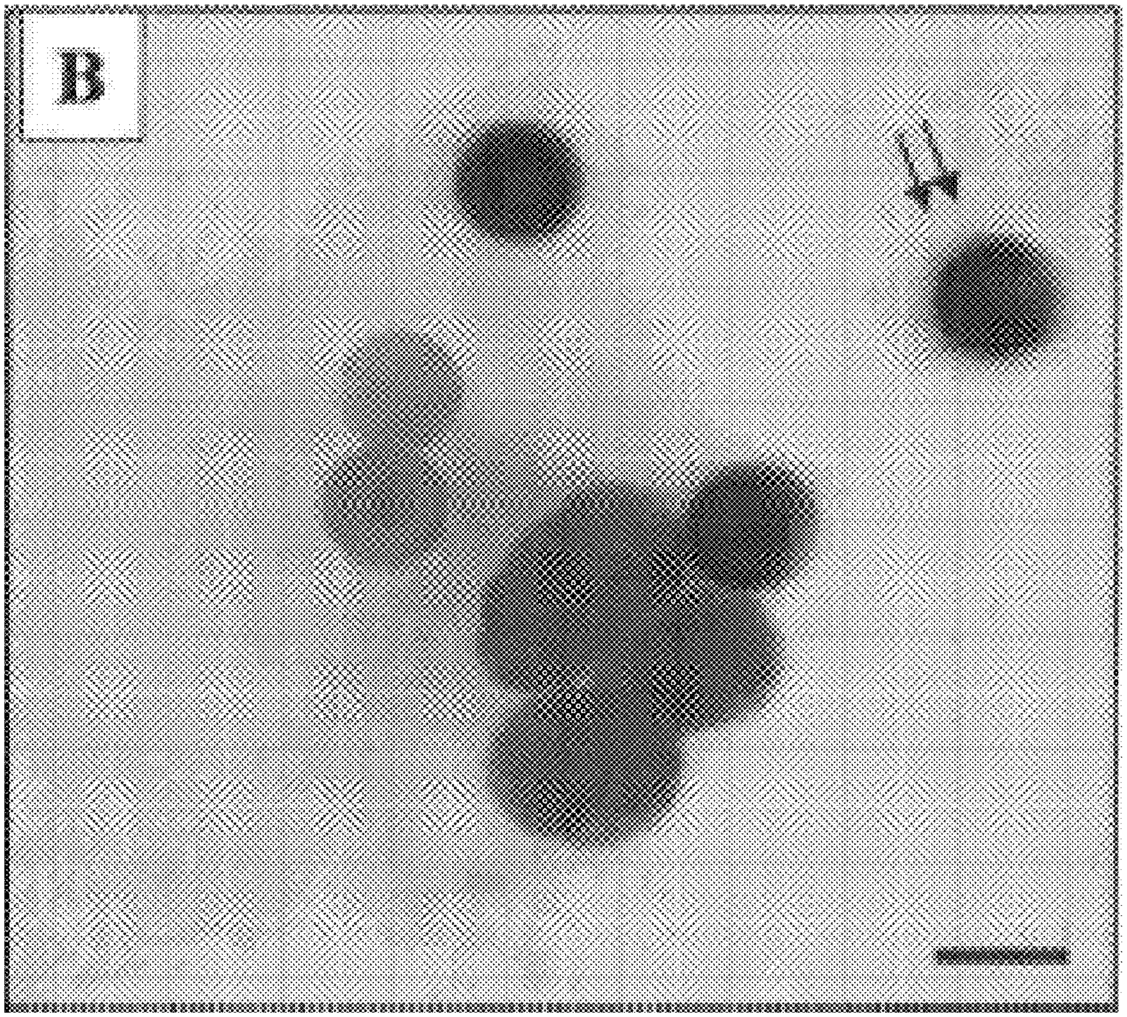
FIG. 2(B) Cluster (CTM) composed of 9 CTCs with malignant cytomorphological features (Original magnification×1000; bars: 8 μm; double arrows: pores of the filters).
Figure 2C:
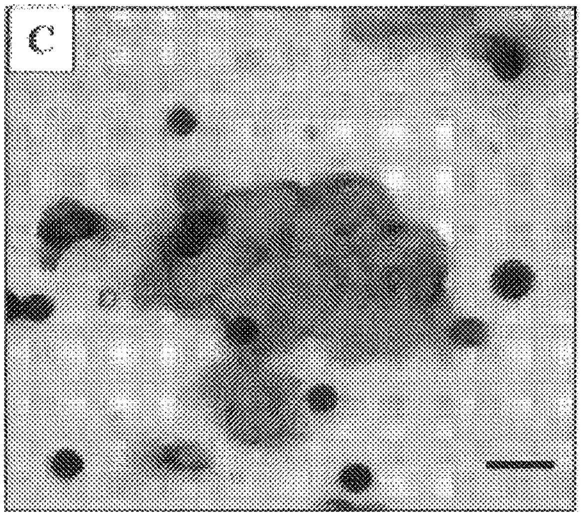
FIG. 2(C) CTCs strongly expressing the pan-cytokeratin antigen only in patient with COPD.
Figure 2D:
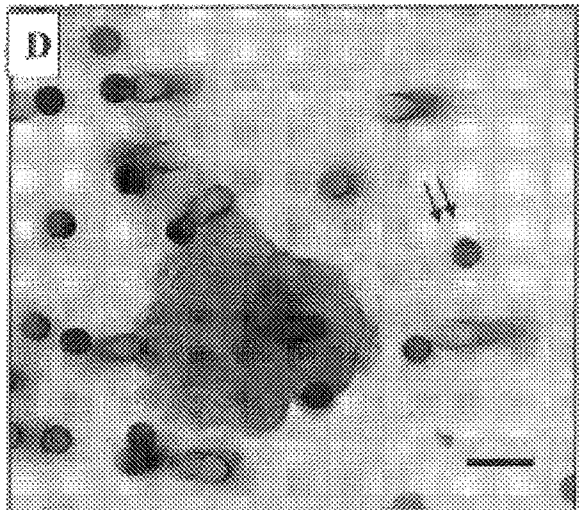
FIG. 2(D) CTCs co-expressing pan-cytokeratin and vimentin antigens in patient with COPD (Original magnification×400; bars: 16 μm; immuno-phosphatase staining with a pan-cytokeratin antibody (KL1) and immuno-peroxidase staining with an anti-vimentin antibody; double arrows: pores of the filters).

Using ISET, patients were considered positive for CTC based on cytopathological analysis of the isolated cells on MGG staining, and detection of cells with characteristic malignant features according to previously defined criteria [51] (FIG. 2).

Results

Using ISET, 3 out of 168 (1.8%) of COPD patients were found positive for CTC based on isolation by ISET and cytopathological analysis of the isolated cells by MGG staining, allowing detection of cells with characteristic malignant features according to previously defined criteria [51].

The three COPD patients having CTCs at baseline detected by cytopathology analysis on ISET who developed a lung cancer in their follow-up were found to have between 32 and 67 CTCs which were isolated or grouped into sheets (FIG. 2). CTCs revealed large nuclei, with scattered nuclear grooves, heterochromatin clumps, and a moderate amount of cytoplasm with high Nuclear/Cytoplasmic ratio (FIG. 2). Furthermore, these patients demonstrated occasional CTM as follows: patient 1 had 3 CTM composed of 3, 9 and 15 CTCs; patient 2 had 1 CTM with 20 cells, and patient 3 had 1 CTM with 12 CTCs. Occasional clusters revealed tridimensional cohesive sheets of oval or polygonal CTCs showing nuclear atypia, moderate to prominent anisonucleosis, with frequent multiple nucleoli, and nuclear overlapping. The corresponding immunostained cells mainly expressed pan-cytokeratin alone (FIG. 2). However, a small number of CTCs strongly expressed vimentin with a weak associated cytokeratin expression (FIG. 2).

Isolated cells with more benign cytomorphological features were also detected by ISET in 3 out of 168 (1.8%) COPD patients. However, neither these 3 patients nor the other 162 patients with COPD were shown to develop a lung nodule during the subsequent follow up (mean follow up time: 48 months). No CTC were detected in 42 control smokers without detectable pathology and in 35 non-smoking healthy individuals.

Discussion

Lung cancer is known to be a highly invasive cancer, with more than 75% of patients not eligible for surgery at diagnosis [52]. Because of its high rate and highly invasive character, it is the leading cause of cancer-related death worldwide [53]. In this field, the discovery of a diagnostic and non-invasive biomarker could be crucial to unroll the following steps of low-dose spiral CT-scan screening and early surgical intervention. Since the highly malignant behaviour of lung cancer is bound to its invasive potential, it was thought that the use of a highly sensitive and diagnostic detection of CTC could complement CT-scan investigations and help reducing the false positive and negative results related to CT-scan screening. The inventors thus targeted a population of 168 patients with COPD. COPD is the third leading cause of death in the U.S. and is projected to become the fourth leading cause of death worldwide by 2030, due to an increase in smoking rates. COPD is considered as a preneoplastic condition for lung cancer and it has been calculated that, overall, 2.2% of COPD patients develop lung cancer per year. However, the progression of COPD increases the susceptibility to lung carcinogenesis by up to 4-6 fold, an observation which is thought to be due to shared mechanisms in both COPD and lung cancer. Thus, early diagnosis of COPD is important because smoking cessation early in the COPD disease process slows disease progression and decreases morbidity and mortality [54].

Several methods have been applied to the isolation and detection of Circulating Tumor Cells, with variable sensitivity and specificity [45]. However, the inventors thought that, in the setting of early diagnosis of lung cancer, only a cytopathological diagnostic approach could be suitable to reveal "sentinel CTC/CTM" to be used in a combined approach for early diagnosis of lung cancer also including CT-scan screening.

ISET is a direct and rapid treatment of blood samples that isolates intact CTC from blood in a highly sensitive manner also allowing their immunocytopathological and molecular analysis.

The three cases reported here revealed a relevant number of CTC/CTM 1 to 4 years before detection of a lung nodule by CT-scan. Unfortunately, ISET filters were not stored at −20° C. making impossible to study DNA mutations in the CTC/CTM. However, for the first time, these data validate in humans the results obtained in animal models showing that CTC are spread by invasive cancers as early as at the stage of "in situ" carcinoma. In this setting, it is also important to notice that neither CTC nor CTM were found by ISET in 42 smokers without a detectable pathology and in 35 non-smoking healthy individuals. Overall, 562 subjects without cancer have been studied by ISET by different groups and shown to be without CTC in their blood.

As shown herein for the first time about three patients at risk of developing lung cancer who were found to have CTC detected by ISET and cytopathology 1 to 4 years before a lung nodule was identified by imaging. In these three patients the lung cancer has been diagnosed at an early stage (IA) allowing prompt surgical resection; they were then shown to be without CTC several months after surgery. Larger studies are now needed to assess the potential of diagnostic identification of CTC as reliable tool for early diagnosis of lung cancer in at risk patients.

Example 4: Application of the Present Invention to Isolation and Characterization of Cervical Trophoblasts from Transcervical Samples Trophoblasts. According to a preferred mode of implementation, trophoblastic cells can be extracted by filtration from transcervical samples, identified by cytomorphological analyses and their genome can be characterized individually by PCR after laser microdissection and whole genomic amplification Transcervical samples are collected from pregnant woman between the 5th and the 15th week of gestation using a cytobrush tool rotated in the central opening of the cervix. Transcervical samples are transferred into PBS solution supplemented by a fixative reagent. The sample can be stored at 4° C. for months before filtration.

Transcervical samples are diluted with distilled sterile water according to their cellularity before filtration and analyzed by cytomorphological staining.

Single trophoblastic cells are then collected by laser capture microdissection and molecular analysis is performed for genotyping and genetic analyses as reported by publications (Saker et al, Prenatal Diagnosis 2006).

A new approach for non-invasive isolation of cervical trophoblasts in pregnant women at early term of pregnancy.

A major goal of modern prenatal care is to replace invasive prenatal diagnosis, which is bound to a 1 to 2% risk of fetal loss [55] with completely safe "non-invasive" testings. Fetal DNA can be retrieved non-invasively from three sources: circulating fetal cells in maternal blood, in particular circulating erythroid and trophoblast cells, which do not persist in blood after delivery or miscarriage; transcervical trophoblasts, in transit from the uterine cavity to the cervix, and free fetal DNA that is part of the total cell free DNA circulating in maternal blood. Non-invasive recovery of fetal cells is expected to provide pure (not mixed with maternal DNA) fetal DNA, allowing to develop a non-invasive and completely reliable alternative to amniocentesis and CVS. However, circulating fetal cells and cervical trophoblasts are very rare and their isolation is a technical challenge. Highly powerful next generation sequencing approaches targeting cell free fetal DNA are now available and have been proven to provide reliable and non invasive prenatal aneuploidy detection [56, 57, 58, 59, 60]. However, these methods cannot replace amniocentesis and CVS because they do not target pure fetal DNA. Furthermore, these approaches cannot be applied at early terms of pregnancy and require sophisticated and expensive technology.

Our team has demonstrated that circulating trophoblast cells can be easily extracted from maternal blood by ISET (Isolation by Size of Epithelial Tumor/Trophoblast cells) because trophoblasts are larger than peripheral blood leukocytes. Moreover, isolated cells were genetically analysed and their usefulness in non-invasive prenatal diagnosis (NI-PND) was demonstrated for two recessive disorders, spinal muscular atrophy and cystic fibrosis [61, 62].

The presence of fetal cells in the endocervix was first demonstrated by Shettles in 1971. Trophoblast cells are thought to be shed from regressing chorionic villi in the uterine cavity and from it toward the cervix [63, 64]. The uterine cavity disappears between 11 and 12 weeks gestation (WG), following the fusion of the decidua basalis and parietalis, hence the possibility of collecting those rare cells is expected to be transient and is restricted to the early terms of pregnancy. Collecting fetal cells from the cervix and the lower pole of the uterine cavity, called transcervical cell (TCC) sampling, is an alternative to the isolation of fetal cells from maternal blood and provides an additional source of pure fetal DNA for NI-PND. Of great advantage is the fact that TCCs are solely trophoblasts (cyto- and syncytiotrophoblasts) which are shed and do not persist beyond the current pregnancy . . . . Different TCC sampling approaches were developed and include the following: intrauterine lavage, endocervical lavage, endocervical mucus aspiration as well as endocervical sampling using a cytobrush. Numerous studies aimed at ascertaining the best TCC sampling method have established that uterine and endocervical lavage are the most effective methods to consistently yield fetal cells as early as 5 weeks gestation [65, 66, 67, 68, 69, 70]. However, although they have been described as minimally or semi invasive, the major concern regarding these methods is the risk of fetal loss [71, 72]. In most studies, samples were collected immediately prior to termination of pregnancy, hence the effect on ongoing pregnancies has not been sufficiently examined.

An ideal sampling method should inflict no complications, should have no negative impact on the ongoing pregnancy, be easy to perform outside a hospital setting and be cost effective. A safe method was adopted as described in the Material and Methods section (collection of samples). Most importantly, the safety of this method is demonstrated by the fact that it is routinely performed during the first trimester of pregnancy.

In this study, a safe sampling approach to collect cervical samples was combined with ISET, a very practical method to study rare cells, not only because it eliminates elements according to size, such as sperms and leukocytes, but also because it forms an optimal layer of cells to aid laser microdissection and any other type of cell analysis. By utilizing a unique staining method, which facilitates the recognition of fetal cells, it was possible to microdissect single cytotrophoblasts and syncytiotrophoblasts and demonstrate their fetal nature by genotyping. It is also shown herein, as was the case for trophoblasts isolated from blood, cells are amenable to be used for NI-PND. A new approach is provided to consistently and noninvasively retrieve fetal cells usable as part of a true non-invasive alternative to amniocentesis and CVS for non-invasive prenatal diagnosis of genetic diseases.

Materials and Methods

Collection of Samples:

TCC samples were collected from pregnant women at risk of carrying a fetus with a monogenic disease (Hôpital Necker-Enfants Malades) immediately before chorionic villus sampling, as well as from women undergoing elective termination of pregnancy (TOP) (Antoine Béclère). All women were between 7 and 12 weeks gestation. Cells were obtained with the use of a cytobrush, but unlike the conventional TCC sampling method, in our study the brush was not inserted into the endocervical canal but rather rotated at the external os. Cytobrushes were transferred to 10 ml of a methanol-containing preservative solution.

Staining and Fixation of Samples with Alcian Blue:

1 ml of each sample was mixed with 1 ml of a 1.1% Alcian blue 8GX/3% glacial acetic acid solution (Sigma-Aldrich, St. Louis, MO, USA) and incubated for 30-50 minutes. Samples were then diluted 25 fold in water, leaving us with a total volume of 50 ml. Each sample was thoroughly mixed and incubated for 5 minutes.

Filtration of Samples with ISET:

ISET was carried out as previously described with only minor modifications [61]. Briefly, diluted samples (50 ml) were filtered through polycarbonate filters with calibrated 8-μm-diameter, cylindrical pores. Cells from 1 ml of sample were concentrated on ten 0.6-cm-diameter spots on the filter.

Staining of Cell Nuclei with Red Nuclear Stain:

In order to stain the nuclei of the concentrated cells on the filter, each spot was covered with a 0.1% nuclear fast red stain/5% aluminum sulphate solution (Sigma-Aldrich, St. Louis, MO, USA), incubated for 2 minutes and then thoroughly rinsed with water. Filters were dried on air.

Analysis of Filters and Laser Microdissection:

Typically, 2 filters per sample were made, and thus, processed on average 2 ml of each sample. Single cells not stained by Alcian blue and displaying a cytotrophoblast-like or syncytiotrophoblast-like morphology were retrieved from the filters by laser-capture microdissection using the Nikon TE 2000-U (Nikon Paris, France and MMI Zurich, Switzerland) laser-equipped microscope. Each single cell was catapulted onto the lid of a microfuge tube suited for PCR.

Molecular Analysis:

Each microdissected cell was lysed in 15 μL of lysis buffer (100 mmol/L Tris-HCl, pH 8; 400 μg/mL proteinase K) for 2 h at 60° C., followed by proteinase K inactivation at 94° C. for 15 min. For primer extension preamplification (PEP) [73], to the lysed cell we added 5 μL of a 400 μM solution of random primers (Kit genPEP 75 OD, Genetix, Boston, USA), 6 μL of PCR buffer (25 mM $MgCl_2$/gelatin (1 mg/mL), 100 mM Tris-HCl, pH 8.3, 500 mM KCl), 3 μL of a mixture of four dNTPs (each at 2 mM) and 1 μL (5 U) of Taq polymerase (Applied Biosystem, Foster City, CA, USA) in a final volume of 60 μL. Single cell genotyping was performed to identify cells having a fetal genome by using STR primers found to be informative though the analysis of paternal and maternal genomic DNA. Amplification was performed in 60 μL containing 6 μL of the PEP product, 10 mM Tris-HCl, 50 mM KCl, 2.5 mM MgCl2, 200 μM of each deoxynucleotide, 0.5 μM of each STR 'outer' primer and 2 U of Taq Gold (Applied Biosystems, Foster City, CA, USA). 2 μl of a 1:10 diluted PCR outer product were re-amplified in 20 μL final volume using 'inner' fluoresceinated STR primers and the same PCR protocol. One μL of the 1:20 diluted inner PCR product was then mixed with 13.5 μL of deionised Hi-Di formamide and 0.5 μL of Genescan 400 HD (ROX) marker (Applied Biosystems) and loaded into an ABI Prism 3100 automated sequencer (Applied Biosystems). Profiles were analyzed using the Genescan and Genotyper software programs (Applied Biosystems).

The non-invasive prenatal diagnoses of SMA and cystic fibrosis were performed as previously described [62].

Invasive diagnoses were carried out at Hôpital Necker-Enfants Malades, Laboratoire de Génétique Médicale, Paris.

Results

A total of 21 cervical samples was screened, in which a cytobrush was used to retrieve cells solely at the level of the external os, from pregnant women between 7-12 weeks of gestation. Among those were 14 scheduled for chorionic villus sampling (CVS) because they presented a risk of carrying a fetus with a monogenic disorder, and 7 women were about to undergo elective termination of pregnancy (TOP).

Figure 3A:
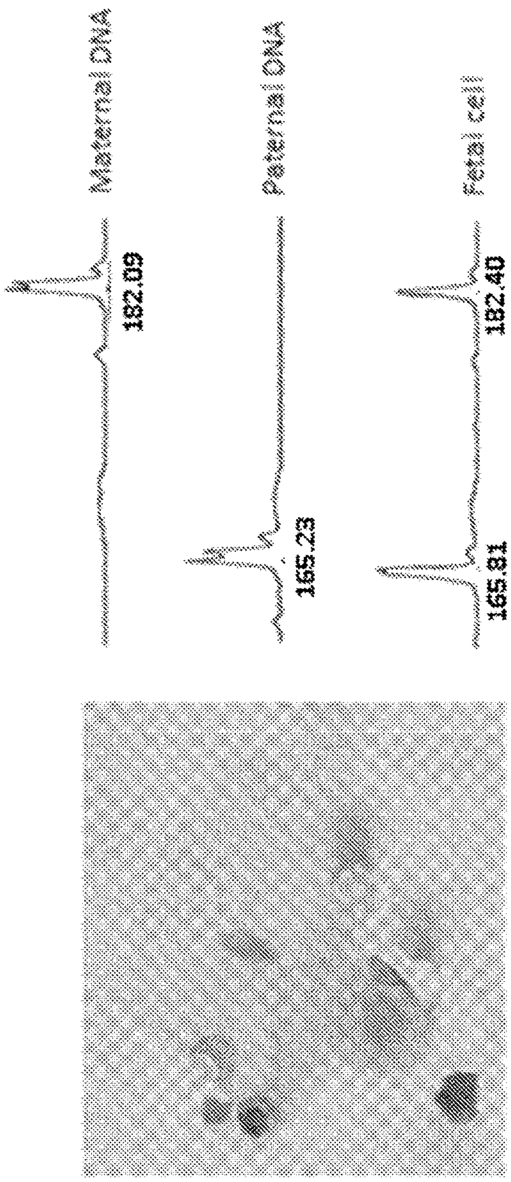
FIG. 3(A). Detection of cytotrophoblast cells in cervical samples using ISET. The fetal nature of isolated cells was confirmed by STR-genotyping with informative markers D5S615.
Figure 3B:
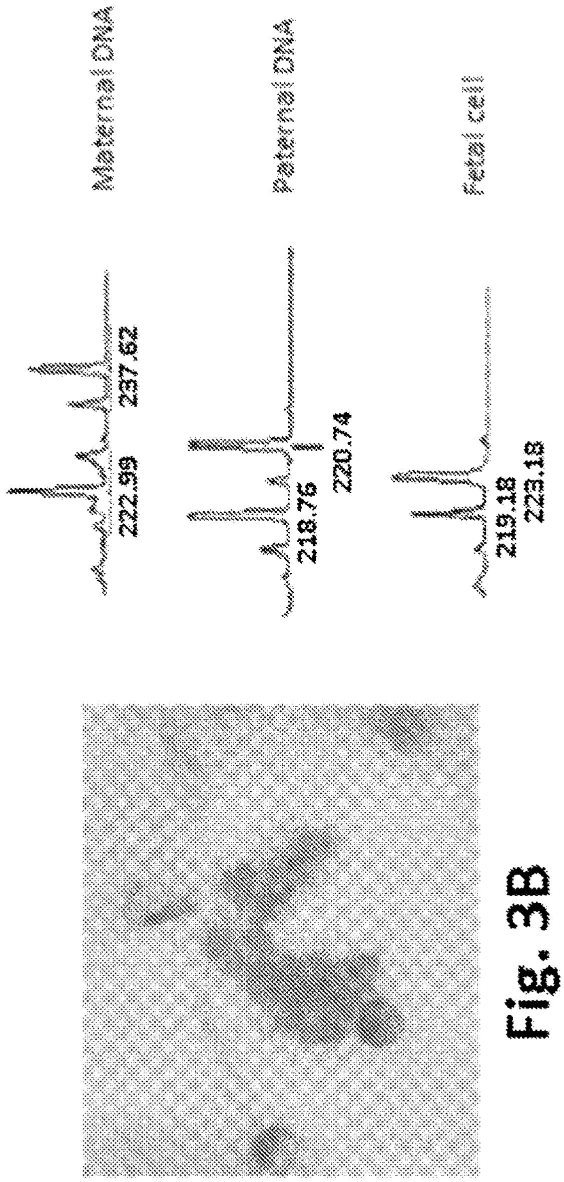
FIG. 3(B). Detection of syncytiotrophoblasts in cervical samples using ISET. The fetal nature of isolated cells was confirmed by STR-genotyping with informative markers D21S11.

Cervical samples typically contain a variety of maternal cells. As shown in FIG. 3A and FIG. 3B, exocervical squamous epithelial cells are easily recognized in microscopic images. However, endocervical cells and fetal cytotrophoblasts can have a similar morphology and are thus much harder to discriminate. Alcian blue reacts with the mucus producing columnar epithelial cells of the endocervix, and was thus used to facilitate the recognition of fetal cells that should remain unstained. Cells displaying a cytotrophoblast-like morphology: round cells with large, irregular hyperchromatic nuclei (FIGS. 3A and B) were sought. In this manner, we were able to isolate single cytotrophoblasts, whose fetal genotypes were verified by fluorescent PCR analysis of informative STR markers (FIG. 3, Table 4).

TABLE 4

Isolation of fetal cells (cytotrophoblasts/syncytiotrophoblasts) from 21 cervical samples and exemplary non-invasive prenatal diagnoses for cystic fibrosis.

| Couple | Term of pregnancy | Informative STR marker | Cytotrophoblasts/ Syncytiotrophoblasts | Fetal cells/ml sample | Non-invasive diagnosis | Invasive diagnosis |
|---|---|---|---|---|---|---|
| 1(CF) | 12 weeks + 1 day | D5S816/D21S1437 | 3 | 3 | No DelF508 | Confirmed |
| 2(CF) | 12 weeks + 4 days | D7S486/D7S523 | 2 | 2 | DelF508 carrier | Confirmed |
| 3(CF) | 12 weeks + 1 day | D21S1435 | 5 | 5 | DelF508 carrier | Confirmed |

TABLE 4-continued

Isolation of fetal cells (cytotrophoblasts/syncytiotrophoblasts) from 21 cervical samples and exemplary non-invasive prenatal diagnoses for cystic fibrosis.

| Couple | Term of pregnancy | Informative STR marker | Cytotrophoblasts/ Syncytiotrophoblasts | Fetal cells/ml sample | Non-invasive diagnosis | Invasive diagnosis |
|---|---|---|---|---|---|---|
| 4(CF) | 12 weeks + 6 days | D7S523 | 3 | 3 | DelF508 carrier | Confirmed |
| 5(CF) | 12 weeks + 2 days | D16S539/D7S523 | 5 | 5 | DelF508 carrier | Confirmed |
| 6(CF) | 12 weeks + 4 days | D16S539/D7S523 | 3 | 3 | No DelF508 | Confirmed |
| 7 | | D5S816/D21S1437 | 5 | 2.5 | | |
| 8 | | D16S539 | 1/2 | 1.5 | | |
| 9 | | D16S539/D5S816 | 4/2 | 2 | | |
| 10 | | D21S1435 | 5 | 5 | | |
| 11 | | D21S1435 | 3 | 3 | | |
| 12 | | D16S3018 | 10 | 3.3 | | |
| 13 | | D21S1435/D7S523 | 3 | 3 | | |
| 14 | | D16S539/D5S816 | 2 | 0.5 | | |
| 15(TOP) | | D21S11 | 7/2 | 4.5 | | |
| 16(TOP) | | D16S539/D21S1435 | 6 | 6 | | |
| 17(TOP) | | D16S3018/D5S615 | 6 | 3 | | |
| 18(TOP) | | D5S615/D16S539 | 4 | 2 | | |
| 19(TOP) | | D16S539/D5S816 | 4 | 2 | | |
| 20(TOP) | | D16S539/D21S11 | 3 | 1.5 | | |
| 21(TOP) | | D5S615/D5S816 | 2/1 | 1.5 | | |

TOP: Termination of pregnancy,
CF: Cystic fibrosis.

Syncytiotrophoblasts have dense nuclei and are multinucleated and thus are said to be less amenable to molecular analysis. Furthermore, syncytiotrophoblasts can be rather large fragments, thus, the likelihood of mixed cell populations (fetal and maternal) should be increased. In order to augment the number of recovered fetal cells per sample, however, we started to also microdissect polynucleated fragments whose genotypes were again determined by STR analysis (FIG. 3, Table 4). While we were able to isolate syncytiotrophoblasts whose pure fetal nature was confirmed (Table 4), the majority of fragments contained fetal as well as maternal elements, as expected, and were thus excluded from this study.

We identified fetal cells (either cytotrophoblasts or cytotrophoblasts and syncytiotrophoblasts) in all 21 samples, with a frequency of 0.5 to 6 fetal cells per ml of processed sample (Table 4).

In order to show that our previously published protocol for the non-invasive diagnosis of cystic fibrosis (CF) can be successfully applied to fetal cells isolated from the cervix, exemplary diagnoses were made for six CF families (Table 4). Non-invasive diagnosis of CF was based on the presence of the DelF508 mutation [62]. We determined that all fetuses either lacked the DelF508 mutation altogether or were only carriers (Table 4). Our results were confirmed by chorionic villus sampling.

Discussion

The race to develop suitable techniques for the isolation of the rare circulating fetal cells has not been limited to the maternal bloodstream. While next generation whole genome sequencing approaches which target free fetal DNA in maternal serum seem promising, especially in aneuploidy detection, the range of inherited disorders that can be detected are limited simply because the fetal DNA is mixed with maternal DNA. Obtaining fetal cells from the cervix provides an alternative source and has advantages, such as the only type of fetal cell found in the cervix are trophoblasts which are known not to persist beyond the current pregnancy. The major challenge remains the retrieval and isolation of these rare cells, be it in the maternal bloodstream or cervix. Transcervical cell (TCC) sampling combines different methods developed to recover fetal cells from the endocervix and lower pole of the uterine cavity. A major drawback however is the fact that these techniques are minimally or semi-invasive and carry a risk of fetal loss. The least invasive TCC sampling method uses a cytobrush that is typically inserted about 2 cm into the endocervical canal to retrieve cervical mucus. However, larger studies in normal ongoing pregnancies, including long term follow ups need to be conducted before this method can be considered safe. Noteworthy is also the fact that the authors identified fetal cells by use of immunofluorescence microscopy with antigenic markers but did not verify their fetal nature by genotyping. A completely non-invasive and safe sampling method that is routinely administered during the first trimester of pregnancy, takes cells from the ectocervix (spatula) and a cytobrush is then rotated in the central opening of the cervix to retrieve cells from the transformation zone where ecto- and endocervix meet. We chose to adopt this approach to isolate trophoblastic cells in our study and combined it with ISET, a technique developed in our laboratory, which simply layers the cells onto a membrane and thus, poises them for microdissection. We were able to find fetal cells in all of our tested samples, and thus a source of pure fetal DNA for genetic testing. We show that as was the case for maternal blood, cells are amenable to genetic analysis and diagnosis and thus, demonstrate the potential for a variety of genetic tests. Isolating fetal cells from two sources completely non-invasively and by clinically approved sampling methods (blood draw and our safe cervical test) proven safe during pregnancy, could pave the road for the development of early, safe and reliable diagnostic tests for genetic diseases.

The invention comprises the following specific embodiments:

1. A process for identifying, diagnosing, or providing a prognosis for a condition, disorder or disease associated with rare cells comprising:

(a) isolating or extracting rare cells by passing a biological sample through a filter and recovering the isolated rare cells on the filter; wherein the filter has a pore size, pore density or other physical characteristics that retain rare cells but which permit passage of other kinds of cells;

(b) determining the cytomorphology of the isolated or extracted rare cells, and/or immunolabeling the isolated rare cells, and/or performing molecular analysis on the isolated rare cells;

(c) identifying, diagnosing, or providing a prognosis for a condition, disorder or disease and/or a stage of a condition, disorder or disease associated with the rare cells presence and/or number and/or characteristics based on the cytomorphology, and/or immunolabeling, and/or molecular analysis of the isolated or extracted rare cells.

2. The process of embodiment 1, wherein the biological sample is blood that may optionally be filtered in a manner that permits the separation and recovery of the rare cells as well as leukocytes and blood plasma separated from the rare cells for molecular analysis.

3. The process of embodiment 1 or 2, wherein the biological sample is a biological fluid other than blood.

4. The process of any one of embodiments 1 to 3, wherein the biological sample is mucous or is obtained from a mucous membrane.

5. The process of any one of embodiments 1 to 4, wherein the biological sample is obtained from a subject who has cancer or a tumor, or who is suspected of having or at risk of having a tumor or cancer.

6. The process of any one of embodiments 1 to 5, wherein the biological sample is obtained from a subject who has cancer or a non-cancerous proliferative condition, disorder, or disease, or who is suspected of having or at risk of having a non-cancerous proliferative condition, disorder, or disease.

7. The process of any one of embodiments 1 to 6, wherein the biological sample is obtained from a subject who has an inflammatory and/or degenerative condition, disorder or disease, or who is suspected of having or at risk of having an inflammatory and/or degenerative condition, disorder or disease.

8. The process of any one of embodiments 1 to 7, wherein the biological sample is obtained from a subject who has a cardiovascular condition, disorder or disease, or who is suspected of having or at risk of having a cardiovascular condition, disorder or disease.

9. The process of any one of embodiments 1 to 8, wherein the biological sample is obtained from a subject who has an infectious condition, disorder or disease, or who is suspected of having or at risk of having an infectious condition, disorder or disease.

10. The process of any one of embodiments 1 to 9 comprising (a) isolating or extracting rare cells by passing a biological sample through a polycarbonate filter and recovering the isolated or extracted rare cells on the polycarbonate filter.

11. The process of any one of embodiments 1 to 10 comprising (a) extracting or isolating rare cells by passing a biological sample through a PET (polyethylene terephthalate) filter and recovering the extracted or isolated rare cells on the PET (polyethylene terephthalate) filter.

12. The process of any one of embodiments 1 to 11 comprising (a) extracting or isolating rare cells by passing a biological sample through a filter made of any porous material and recovering the extracted or isolated rare cells on the said filter.

13. The process of any one of embodiments 1 to 12, wherein the biological sample is diluted prior to (a).

14. The process of any one of embodiments 1 to 13, wherein the biological sample is fresh prior to (a).

15. The process of any one of embodiments 1 to 14, wherein the biological sample is fixed prior to (a).

16. The process of embodiment 14 or 15, wherein the biological sample is treated by a cell lytic agent prior to (a).

17. The process of embodiment 14 or 15, wherein the biological sample is treated by a mucolytic agent prior to (a).

18. The process of embodiment 14 or 15, wherein the biological sample is treated by a proteolytic agent prior to (a).

19. The process of embodiment 14 or 15, wherein the biological sample is treated by an anticoagulant agent prior to (a).

20. A process of any one of embodiments 1 to 19 wherein the rare cells isolated or extracted by filtration are transferred to a support before further analyses as in (b) or for culture.

21. A process of any one of embodiments 1 to 20, wherein rare cells are collected individually for molecular analyses after their extraction or isolation by filtration.

22. A process of any one of embodiments 1 to 21 wherein all cells extracted or isolated by filtration are collected for use in (b).

23. The process of any one of embodiments 1 to 22, wherein the isolated or extracted rare cells are cultured prior to (b).

24. The process of any one of embodiments 1 to 23, wherein the isolated or extracted rare cells are cultured and used to test their sensitivity to specific drugs and their different doses 25. The process of any one of embodiments 1 to 24, wherein the isolated or extracted cultured rare cells are used to select treatments or targeted treatments to be administered to the patient and to monitor the response and/or resistance to them.

26. The process of any one of embodiments 1 to 25, wherein the isolated or extracted rare cells are fixed prior to (b).

27. The process of any one of embodiments 1 to 26, wherein isolated or extracted rare cells are stained or immunostained on the filter before (b).

28. The process of any one of embodiments 1 to 27, wherein isolated or extracted rare cells are analyzed in (b) by in situ molecular analyses after or before staining or immunostaining 29. The process of any one of embodiments 1 to 28, wherein (b) comprises cytomorphological analysis of the isolated or extracted rare cells in situ on the filter or other support.

30. The process of any one of embodiments 1 to 29, wherein (b) comprises immunolabeling the isolated or extracted rare cells in situ on the filter or other support.

31. The process of any one of embodiments 1 to 30, wherein (b) comprises molecular analysis of the proteins, nucleic acids, or other components of the isolated or extracted rare cells in situ on the filter.

32. The process of any one of embodiments 1 to 32, wherein (b) comprises molecular analysis of the proteins, peptides or polypeptides of the isolated or extracted rare cells.

33. The process of any one of embodiments 1 to 32, wherein (b) comprises molecular analysis of the DNA, RNA, or microRNA of the isolated or extracted rare cells.

34. The process of any one of embodiments 1 to 33, further comprising (b1) visualizing the images of the isolated or extracted rare cells after cytomorphological analysis, immunolabeling, or in situ molecular analysis.

35. The process of any one of embodiments 1 to 34, further comprising (b2) recording the images of the isolated or extracted rare cells after cytomorphological analysis, immunolabeling, or in situ molecular analysis.

36. A process of detection of the presence or absence of rare cells, comprising:

(a) isolating or extracting rare cells by passing a biological sample through a filter and recovering the isolated rare cells on the filter; wherein the filter has a pore size, pore density or other physical characteristics that retain rare cells but which permit passage of other kinds of cells;

(b) optionally, culturing the isolated or extracted rare cells;

(c) optionally, fixing or staining of the isolated or extracted rare cells or optionally cultured rare cells;

(d) analyzing the isolated or extracted rare cells from (a), (b) or (c) by immunolabeling, and/or in situ molecular analysis, and/or molecular analysis of rare cells DNA, RNA, and/or microRNA, and/or molecular analysis of rare cells protein molecules.

37. The process of embodiment 36, wherein the isolated or extracted rare cells are lysed for or during (d).

38. The process of embodiment 36 or 37, wherein the isolated or extracted rare cells are lysed and (d) comprises detecting mutated protein(s) and/or mutated RNA and/or DNA mutation(s) associated with a condition, disorder or disease in the lysed rare cells.

39. The process of embodiment 38, further comprising selecting a targeted treatment for personalized medicine, to evaluate treatment efficacy or to detect possible resistance to treatment based on the detection of mutated DNA, and/or mutated RNA and/or mutated protein(s) in the lysed rare cells.

40. The process of any one of embodiments 36 to 39, wherein the isolated and extracted rare cells are lysed and (d) comprises detecting the presence or absence of ALK mutations in the lysed rare cells.

41. The process of any one of embodiments 36 to 40, wherein the isolated or extracted rare cells are lysed and (d) comprises detecting the presence or absence of ALK mutations in the lysed rare cells, wherein said process further comprises selecting a treatment for a subject, following the efficacy of a treatment, or detecting resistance to treatment based on the presence or absence of the ALK mutation.

42. The process of any one of embodiments 36 to 41, wherein the isolated or extracted rare cells are lysed and (d) comprises detecting the presence or absence of a K-RAS and/or EGFR mutation in the lysed rare cells, wherein said process further comprises selecting a treatment for a subject, following the efficacy of a treatment, or detecting resistance to treatment based on the presence or absence of the K-RAS and/or EGFR mutation.

43. The process of any one of embodiments 36 to 42, wherein the isolated or extracted rare cells are lysed and (d) comprises detecting the presence or absence of a B-RAF and/or HER2 mutation in the lysed rare cells, wherein said process further comprises selecting a treatment for a subject, following the efficacy of a treatment, or detecting resistance to treatment based on the presence or absence of the B-RAF and/or HER2 mutations.

44. A personalized medicine treatment comprising repeating the process of any one of embodiments 36 to 43 using biological samples obtained from the same subject at different times.

45. The personalized medicine treatment of embodiment 44, wherein the biological samples are obtained from the same patient before and after treatment, at different points during treatment for a condition, or during different treatment regimens for a condition, disorder or disease associated with the rare cells.

46. The personalized medicine treatment of embodiment 45, (e) further comprising comparing the number of rare cells between samples obtained a different times to determine efficacy of a treatment regimen or to detect resistance to a treatment regimen, wherein a decrease in the relative number of rare cells detected indicates relative efficacy of a treatment regimen, and wherein an increase in the relative number of rare cells detected indicates resistance to or inefficacy of the treatment regimen; and optionally, (f) selecting an effective personalized targeted treatment for the subject based on (e).

47. The process of any one of embodiments 36 to 43, wherein (d) analyzing the isolated or extracted rare cells comprises determining the type and/or origin of the rare cells.

48. The process of any one of embodiments 36 to 43 and 47, wherein (d) analyzing the isolated or extracted rare cells comprises determining the status of epithelial to mesenchymal transition of the rare cells.

49. The process of any one of embodiments 36 to 43 and 47-48, wherein (d) analyzing the isolated or extracted rare cells comprises determining the status of stem rare cells.

50. The process of any one of embodiments 36 to 43 and 47 to 49, wherein (d) analyzing the isolated or extracted rare cells comprises determining whether the rare cells have a gene-expression signature associated with metastatic or invasive cells or whether the rare cells express determinants associated with metastasis or invasion.

51. The process of any one of embodiments 36 to 43 and 47 to 50, further comprising making an early diagnosis of a condition, disorder or disease associated with the rare cells based on (d).

52. The process of any one of embodiments 36 to 43 and 47 to 51, further comprising making an early diagnosis of cancer and/or invasive cancer associated with the rare cells based on (d).

53. The process of any one of embodiments 36 to 43 and 47 to 52, further comprising making an early diagnosis of the organ where the cancer and/or the invasive cancer originated.

54. The process of any one of embodiments 36 to 43 and 47 to 53, further comprising making an early diagnosis of an infectious condition, disorder or disease associated with the rare cells based on (d).

55. The process of any one of embodiments 36 to 43 and 47 to 54, further comprising evaluating an effect of a candidate drug or candidate treatment on molecular characteristics of rare cells, and selecting a drug or treatment that reduces the number of rare cells in a subject compared to a control not given the drug or treatment, and selecting a drug or treatment that reduces the relative number of rare cells or modifies the molecular or immunological characteristics of the rare cells compared to the control.

56. The process of any one of embodiments 36 to 43 and 47 to 55, further comprising evaluating the predisposition and/or risk of a subject developing a condition, disorder or disease associated with rare cells, wherein an increase in the relative number of rare cells compared to a baseline or control value indicates a predisposition or increased risk of developing said condition, disorder or disease or wherein a molecular or immunological change in the rare cells compared to a baseline or control value indicates a predisposition or increased risk of developing said condition, disorder or disease.

57. The process of any one of embodiments 36 to 43 and 47 to 56, wherein the condition, disorder or disease is a genetic disorder.

58. The process of any one of embodiments 36 to 43 and 47 to 57, wherein the condition, disorder or disease is a cancer or a neoplastic disease.

59. The process of any one of embodiment 36 to 43 and 47 to 56, wherein the condition, disorder or disease is an infectious condition, disorder or disease.

60. A kit comprising at least one of:

one or more filters for extracting or isolating rare cells from a biological fluid, one or more buffers, diluents, or other agents for treating the biological fluid before filtration, one or more buffers for suspending, washing or otherwise treating rare cells after they are extracted or isolated from a biological fluid, one or more transfer buffers for transferring the isolated or extracted rare cells from a filter to a different support, one or more cytomorphological and/or cytochemical staining reagents or other cellular stains, or buffers therefore, one or more antibodies or other reagents for immunolabeling rare cells or buffers therefore, one or more reagents for in situ analysis of rare cells on a filter or other support, one or more lytic agents or lysis buffers for lysing rare cells, one or more antibodies or other reagents for molecular analysis of rare cell proteins, or buffers therefore, one or more probes, primers, nucleotides, enzymes or other reagents for molecular analysis of rare cell nucleic acids including PCR.

61. A composition comprising one or more rare cells isolated or extracted by passing a biological sample through a filter and recovering the isolated rare cells on the filter; wherein the filter has a pore size, pore density or other physical characteristics that retain rare cells but which permit passage of other kinds of cells.

62. A filter or other support comprising the composition of embodiment 61.

63. The process of any one of embodiments 36 to 43 and 47 to 59 further comprising making an early diagnosis of lung cancer associated with tumor cells based on step d) of embodiment 36 to 43 and 47 to 59.

64. The process of any one of embodiments 36 to 43 and 47 to 59 further comprising making an early diagnosis of presence and/or severity of cardiovascular disease associated with endothelial cells based on step d) of step to 43 and 47 to 59.

INCORPORATION BY REFERENCE

Each document, patent, patent application or patent publication cited by or referred to in this disclosure is incorporated by reference in its entirety, especially with respect to the specific subject matter surrounding the citation of the reference in the text. However, no admission is made that any such reference constitutes background art and the right to challenge the accuracy and pertinence of the cited documents is reserved.

REFERENCES

1. Goya T, Asamura H, Yoshimura H et al., Prognosis of 6644 resected non-small cell lung cancers in Japan: a Japanese lung cancer registry study. Lung Cancer 2005; 50:227-34.
2. Jemal A, Siegel R, Ward E, et al., Cancer statistics, 2008. CA Cancer J Clin 2008; 58:71-96.
3. Naruke T, Tsuchiya R, Kondo H, Asamura, H. Prognosis and survival after resection for bronchogenic carcinoma based on the 1997 TNM-staging classification: the Japanese experience. Ann Thorac Surg 2001; 71:1759-64.
4. Pfannschmidt J, Muley T, Bulzebruck H, et al., Prognostic assessment after surgical resection for non-small cell lung cancer: experiences in 2083 patients. Lung Cancer 2007; 55:371-7.
5. van Rens M T, de la Riviere A B, Elbers H R, van Den Bosch J M. Prognostic assessment of 2,361 patients who underwent pulmonary resection for non-small cell lung cancer, stage I, II, and IIIA. Chest 2000; 117:374-9.
6. Hirsch F R, Wynes M W, Gandara D R, Bunn P A Jr., The tissue is the issue: personalized medicine for non-small cell lung cancer. Clin Cancer Res 2010; 16:4909-11.
7. Mino-Kenudson M, Mark E J., Reflex testing for epidermal growth factor receptor mutation and anaplastic lymphoma kinase fluorescence in situ hybridization in non-small cell lung cancer. Arch Pathol Lab Med 2011; 135:655-64.
8. Pao W, Girard N., New driver mutations in non-small-cell lung cancer. Lancet Oncol 2011; 12:175-80.
9. Bria E, Milella M, Cuppone F, et al., Outcome of advanced NSCLC patients harboring sensitizing EGFR mutations randomized to EGFR tyrosine kinase inhibitors or chemotherapy as first-line treatment: a meta-analysis. Ann Oncol. 2011; 22:2277-85.
10. Gerber D E, Minna J D., ALK inhibition for non-small cell lung cancer: from discovery to therapy in record time. Cancer Cell 2010; 18:548-51.
11. Sasaki T, Jänne P A., New strategies for treatment of ALK-rearranged non-small cell lung cancers. Clin Cancer Res 2011; 17:7213-8.
12. Shaw A T, Solomon B., Targeting anaplastic lymphoma kinase in lung cancer. Clin Cancer Res 2011; 17:2081-6.
13. Shaw A T, Yeap B Y, Solomon B J, et al., Effect of crizotinib on overall survival in patients with advanced non-small-cell lung cancer harbouring ALK gene rearrangement: a retrospective analysis. Lancet Oncol 2011; 12:1004-12.
14. Yoshida A, Tsuta K, Nakamura H, et al., Comprehensive histologic analysis of ALK-rearranged lung carcinomas. Am J Surg Pathol 2011; 35:1226-34.
15. Hofman V, Bonnetaud C, Ilie M I, et al., Preoperative circulating tumor cell detection using the isolation by size of epithelial tumor cell method for patients with lung cancer is a new prognostic biomarker. Clin Cancer Res 2011; 17:827-35.
16. Krebs M G, Sloane R, Priest L, et al., Evaluation and prognostic significance of circulating tumor cells in patients with non-small-cell lung cancer. J Clin Oncol. 2011a; 29:1556-63.

17. Krebs M G, Hou J M, Sloane R, et al., Analysis of circulating tumor cells in patients with non-small cell lung cancer using epithelial marker-dependent and -independent approaches. J Thorac Oncol 2011b December 14.
18. Paterlini-Brechot P, Benali N L., Circulating tumor cells (CTC) detection: clinical impact and future directions. Cancer Lett 2007; 253:180-204.
19. Yu M, Stott S, Toner M, et al., Circulating tumor cells: approaches to isolation and characterization. J Cell Biol 2011; 192:373-82.
20. Maheswaran S, Sequist L V, Nagrath S, et al. Detection of mutations in EGFR in circulating lung-cancer cells. N Engl J Med 2008; 359:366-77.
21. Hofman V, Ilie M I, Long E, et al., Detection of circulating tumor cells as a prognostic factor in patients undergoing radical surgery for non-small-cell lung carcinoma: comparison of the efficacy of the CellSearch Assay™ and the isolation by size of epithelial tumor cell method. Int J Cancer 2011; 129:1651-60.
22. Hofman V, Long E, Ilie M, et al., Morphological analysis of circulating tumor cells in patients undergoing surgery for non-small cell lung carcinoma using the isolation by size of epithelial tumor cell (ISET) method. Cytopathology 2012; 23:30-8
23. Vona G, Sabile A, Louha M, et al., Isolation by size of epithelial tumor cells: a new method for the immunomorphological and molecular characterization of circulating tumor cells. Am J Pathol 2000; 156:57-63.
24. Hou J M, Krebs M, Ward T, et al., Circulating tumor cells as a window on metastasis biology in lung cancer. Am J Pathol 2011; 178:989-96.
25. Lecharpentier A, Vielh P, Perez-Moreno P, et al., Detection of circulating tumor cells with a hybrid (epithelial/mesenchymal) phenotype in patients with metastatic non-small cell lung cancer. Br J Cancer 2011; 105:1338-41.
26. Lababede O, Meziane M, Rice T., Seventh edition of the cancer staging manual and stage grouping of lung cancer: quick reference chart and diagrams. Chest 2011; 139:183-9.
27. Travis W D, Brambilla E, Noguchi M, et al., International association for the study of lung cancer/american thoracic society/european respiratory society international multidisciplinary classification of lung adenocarcinoma. J Thorac Oncol 2011; 6:244-85.
28. Rodig S J, Mino-Kenudson M, Dacic S, et al., Unique clinicopathologic features characterize ALK-rearranged lung carcinoma in the western population. Clin Cancer Res 2009; 15:5216-23.
29. Ogino S, Kawasaki T, Brahmandam M, et al., Sensitive sequencing method for KRAS mutation detection by pyrosequencing. J Mol Diagn 2005; 7:413-21.
30. Richman S D, Seymour M T, Chambers P, et al., KRAS and BRAF mutations in advanced colorectal cancer are associated with poor prognosis but do not preclude benefit from oxaliplatin or Irinotecan: Results From the MRC FOCUS Trial. J Clin Oncol 2009; 27:5931-7.
31. Hofman P, Ilie M, Hofman V, et al., Immunohistochemistry to identify EGFR mutations or ALK rearrangements in patients with lung adenocarcinoma. Ann Oncol 2011 Nov. 18.
32. Koivunen J P, Mermel C, Zejnullahu K, et al., EML4-ALK fusion gene and efficacy of an ALK kinase inhibitor in lung cancer. Clin Cancer Res 2008; 14:4275-83.
33. Lee J K, Park H S, Kim D W, et al., Comparative analyses of overall survival in patients with anaplastic lymphoma kinase-positive and matched wild-type advanced nonsmall cell lung cancer. Cancer 2011 Nov. 15.
34. Wu S G, Kuo Y W, Chang Y L, et al., EML4-ALK Translocation Predicts Better Outcome in Lung Adenocarcinoma Patients with Wild-Type EGFR. J Thorac Oncol 2012; 7:98-104.
35. Yang P, Kulig K, Boland J M, et al., Worse disease-free survival in never-smokers with ALK+ lung adenocarcinoma. J Thorac Oncol 2012; 7:90-7
36. Just P A, Cazes A, Audebourg A, et al., Histologic subtypes, immunohistochemistry, FISH or molecular screening for the accurate diagnosis of ALK-rearrangement in lung cancer: A comprehensive study of Caucasian non-smokers. Lung Cancer. 2011 Dec. 6
37. Paik J H, Choi C M, Kim H, et al., Clinicopathologic implication of ALK rearrangement in surgically resected lung cancer A proposal of diagnostic algorithm for ALK-rearranged adenocarcinoma. Lung Cancer 2011 Nov. 28.
38. Sasaki T, Rodig S J, Chirieac L R, et al., The biology and treatment of EML4-ALK non-small cell lung cancer. Eur J Cancer 2010; 46:1773-80
39. Popat S, Gonzalez D, Min T, et al., ALK translocation is associated with ALK immunoreactivity and extensive signet-ring morphology in primary lung adenocarcinoma. Lung Cancer 2011 Aug. 18. [Epub ahead of print]
40. Yi E S, Boland J M, Maleszewski J J, et al., Correlation of ICH and FISH for ALK gene rearrangement in non-small cell lung carcinoma: ICH score algorithm for FISH. J Thorac Oncol 2011; 6:459-65.
41. Kitamura A, Hosoda W, Sasaki E, et al., Immunohistochemical detection of EGFR mutation using mutation-specific antibodies in lung cancer. Clin Cancer Res 2010; 16:3349-55.
42. Krebs M G, Hou J M, Ward T H, et al., Circulating tumor cells: their utility in cancer management and predicting outcomes. Ther Adv Med Oncol 2010; 2:351-65.
43. Katayama R, Khan T M, Benes C, et al., Therapeutic strategies to overcome crizotinib resistance in non-small cell lung cancers harboring the fusion oncogene EML4-ALK. Proc Natl Acad Sci USA 2011; 108:7535-40.
44. Heuckmann J M, Hölzel M, Sos M L, et al., ALK mutations conferring differential resistance to structurally diverse ALK inhibitors. Clin Cancer Res 2011; 17:7394-401.
45. Paterlini-Brechot P, Benali N L., Circulating tumor cells (CTC) detection: clinical impact and future directions. Cancer Lett. 2007; 253:180-204.
46. Krebs M G, Hou J M, Sloane R, Lancashire L, Priest L, Nonaka D, et al., Analysis of circulating tumor cells in patients with non-small cell lung cancer using epithelial marker-dependent and -independent approaches. J Thorac Oncol. 2012; 7:306-15.
47. Rhim A D, Mirek E T, Aiello N M, Maitra A, Bailey J M, McAllister F, et al., EMT and dissemination precede pancreatic tumor formation. Cell. 2012; 148:349-61.
48. Klein C., Parallel progression of primary tumours and metastases. Nature Reviews Cancer, 2009 (9): 302-312.
49. National Lung Screening Trial Research Team: Aberle D R, Adams A M, Berg C D, Black W C, Clapp J D, Fagerstrom R M, Gareen I F, Gatsonis C, Marcus P M, Sicks J D. Reduced lung-cancer mortality with low-dose computed tomographic screening. N Engl J Med. 2011 4; 365:395-409.
50. Hofman V, Bonnetaud C, Ilie M I, Vielh P, Vignaud J M, Flejou J F, et al., Preoperative Circulating Tumor Cell Detection Using the Isolation by Size of Epithelial Tumor Cell Method for Patients with Lung Cancer Is a New Prognostic Biomarker. Clin Cancer Res. 2011; 17:827-35.
51. Hofman V, Long E, Ilie M, Bonnetaud C, Vignaud J M, Flejou J F, et al., Morphological analysis of circulating tumour cells in patients undergoing surgery for non-small cell lung carcinoma using the isolation by size of epithelial tumour cell (ISET) method. Cytopathology. 2012; 23:30-8.
52. Mazzone P, Mekhail T., Current and emerging medical treatments for non-small cell lung cancer: a primer for pulmonologists. Respir Med. 2012; 106:473-92.
53. 2. Jemal A, Siegel R, Ward E, Hao Y, Xu J, Murray T, et al., Cancer statistics, 2008. CA Cancer J Clin. 2008; 58:71-96.
54. Mets O M, Buckens C F, Zanen P, Isgum I, van Ginneken B, Prokop M, Gietema H A, Lammers J W, Vliegenthart R, Oudkerk M, van Klaveren R J, de Koning H J, Mali W P, de Jong P A., Identification of chronic obstructive pulmonary disease in lung cancer screening computed tomographic scans. JAMA. 2011; 306:1775-81.55. Mujezinovic F, Alfirevic Z. Procedure-related complications of amniocentesis and chorionic villous sampling: a systematic review. Obstet Gynecol 2007; 110:687-694.
56. Dan S, Wang W, Ren J, Li Y, Hu H, Xu Z, Lau T K, Xie J, Zhao W, Huang H et al., Clinical application of massively parallel sequencing-based prenatal noninvasive fetal trisomy test for trisomies 21 and 18 in 11105 pregnancies with mixed risk factors. Prenat Diagn 2012; 32:1-8.
57. Zimmermann B, Hill M, Gemelos G, Demko Z, Banjevic M, Baner J, Ryan A, Sigurjonsson S, Chopra N, Dodd M et al., Noninvasive prenatal aneuploidy testing of chromosomes 13, 18, 21, X, and Y, using targeted sequencing of polymorphic loci. Prenat Diagn 2012; 32:1233-1241.
58. Lo Y M, Lun F M, Chan K C, Tsui N B, Chong K C, Lau T K, Leung T Y, Zee B C, Cantor C R, Chiu R W., Digital PCR for the molecular detection of fetal chromosomal aneuploidy. Proc Natl Acad Sci USA 2007; 104:13116-13121.
59. Chiu R W, Chan K C, Gao Y, Lau V Y, Zheng W, Leung T Y, Foo C H, Xie B, Tsui N B, Lun F M et al., Noninvasive prenatal diagnosis of fetal chromosomal aneuploidy by massively parallel genomic sequencing of DNA in maternal plasma. Proc Natl Acad Sci USA 2008; 105:20458-20463.
60. Fan H C, Blumenfeld Y J, Chitkara U, Hudgins L, Quake S R., Noninvasive diagnosis of fetal aneuploidy by shotgun sequencing DNA from maternal blood. Proc Natl Acad Sci USA 2008; 105:16266-16271.
61. Vona G, Beroud C, Benachi A, Quenette A, Bonnefont J P, Romana S, Munnich A, Vekemans M, Dumez Y, Lacour B et al., Enrichment, immunomorphological, and genetic characterization of fetal cells circulating in maternal blood. Am J Path 2002; 160:51-58.
62. Mouawia H, Saker A, Jais J P, Benachi A, Bussieres L, Lacour B, Bonnefont J P, Frydman R, Simpson J L, Paterlini-Brechot P., Circulating trophoblastic cells provide genetic diagnosis in 63 fetuses at risk for cystic fibrosis or spinal muscular atrophy. Reprod Biomed Online 2012; 25:508-520.
63. Shettles L B. Use of the Y chromosome in prenatal sex determination. Nature 1971; 230:52-53.
64. Rhine S A, Cain J L, Cleary R E, Palmer C G, Thompson J F. Prenatal sex detection with endocervical smears: successful results utilizing Y-body fluorescence. Am J Obstet Gynecol 1975; 122:155-160.
65. Ergin T, Baltaci V, Zeyneloglu H B, Duran E H, Ergenell M H, Batioglu S. Non-invasive early prenatal diagnosis using fluorescent in situ hybridization on transcervical cells: comparison of two different methods for retrieval. Eur J Obstet Gynecol Reprod Biol 2001; 95:37-41.
66. Cioni R, Bussani C, Bucciantini S, Scarselli G. Fetal cells in a transcervical cell sample collected at 5 weeks of gestation. J Mat-Fet Neonat Med 2005; 18:271-273.
67. Cioni R, Bussani C, Scarselli B, Bucciantini S, Marchionni M, Scarselli G. Comparison of two techniques for transcervical cell sampling performed in the same study population. Prenat Diagn 2005; 25:198-202.
68. Bussani C, Scarselli B, Cioni R, Bucciantini S, Scarselli G. Use of the quantitative fluorescent-PCR assay in the study of fetal DNA from micromanipulated transcervical samples. Mol Diagn 2004; 8:259-263.
69. Kingdom J, Sherlock J, Rodeck C, Adinolfi M. Detection of trophoblast cells in transcervical samples collected by lavage or cytobrush. Obstet Gynecol 1995; 86:283-288.
70. Massari A, Novelli G, Colosimo A, Sangiuolo F, Palka G, Calabrese G, Camurri L, Ghirardini G, Milani G, Giorlandino C et al. Non-invasive early prenatal molecular diagnosis using retrieved transcervical trophoblast cells. Hum Genet 1996; 97:150-155.
71. Chang S D, Lin S L, Chu K K, His B L. Minimally-invasive early prenatal diagnosis using fluorescence in situ hybridization on samples from uterine lavage. Prenat Diagn 1997; 17:1019-1025.
72. Chou M M, Lin S K, Ho E S. Severe limb reduction defects after uterine lavage at 7-8 weeks' gestation. Prenat Diagn 1997; 17:77-80.
73. Zhang L, Cui X, Schmitt K, Hubert R, Navidi W, Arnheim N. Whole genome amplification from a single cell: implications for genetic analysis. Proc Natl Acad Sci USA 1992; 89:5847-5851.
74. Imudia A N, Suzuki Y, Kilburn B A, Yelian F D, Diamond M P, Romero R, Armant D R. Retrieval of trophoblast cells from the cervical canal for prediction of abnormal pregnancy: a pilot study. Hum Reprod 2009; 24:2086-2092.
75. Coumans, F. A. W., et al., Filter Characteristics Influencing Circulating Tumor Cell Enrichment from Whole Blood, PLOS ONE 8 (4): e61770 (April 2013)
76. Coumans, F. A. W., et al., Filtration Parameters Influencing Circulating Tumor Cell Enrichment from Whole Blood, PLOS ONE 8 (4): e61774 (April 2013).

The invention claimed is:

1. A process for analyzing DNA molecules in rare cells isolated from blood obtained from a subject, the method comprising:

a) treating a diluted blood sample with an anticoagulant, selectively only lysing red blood cells in the diluted blood sample that is treated with the anticoagulant, and producing a fixed blood sample by fixing the diluted blood sample that is treated with the anticoagulant and has lysed red blood cells;

b) filtering the fixed diluted blood sample from step a) by vertical filtration with a negative pressure through a polycarbonate filter, wherein the filter has a pore size from 3 μm to 30 μm, has a pore density from $3\times10^3$ pores/cm$^2$ to $5\times10^6$ pores/cm$^2$, and is suitable for retention of the rare cells but permits passage of cells smaller than the rare cells, wherein the rare cells are nucleated cells larger than neutrophils and mature lymphocytes, and wherein the filter comprises elementary filtration areas, each of the elementary filtration areas having a surface which equals to the area of a disk with a diameter between 0.6 cm and 3 cm, wherein the surface of each of the elementary filtration areas and the number of elementary filtration areas of the filter are chosen according to the nature of a fluid to be filtered, the nature of biological particles to be separated when the filter is used, and the volume of the fluid to be filtered, and wherein the ratio of a total volume of fluid filtered through the surface of each of the elementary filtration areas of the filter to the area of each of the elementary filtration areas of the filter is less than 40 ml/cm$^2$;

c) recovering the rare cells on the filter or the rare cells detached from the filter cells; and e) analyzing the DNA molecules from the recovered rare cells, thereby analyzing the DNA molecules in the rare cells isolated from the blood obtained from the subject.

2. The process of claim 1, wherein the subject has a cancer or a tumor; or is suspected of having a cancer or a tumor; or is at risk of having a cancer or a tumor.

3. The process of claim 2, wherein the recovered rare cells comprise circulating tumor cells (CTCs).

4. The process of claim 3, wherein DNA molecules from the CTCs are different from DNA molecules from leukocytes.

5. The process of claim 4, wherein the DNA molecules analyzed in step e) comprise mutated DNA molecules and the analyzing step comprises identifying the mutated DNA molecules.

6. The process of claim 1, wherein, in step e), said analyzing DNA molecules from the recovered rare cells comprise one or more of PCR analyses, high throughput sequencing, and methylation analyses.

7. The process of claim 1, wherein the DNA molecules analyzed in step e) comprise mutated DNA molecules and the analyzing step comprises identifying the mutated DNA molecules.

8. The process of claim 1, wherein said analyzing the DNA molecules from the recovered rare cells comprises detecting whether DNA mutations are present in the recovered rare cells.

9. The process of claim 1, wherein the blood sample is, further treated with a proteolytic agent prior to the filtering step.

10. The process of claim 1, wherein the pore size from 3 μm to 30 μm is a pore size from 5 μm to 25 μm.

* * * * *

SEQUENCE LISTING

```
Sequence total quantity: 3
SEQ ID NO: 1            moltype = DNA  length = 26
FEATURE                 Location/Qualifiers
source                  1..26
                        mol_type = other DNA
                        organism = synthetic construct
SEQUENCE: 1
```

-continued

```
gcataaagat gtcatcatca accaag                                 26

SEQ ID NO: 2           moltype = DNA  length = 24
FEATURE                Location/Qualifiers
source                 1..24
                       mol_type = other DNA
                       organism = synthetic construct
SEQUENCE: 2
tcttgccagc aaagcagtag ttgg                                   24

SEQ ID NO: 3           moltype =   length =
SEQUENCE: 3
000
```